United States Patent
Bezwada

(10) Patent No.: US 8,062,653 B2
(45) Date of Patent: Nov. 22, 2011

(54) CONTROLLED RELEASE OF NITRIC OXIDE AND DRUGS FROM FUNCTIONALIZED MACROMERS AND OLIGOMERS

(75) Inventor: Rao S. Bezwada, Whitehouse Station, NJ (US)

(73) Assignee: Bezwada Biomedical, LLC, Hillborough, NJ (US)

( * ) Notice: Subject to any disclaimer, the term of this patent is extended or adjusted under 35 U.S.C. 154(b) by 175 days.

(21) Appl. No.: 12/508,854

(22) Filed: Jul. 24, 2009

(65) Prior Publication Data

US 2010/0209469 A1 Aug. 19, 2010

Related U.S. Application Data

(60) Provisional application No. 61/153,349, filed on Feb. 18, 2009.

(51) Int. Cl.
*A61F 2/00* (2006.01)
*A61K 31/74* (2006.01)
*A61K 31/21* (2006.01)

(52) U.S. Cl. .............. 424/423; 424/78.08; 514/509

(58) Field of Classification Search .......... 424/423, 424/78.08; 514/509; 525/450, 415
See application file for complete search history.

(56) References Cited

U.S. PATENT DOCUMENTS

| | | | |
|---|---|---|---|
| 7,199,258 B2 | 4/2007 | Del Soldato et al. | |
| 7,279,176 B1 * | 10/2007 | West et al. | 424/426 |
| 7,442,826 B2 | 10/2008 | Rivolta et al. | |
| 7,629,368 B2 | 12/2009 | Del Soldato et al. | |
| 7,691,364 B2 | 4/2010 | Bezwada | |
| 7,723,382 B2 | 5/2010 | Del Soldato et al. | |
| 7,858,665 B2 | 12/2010 | Ongini et al. | |
| 7,883,714 B2 | 2/2011 | Earl et al. | |
| 2002/0028845 A1 | 3/2002 | Ekwuribe et al. | |
| 2002/0143047 A1 * | 10/2002 | Galer et al. | 514/420 |
| 2008/0175881 A1 * | 7/2008 | Ippoliti et al. | 424/423 |
| 2008/0288176 A1 | 11/2008 | Tam et al. | |
| 2009/0076174 A1 | 3/2009 | Bezwada | |
| 2009/0092676 A1 * | 4/2009 | Richard et al. | 424/501 |

FOREIGN PATENT DOCUMENTS

| | | | |
|---|---|---|---|
| CN | 101053662 | * | 10/2007 |
| CN | 101053662 A | | 10/2007 |
| WO | 01-30334 A2 | | 5/2001 |
| WO | 2004-004648 A2 | | 1/2004 |
| WO | WO 2005/053685 A1 | * | 6/2005 |
| WO | WO 2007/025632 A1 | * | 3/2007 |
| WO | WO 2007/090793 A1 | * | 8/2007 |
| WO | WO 2008/071421 A1 | * | 6/2008 |

* cited by examiner

*Primary Examiner* — Blessing Fubara
(74) *Attorney, Agent, or Firm* — Moser Taboada

(57) ABSTRACT

The present invention provides NO and, optionally, drug releasing macromers and oligomers wherein the drug molecule and NO releasing moiety are linked an absorbable macromer or oligomeric chain susceptible to hydrolytic degradation and wherein the macromer or oligomer comprises of repeat units derived from safe and biocompatible molecules such as glycolic acid, lactic acid, caprolactone and p-dioxanone. Furthermore, the present invention relates to controlled release of nitric oxide (NO) and/or drug molecule from a NO and drug releasing macromer or oligomer. Moreover, the present invention also relates to medical devices, medical device coatings and therapeutic formulations comprising of nitric oxide and drug releasing macromers and oligomers of the present invention.

17 Claims, No Drawings

CONTROLLED RELEASE OF NITRIC OXIDE AND DRUGS FROM FUNCTIONALIZED MACROMERS AND OLIGOMERS

This Application claims the priority of U.S. Ser. No. 61/153,349, filed 18 Feb. 2009.

FIELD OF THE INVENTION

The present invention relates to NO and, optionally, drug molecule releasing macromers and oligomers wherein the drug molecule and NO releasing moiety are linked a hydrolytically degradable macromer or oligomeric chain comprising of repeat units derived from safe and biocompatible molecules such as glycolic acid, lactic acid, caprolactone and p-dioxanone. The present invention also relates to controlled release of NO and, optionally drug molecule from macromers and oligomers of the present invention. Furthermore, the present invention relates to medical devices, medical device coatings and therapeutic formulations comprising nitric oxide and drug releasing macromers and oligomers of the present invention.

The present invention relates to NO and, optionally, drug molecule releasing macromers and oligomers wherein the drug molecule and NO releasing moiety are linked to a hydrolytically degradable macromer or oligomeric chain comprising of repeat units derived from safe and biocompatible molecules such as glycolic acid, lactic acid, caprolactone and p-dioxanone. The present invention also relates to controlled release of NO and drug molecule from macromers and oligomers of the present invention. Furthermore, the present invention relates to medical devices, medical device coatings and therapeutic formulations comprising nitric oxide and drug releasing macromers and oligomers of the present invention.

Nitric oxide (referred to herein as "NO") is a vital biological molecule. It plays a significant role in diverse biological processes such as host defense, cardiovascular regulation, signal transduction, neurotransmission and wound healing. In addition to helping body cells to communicate with each other by transmitting signals throughout the entire body, NO assists the immune system at fighting off bacteria and defending against tumors. Furthermore, it helps reduce inflammation and regulate blood pressure by dilating arteries. Moreover, NO assist in gastric motility and alleviating erectile dysfunction.

NO is a well known inhibitor of platelet adhesion and activation. Continuous release of NO from surface of endothelial cells effectively prevents the adhesion/activation of platelets on normal blood vessel walls. Furthermore, NO is also a potent inhibitor of smooth muscle cell proliferation, and agents that release or generate NO locally have been proposed as systematic drugs to prevent and/or treat restenosis and thrombus formation when delivered to treatment sites inside an individual that have come in contact with medical devices such as cardiovascular drug-eluting stents, diagnostic catheters, guide wires, guide catheters, PTCA balloon catheters (for percutaneous transluminal coronary angioplasty) in blood vessels, in-dwelling sheaths (venous and arterial), intraaortic balloon pump catheters, intravascular sensors, extracorporeal blood loop circuits, intravenous grafts/shunts and adhesion prevention barriers including meshes. Furthermore, NO released from wound resident cells also play an important role in unique cell signaling pathways and the re-establishment of the microcirculation as newly vascularized tissue is formed. Moreover, NO is anti-inflammatory, which would be of value for in dwelling urethral or TPN catheters.

Medical research is rapidly discovering therapeutic applications for NO including the fields of vascular surgery and interventional cardiology. For example, Stents and DES cardiovascular stents have been used clinically for treatment of occluded cardiac arteries for over fifteen years and their use has resulted in substantial clinical benefit for cardiac patients. However, a significant problem with bare-metal stents in clinical usage is restenosis of the artery, leading to recurrence of the primary cardiac symptoms and effects. Localized NO release appears to address some of the root causes of the restenosis including: 1) the fibrinogen binding-platelet adhesion-release of platelet derived growth factor cycle and 2) inflammation and associated release of growth factors. NO release also addresses associated problems with undesired smooth muscle cell growth (Raulli et al. WO2007/053578 A2), and provides a long-term biocompatible solution to the presence of the stent by stimulating rapid endothelialization of the stent itself. Stent endothelialization results in a natural cell coating for the stent that essentially seeks to make the stent surface invisible to the blood and its components. Delayed endothelialization has been linked of late in stent thrombosis, a potentially fatal event. Thus, the use of nitric oxide eluting stent coatings has many advantages over antiproliferatives drugs, especially at the very early stages in the stent placement pathophysiology. One of the key benefits of NO is the stimulation of endothelialization which is a primary measure of healing. Thus, rapid division of endothelial cells and their rapid colonization of the stent material may be an ultimate safety feature in DES development. Hence, there exists a need for better technology addressing the release of NO and, optionally, additional drugs in drug-eluting stents.

Researchers have sought various ways to deliver NO to damaged tissue and to tissues and organs at risk of injury. One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administrated L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate pro-drugs such as nitroglycerin tablets, intravenous suspensions, sprays and transdermal patches. The human body rapidly converts nitroglycerin into NO; however, enzyme levels and co-factors required to activate the pro-drug are rapidly depleted, resulting in drug tolerance. Moreover, systemic NO administration can have devastating side effects including hypotension and free radical cell damage. Therefore, using organic nitrate pro-drugs to maintain systemic anti-restenotic therapeutic blood levels is not currently possible.

Ideally, NO should be delivered in a controlled manner specifically to those tissues and organs that have been injured or are at risk of injury. Furthermore, topical NO delivery may also be a crucial component of a new generation of wound dressings, since few controlled release drugs are currently available. Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis, an inhibitory therapeutic such as NO must be administered at a controlled rate for a sustained period at therapeutic levels. Consequently, any NO-releasing medical device that releases NO at a controlled rate and is used to treat restenosis must be suitable for implantation. An ideal candidate device is the drug eluting vascular stent. Therefore, a stent that safely provides therapeutically effective amounts of NO and a drug molecule at a controlled rate to a precise location simultaneously would represent a significant advance in restenosis treatment and prevention.

Various compounds have been used to deliver NO therapeutically. Nitric oxide-releasing compounds suitable for in vivo applications have been developed by a number of investigators. As early as 1960 it was demonstrated that nitric oxide gas could be reacted with amines to form NO-releasing anions having the following general formula 1 R—R'N—N(O)NO wherein R and R' are ethyl. Salts of these compounds could spontaneously decompose and release NO in solution. (Chen et al. US 2008/0220048A1).

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 and by Hrabie et al., J. Org. Chem. 1993, 58:1472-1476, all of which are herein incorporated by reference.

Briefly, Hrabie et al. describes NO-releasing intramolecular salts (zwitterions) having the general formula 2 RN[N(O)NO$^-$](CH$_2$)NH$_2$$^+$R'.

The [N(O)NO]$^-$ (abbreviated hereinafter as NONO) containing compounds release NO via a first-order reaction that is predictable and easily quantified. This is in sharp contrast to other known NO-releasing compounds such as the S-nitrosothiol series as described in U.S. Pat. Nos. 5,380,758, 5,574,068 and 5,583,101. Stable NO-releasing compounds have been coupled to amine containing polymers. U.S. Pat. No. 5,405,919 describes biologically acceptable polymers that may be coupled to NO-releasing groups including polyolefins, such as polystyrene, polypropylene, polyethylene, polytetrafluoroethylene and polyvinylidene, and polyethylenimine, polyesters, polyethers, polyurethanes and the like. Medical devices, such as arterial stents, composed of these polymers represent a potential means for the site-specific delivery of NO.

Nitric oxide-donor compounds and compositions comprising them can be useful for treating cardiovascular disorders, gastrointestinal disorders, hepatic disorders and for inhibiting platelet adhesion were developed by Nicoletta et al. (WO Patent No. 2008/095841 A2). However, the Nicoletta disclosure does not relate to and also does not provide macromers and oligomers that release nitric oxide and, optionally, drug molecule. Furthermore, the Nicoletta disclosure does not relate to and also does not provide compositions comprising NO and drug releasing macromers and oligomers, combinations thereof and their blends with absorbable and non-absorbable polymers for applications in medical devices and medical device coatings. Moreover, the Nicoletta disclosure also does not teach art by which the rate of release of NO can be controlled.

There are a number of delivery methods of nitric oxide through a polymer including use of small molecule N-diazeniumdiolates from a pore matrix (WO 2007/053578, Raulli et al), use of N-diazeniumdiolate polymers (U.S. Pat. Nos. 5,405,919 and 5,525,357 Keefer et al., U.S. Pat. No. 6,703,046 Fitzhugh et al), nitrosothiols (U.S. Pat. No. 6,673,891 Stamler et al.) and nitroprusside (U.S. Pat. No. 6,656,217 Herzog et al.). However, N-diazeniumdiolate small molecules and polymers have the potential to form carcinogenic nitrosamines (WO 2007/053578, Raulli et al). The nitrosothiols have been shown to be unstable and labile to standard sterilization methods, and nitroprusside is difficult to sterilize. Both nitrosothiols and nitroprusside require metabolism to release NO and are subject to tolerance formation. Arnold et al. have previously reported C-diazeniumdiolate polymers (U.S. Pat. No. 7,105,502; US Pat. Application 2005/0203069). C-daizemiumdiolate polymers were also reported by Kalivretenos et al. (WO 2007/053578). Chen et al (US Patent Application 2008/0220048) reported NO releasing biodegradable polymers derived from [1,4]oxazepan-7-one suitable for use as medical devices and coatings for medical devices. Raulli et al (WO 2007/053578) described multiphasic nitric oxide and anti-proliferative drug eluting polymer coatings for medical devices wherein the NO is released by a NO donor selected from a group consisting of C-diazeniumdiolates, O-diazenium diolates, N-diazenium diolates, nitrosothiols, organic nitrates and nitrites, nitroprusside and other iron nitrosyl compounds, ruthenium/NO or other metal/NO complexes, heterocyclic N-oxides, messianic heterocycles, C-nitroso compounds, oximes, N-hydroxyguanidines and N-hydroxyureas, and other nitric oxide releasing compounds. However, all these NO donors do not provide us with a controlled release of NO.

Polymers containing groups capable of delivering NO, for example polymers containing diazeniumdiolate groups (NONOate groups), have been used to coat medical devices. Furthermore, the use of NONOates for the release of nitric oxide to specifically treat tissue that has been injured or is at risk of injury during sepsis or shock has been described in at least Saavedra et al. U.S. Pat. No. 5,814,656, the disclosure of which is incorporated herein by reference. Insoluble polymeric NONOates have also been generally described in Smith et al. U.S. Pat. No. 5,519,020, the disclosure of which is also incorporated herein by reference. These polymers were used to deliver NO to specific tissues, and results have shown that controlled release of NO to a specific site greatly reduced the inflammation and accelerates the healing process at that site. However, decomposition products of NONOates under oxygenated conditions can include nitrosamines, some of which may be carcinogenic. In addition, NONOates generally release NO radical, which is rapidly consumed by hemoglobin and can be toxic in individuals with arteriosclerosis. Furthermore, the elasticity of known NO-delivering polymers is generally inadequate, making it difficult to coat medical devices with the polymer and deliver NO with the coated device under physiological conditions. Protein based polymers have a high solubility in blood, which results in short lifetimes. Finally, many NO-delivering polymers cannot be sterilized without loss of NO from the polymer and amounts of NO delivered are limiting.

There are many shortcomings associated with present methods of delivering NO to treatment sites. NO itself is too reactive to be used without some means of stabilizing the molecule until it reaches the treatment site. Thus, NO is generally delivered to treatment sites in an individual by means of polymers and small molecules which release NO. However, these polymers and small molecules typically release NO rapidly. As a result, they have short shelf lives and rapidly lose their ability to deliver NO under physiological conditions. For example, the lifetime of S-nitroso-D,L-penicillamine and S-nitrosocysteine in physiological solution is no more than about an hour. As a result of the rapid rate of NO release by these compositions, it is difficult to deliver sufficient quantities of NO to a treatment site for extended periods of time or to control the amount of NO delivered.

Although, work has been carried out in the past to develop NO donors and NO donor drug molecules including NO donor aspirin (US Patent Publication No. 2008/0288176), the work suffers from the following disadvantages (a) the rate of release of nitric oxide and drug molecule cannot be controlled (b) Some of the NO donors reported so far release toxic and carcinogenic nitrosamines upon decomposition under oxygenated conditions (c) Some of the NO donors release NO radical, which is rapidly consumed by hemoglobin and is toxic to individuals with arteriosclerosis and (c) NO donors reported in the literature have short lives and they rapidly lose their ability to deliver NO under physiological conditions. In light of the above drawbacks, therefore, there is a need for new molecules and compositions capable of delivering NO and drug to treatment sites in a controlled manner and which can overcome the aforementioned shortcomings.

The present invention overcomes the aforementioned challenges by providing NO and drug releasing macromers and oligomers wherein the rate, extent and site of release of NO and the drug molecule can be controlled independently of each other. NO and drug releasing macromers and oligomers of the present invention have highly controllable hydrolysis profiles, increased solubility, improved bioavailability, improved efficacy and enhanced functionality. The controlled release profiles represent slow, moderate and/or rapid release of drug and nitric oxide. This release may be targeted to one or more specific organs or parts of the body. The hydrolytic degradation of some specific NO and drug releasing macromers and oligomers of the present invention typically releases drug molecule as such with no change in native chemical structure and efficacy. This invention provides greater control of the bioavailability of the drug and nitric oxide while retaining the inherent biological properties of both.

NO and drug releasing macromers and oligomers of the present invention comprise of a drug molecule and a NO releasing moiety linked to each other via a hydrolytically degradable linker. This hydrolytically degradable linker comprises of repeat units derived from safe and biocompatible molecules such as glycolic acid, lactic acid, p-dioxanone and caprolactone, key components of all commercially available absorbable medical devices. The hydrolytic degradation rate of NO and drug releasing macromers and oligomers of the present invention is controlled by the number of repeat units in the linker as well as by the choice of the safe and biocompatible molecules from which the repeat units are derived. For example, NO and drug releasing macromers and oligomers of the present invention comprising of degradable linker containing repeat units derived from glycolic acid will hydrolyze faster than the one comprising repeat units derived from p-dioxanone. Similarly, NO and drug releasing macromers and oligomers of the present invention comprising of degradable linker containing repeat units derived from lactic acid and caprolactone should take much longer to hydrolyze than the ones wherein the degradable linker comprises of repeat units derived from glycolic acid and p-dioxanone.

A biologically active substance in the context of the present invention is a substance that can act on a cell, virus, organ or organism, including but not limited to drugs (i.e. pharmaceuticals) to create a change in the functioning of the cell, virus, organ or organism. In certain embodiments of the invention, the biologically active substances are organic molecules having molecular weight of about 600 or less, or to polymeric species such as proteins, nucleic acids, and the like. A biologically active substance can be a substance used in therapy of an animal, preferably a human. For use in the invention, a biologically active substance bears, or has a functional homolog that bears, one or more hydroxyl, amino or carboxylic acid substituents, including functional derivatives such as esters, amides, methyl ethers, glycosides and other derivatives that are apparent to those skilled in the art.

In certain embodiments, a biologically active substance has one or more aromatic rings. Phenol(hydroxybenzene) is the simplest example of a phenolic compound, but most phenolics have two or more hydroxyl groups and are bioactive substances occurring widely in food plants that are eaten regularly by substantial numbers of animals and people and have been found to be safe compounds. Included in the definition of biologically active phenolics are poly-phenols having complex substitution patterns and compounds having condensed rings Biologically active substances are well known (e.g., aspirin and capsaicin) and have been beneficially administered to patients in need thereof for more than a century. One problem that has been associated with many biologically active substances is that they can be difficult to dissolve in water or the human body and can also be very difficult to polymerize. Due to the availability and numerous uses of biologically active substances, it is desirable to enhance their native value by, for example, providing compounds or combinations of compounds with a specific controlled degradation profile or range enabling controlled release of the biologically active substance over an extended, controllable time range.

Although, work has been carried out in the past to develop NO donors and NO donor drug molecules including NO donor aspirin (US Patent Publication No. 2008/0288176), the work suffers from the following disadvantages (a) the rate of release of nitric oxide and drug molecule cannot be controlled (b) Some of the NO donors reported so far release toxic and carcinogenic nitrosamines upon decomposition under oxygenated conditions (c) Some of the NO donors release NO radical, which is rapidly consumed by hemoglobin and is toxic to individuals with arteriosclerosis and (d) NO donors reported in the literature have short lives and they rapidly lose their ability to deliver NO under physiological conditions.

In light of the above drawbacks of the prior art, therefore, there is a need for new NO releasing therapeutic agents and compositions therefrom which are susceptible to hydrolytic degradation and release Nitric oxide and drug molecule in a controlled manner without yielding any toxic and harmful by products.

SUMMARY OF INVENTION

The present invention provides NO and, optionally, drug releasing macromers and oligomers wherein the rate, extent and site of release of NO and the drug molecule (if present) can be controlled independently of each other. NO and drug releasing macromers and oligomers of the present invention have highly controllable hydrolysis profiles, increased solubility, improved bioavailability, improved efficacy and enhanced functionality. The controlled release profiles represent slow, moderate and/or rapid release of drug and nitric oxide. This release may be targeted to one or more specific organs or parts of the body. The hydrolytic degradation of some specific NO and drug releasing macromers and oligomers of the present invention releases drug molecule as such with no change in native chemical structure and efficacy. This invention provides greater control on the bioavailability of the drug and nitric oxide while retaining the inherent biological properties of both.

NO and drug releasing macromers and oligomers of the present invention comprise of a drug molecule and a NO releasing moiety linked to each other via a hydrolytically degradable macromeric or oligomeric chain. This hydrolytically degradable macromeric or oligomeric chain comprises of repeat units derived from safe and biocompatible molecules such as glycolic acid, lactic acid, p-dioxanone and caprolactone, key components of all commercially available absorbable medical devices.

The hydrolytic degradation rate of NO and drug releasing macromers and oligomers of the present invention is controlled by the number of repeat units in the linker as well as by the choice of the safe and biocompatible molecules from which the repeat units are derived. For example, NO and drug releasing macromers and oligomers of the present invention comprising of degradable linker containing repeat units derived from glycolic acid will hydrolyze faster than the one comprising repeat units derived from p-dioxanone. Similarly, NO and drug releasing macromers and oligomers of the present invention comprising of degradable linker containing repeat units derived from lactic acid and caprolactone should take much longer to hydrolyze than the ones wherein the degradable linker comprises of repeat units derived from glycolic acid and p-dioxanone.

In one embodiment, the present invention provides nitric oxide macromers and oligomers of formula A:

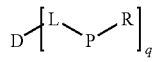
(A)

wherein:
L is —O—, —COO— or —NH—;
D is:
  (i) together or separately from L, a biologically active substance, in which case q is 1 to 4 inclusive;
  (ii) a moiety consisting of C, H, O, S or N, predominantly composed of C and H, and adapted with L to terminate moiety P, in which case q is 1 (or 2) to 4 inclusive;
  (iii) a polyester, polyether, mixed polyester/polyether, polyurethane or polyester polyurethane polymer formed from monomers selected to provide at least q linkages L, where q is an integer from 1 to 200 inclusive;
P is one of —[—X—]$_p$— or —[—Y—]$_p$—, wherein
p is independently an integer from 1 to 100 inclusive;
1 or more independently selected repeats X are:
  —CH$_2$COO— (glycolic acid moiety);
  —CH(CH$_3$)COO— (lactic acid moiety);
  —CH$_2$CH$_2$OCH$_2$COO— (dioxanone moiety);
  —CH$_2$CH$_2$CH$_2$CH$_2$CH$_2$COO— (caprolactone moiety);
  —(CH$_2$)$_y$COO— where y is one of the numbers 2, 3 or 4, or a number from 6 to 24 inclusive; or
  —(CH$_2$CH$_2$O)$_z$CH$_2$COO— where z is an integer between 2-24, inclusive;

0 or more independently selected repeats X are:
  any other repeat that is polyester polymerization compatible with the above recited repeats X;
the order and composition of repeats X is selected to provide a desired degradation of moiety -L-P—R;
1 or more independently selected repeats Y are:
  —COCH$_2$O— (glycolic ester moiety);
  —COCH(CH$_3$)O— (lactic ester moiety);
  —COCH$_2$OCH$_2$CH$_2$O— (dioxanone ester moiety);
  —COCH$_2$CH$_2$CH$_2$CH$_2$O— (caprolactone ester moiety);
  —CO(CH$_2$)$_m$O— where m is one of the numbers 2, 3 or 4, or a number from 6 to 24 inclusive; or,
  —COCH$_2$O(CH$_2$CH$_2$O)$_n$— where n is integer between 2-24 inclusive;
0 or more independently selected repeats Y are:
  any other repeat that is polyester polymerization compatible with the above recited repeats Y;
the order and composition of repeats Y is selected to provide a desired degradation of moiety -L-P—R; and
R is according to one of the applicable following options (a), (b) or (c):
  (a) where P is —[—X—]$_p$—, R can be an alkyl group, aryl, alkyl-aryl, an alicyclic group or alkyl-alicyclic, substituted with one or more —O—NO$_2$; and
  (b) where P is —[—Y—]$_p$—, R can be —NO$_2$;
  (c) where D is according to (ii) or (iii), R can be -L'D' or L'D'L"P'R',
    wherein,
      L' is L with opposite orientation, and D' is D, where D is a biologically active substance, and the linkage L'-P is chemically consistent with the recitations for L-P; and
      L" is L, P' is P except p is p', an integer from 1 to 20, and R' is R according to (a) or (b);
wherein:
  if D is defined by (i) and X or Y comprises —CH$_2$CH$_2$CH$_2$CH$_2$CH$_2$COO— or —COCH$_2$CH$_2$CH$_2$CH$_2$O—, then p is an integer from 2 to 100 inclusive;
  if L is —COO—, then the corresponding P is —[—X—]$_p$—, and, if L' is present, the last repeat X lacks the terminal O and L' is —O— or —NH—; and
  if L is —NH—, then the corresponding P is —[—Y—]$_p$—, and, if L' is present, the last repeat Y lacks the terminal O and L' is —O— or —OC(O)—.

The inventive compounds are defined as being functionalized with the defined X, Y and R substituents, which alter the native value or efficacy of the pre-functionalized compound by modifying the onset or length of action thereof.

Aryls are preferably C-6 or C-10, and can be further substituted with alkyl(s). Alicyclic rings are preferably C4 to C10, and can be further substituted with alkyl(s). Alkyls are preferably C2 to C6.

Integer p can be from 100 or less, 60 or less, or 40 or less, or 20 or less, or 10 or less, or 6 or less or 4 or less. Integer p can be 1 or more, 2 or more, 3 or more, or 4 or more. Integer p can be from one of the lower limits to one of the upper limits here recited.

D is defined by (i) and X or Y comprises —CH$_2$CH$_2$CH$_2$CH$_2$CH$_2$COO— or —COCH$_2$CH$_2$CH$_2$CH$_2$O—, then in certain embodiments, p is an integer from 2, 3 or 4 to one of the upper options listed above. In certain embodiments, where D is defined by (i) or (ii) and X or Y comprises —CH$_2$CH$_2$CH$_2$CH$_2$CH$_2$COO— or —COCH$_2$CH$_2$CH$_2$CH$_2$O—, then p is an integer from 2 to 100 inclusive. In certain embodiments, where D is defined by (ii) and X or Y comprises —CH$_2$CH$_2$CH$_2$CH$_2$CH$_2$COO— or —COCH$_2$CH$_2$CH$_2$CH$_2$CH$_2$O—, the limitations for p set forth above in this paragraph apply.

Where D is according to (ii) it can have MW of 600 or less, or 500 or less, or 400 or less, or 300 or less. By being predominately composed of C and H it is meant that the moiety has a predominately carbon-carbon skeleton. In certain embodiments, the moiety has a carbon-carbon skeleton, optionally with oxo (O=) and hydroxy substitutions.

In certain embodiments where D is according to (iii), q can be an integer from ll to hh, inclusive, where ll is 1, 2, 5, 10, 20 or 40, and hh is 4, 6, 10, 20, 40, 100 or 200. Where D is according to (i) or (ii), then q can be 1-3 inclusive, 1-2 or 1.

In certain embodiments, where D is according to (ii) or (iii), and R is according to (c), p' is an integer that is 1 or more, 2 or more, or 3 or more, and is 20 or less, 10 or less, 9 or less, 8 or less, 7 or less, 6 or less, or 5 or less (or a range therebetween, inclusive). In certain embodiments where D is according to (ii), D is a di-, tri- or quadra-acyl moiety, such as a succinate (from succinic acid), malonate, diglycolate, citrate, or the like.

Where R is according to (a) it can have MW of 600 or less, or 500 or less, or 400 or less, or 300 or less.

It should be noted that, except where specifically noted, the chemical moieties L and P above are written to insert in the formula with the same orientation as presented (i.e., they are not reversible left to right except as specifically noted).

All individual elements within each iteration of -[-L-P—R], can be independently selected according to the definitions herein.

In certain embodiments where D is according to (iii), some monomers of the polyester, polyether, mixed polyester/polyether, polyurethane or polyester polyurethane polymer provide two linkages L (independently selected). In certain embodiments, monomers provide at most one linkage L.

L', L" and L are independently selected according to the definitions herein. D' and D are independently selected according to the definitions herein. R' and R are independently selected according to the definitions herein.

In certain embodiments, the non-hydrocarbon functionalities in the nitric oxide macromer or oligomer, aside from D where D is a bioactive substance, comprise ether, ester, amide, halo, hydroxy and nitric oxide.

In one embodiment, the present invention provides nitric oxide and drug releasing macromers and oligomers of formula I to IV:

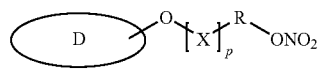

I

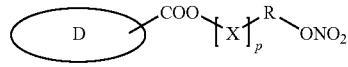

II

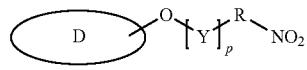

III

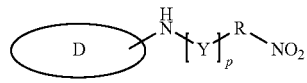

IV wherein D is according to recitals (i) or (ii) for Formula A. In one embodiment, D is according to recital (i)

In another embodiment, the present invention provides nitric oxide and drug releasing macromers and oligomers of formula V to XIII (where D=Drug, which is a biologically active substance):

V

VI

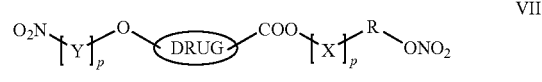

VII

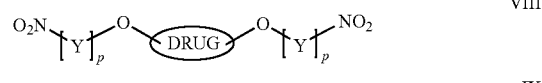

VIII

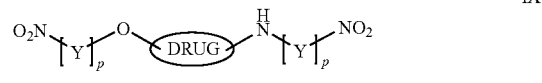

IX

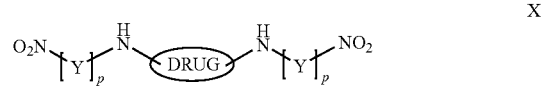

X

XI

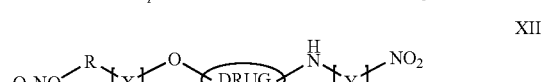

XII

XIII

In still another embodiment, the present invention provides NO and drug releasing macromers and oligomers of the formula XIV to XXI:

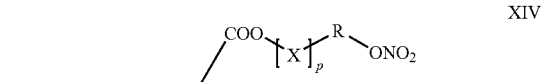

XIV

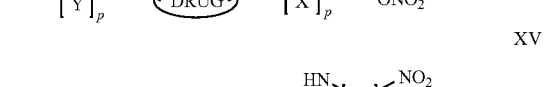

XV

XVI

XVII

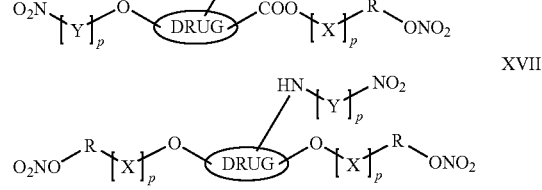

-continued

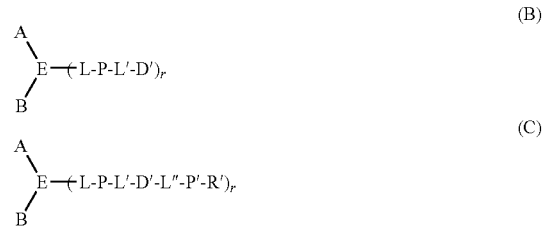

XVIII

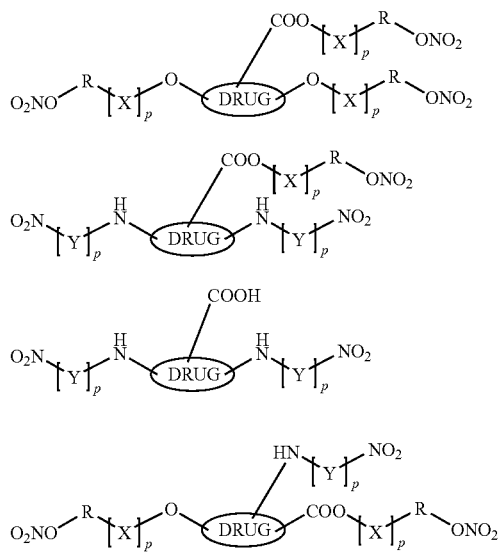

XIX

XX

XXI

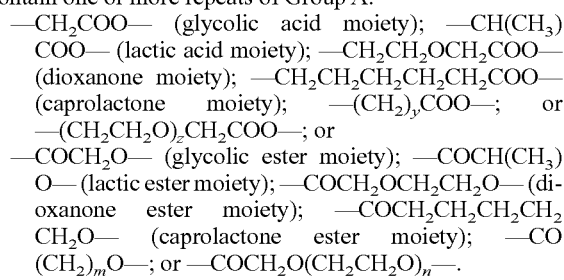

In certain analogs of Formulas V-XXI, Drug is replaced by D, which is according to recitals (i) or (ii) for Formula A.

In yet still another embodiment, the present invention provides NO and drug releasing macromers and oligomers according to formulas (I-XXI) wherein the drug molecules include but are not limited to non-steroidal anti-inflammatory drugs (NSAID) such as Naproxen, Aspirin, Ibuprofen, Indomethacin, Diclofenac and Tylenol or an antibiotic.

The present invention also provides implantable medical devices and medical device coatings comprising an effective amount of one or more of the NO and drug releasing macromers and oligomers of the present invention physically admixed with a polymer wherein a polymer can be absorbable or non-absorbable. Thus, the present invention provides at least two means of enhancing the biocompatibility of the medical device and/or providing for in-situ controlled release of NO and drug at the treatment site.

Exemplary embodiments of implantable medical devices and coatings comprising of NO and drug releasing macromers and oligomers of the present invention include, but are not limited to cardiovascular drug-eluting stents, diagnostic catheters, guide wires, guide catheters, PTCA balloon catheters (for percutaneous transluminal coronary angioplasty) in blood vessels, in-dwelling sheaths (venous and arterial), intraaortic balloon pump catheters, intravascular sensors, extracorporeal blood loop circuits, intravenous grafts/shunts and adhesion prevention barriers including meshes and coatings therefore wherein NO and drug are released in-situ such that restenosis is treated, prevented or inhibited.

In another embodiment, present invention also provides a drug delivery system, comprising: an effective amount of one or more of the NO and drug releasing macromers and oligomers of the present invention physically admixed, embedded or dispersed into the absorbable or non-absorbable polymer and the polymer is in the form of a polymeric matrix.

In still another embodiment, the present invention provides an anti-inflammatory or anti-oxidant or antimicrobial or a pharmaceutical composition comprising an effective amount of one or more of the NO and drug releasing macromers and oligomers of the present invention wherein said composition is in a form suitable for oral, enteral, parenteral, topical, transdermal, ocular, vitreal, rectal, nasal, pulmonary, or vaginal administration.

In yet another embodiment, the present invention provides a method for the treatment of diseases including but not limited to cancer and cardiovascular diseases which comprise administering to a subject in need thereof by means of controlled drug delivery a therapeutically effective amount of one or more of the NO and drug releasing macromers and oligomers of the present invention.

In still another embodiment, the present invention provides a pendant polymer or oligomer providing monomer according to formula B or C:

$$A\diagdown_{B\diagup}E\text{—}(L\text{-}P\text{-}L'\text{-}D')_r \qquad (B)$$

$$A\diagdown_{B\diagup}E\text{—}(L\text{-}P\text{-}L'\text{-}D'\text{-}L''\text{-}P'\text{-}R')_r \qquad (C)$$

wherein the component elements, excepting A and B, are consistent with the pendant moieties associated with D as defined by (iii). A and B are independently —OH, —NH$_2$ or —CO$_2$H.

DETAILED DESCRIPTION OF THE PRESENT INVENTION

Where L is a component of a biologically active substance, and when L is —O—, the biologically active substance typically has a hydroxy incorporating that oxygen, or is provided as an acyl derivative of the hydroxy. In this case, formula A where P is —[—Y—]$_p$— tends to provide forms that regenerate the hydroxy. Where P is —[—X—]$_p$—, it tends to provide forms including ether acids upon hydrolysis.

Where L is a component of a biologically active substance, and when L is —COO—, the biologically active substance typically has a carboxylic acid or salt thereof incorporating that moiety, or is provided as an ester derivative.

Where L is a component of a biologically active substance, and when L is —NH—, the biologically active substance typically has an amine or salt thereof incorporating that moiety, or is provided as an amide derivative.

It will be understood that the macromer or oligomer segments of formula A (or formula B or C described below) contain one or more repeats of Group A:
 —CH$_2$COO— (glycolic acid moiety); —CH(CH$_3$)COO— (lactic acid moiety); —CH$_2$CH$_2$OCH$_2$COO— (dioxanone moiety); —CH$_2$CH$_2$CH$_2$CH$_2$CH$_2$COO— (caprolactone moiety); —(CH$_2$)$_y$COO—; or —(CH$_2$CH$_2$O)$_z$CH$_2$COO—; or
 —COCH$_2$O— (glycolic ester moiety); —COCH(CH$_3$)O— (lactic ester moiety); —COCH$_2$OCH$_2$CH$_2$O— (dioxanone ester moiety); —COCH$_2$CH$_2$CH$_2$CH$_2$O— (caprolactone ester moiety); —CO(CH$_2$)$_m$O—; or —COCH$_2$O(CH$_2$CH$_2$O)$_n$—.

The presence of the above monomers tends to assure that a useful degradation profile will be obtained. However, it will be understood that additional, compatible monomers can be included in the macromer or oligomer segments. These can be identified by one of ordinary skill. In certain embodiments, the Group A repeats the majority of repeats. In certain embodiments, the Group A repeats comprise 60% or more, or 70% or more, or 80% or more, or 90% or more, or 95% or more of the number of repeats. In certain embodiments, the number of non-Group A repeats is less than half the repeats, and no more than 1, or 2, or 3.

In certain embodiments, the macromer or oligomer segments of formula A (or formula B or C described below) contain one or more repeats of Group B:

—CH$_2$COO— (glycolic acid moiety); —CH(CH$_3$)COO— (lactic acid moiety); —CH$_2$CH$_2$OCH$_2$COO— (dioxanone moiety); —CH$_2$CH$_2$CH$_2$CH$_2$CH$_2$COO— (caprolactone moiety); —(CH$_2$)$_y$COO— where y is one of the numbers 2, 3 or 4; or —(CH$_2$CH$_2$O)$_z$CH$_2$COO— where z is an integer between 2-24 inclusive; or —COCH$_2$O— (glycolic ester moiety); —COCH(CH$_3$)O— (lactic ester moiety); —COCH$_2$OCH$_2$CH$_2$O— (dioxanone ester moiety); —COCH$_2$CH$_2$CH$_2$CH$_2$CH$_2$O— (caprolactone ester moiety); —CO(CH$_2$)$_m$O— where m is one of the numbers 2, 3 or 4; or —COCH$_2$O(CH$_2$CH$_2$O)$_n$—.

In certain embodiments, the Group B repeats the majority of repeats. In certain embodiments, the Group B repeats comprise 60% or more, or 70% or more, or 80% or more, or 90% or more, or 95% or more of the number of repeats. In certain embodiments, the number of non-Group B repeats is less than half the repeats, and no more than 1, or 2, or 3.

In certain embodiments, the macromer or oligomer segments of formula A (or formula B or C described below) contain one or more repeats of Group C:

—CH$_2$COO— (glycolic acid moiety); —CH(CH$_3$)COO— (lactic acid moiety); —CH$_2$CH$_2$OCH$_2$COO— (dioxanone moiety); or —CH$_2$CH$_2$CH$_2$CH$_2$CH$_2$COO— (caprolactone moiety);

—COCH$_2$O— (glycolic ester moiety); —COCH(CH$_3$)O— (lactic ester moiety); —COCH$_2$OCH$_2$CH$_2$O— (dioxanone ester moiety); or —COCH$_2$CH$_2$CH$_2$CH$_2$CH$_2$O— (caprolactone ester moiety).

In certain embodiments, the Group C repeats the majority of repeats. In certain embodiments, the Group C repeats comprise 60% or more, or 70% or more, or 80% or more, or 90% or more, or 95% or more of the number of repeats. In certain embodiments, the number of non-Group C repeats is less than half the repeats, and no more than 1, or 2, or 3. In certain embodiments, p is 40 or less, or 20 or less, or 10 or less, or 8 or less or 6 or less or 4 or less, the Group C repeats are 2 or more, 3 or more, 4 or more, 5 or more, or 10 or more.

The present invention also provides NO and drug releasing macromers and oligomers wherein the macromer or oligomer is selected from the following formulas (where n=2, 3 or 4):

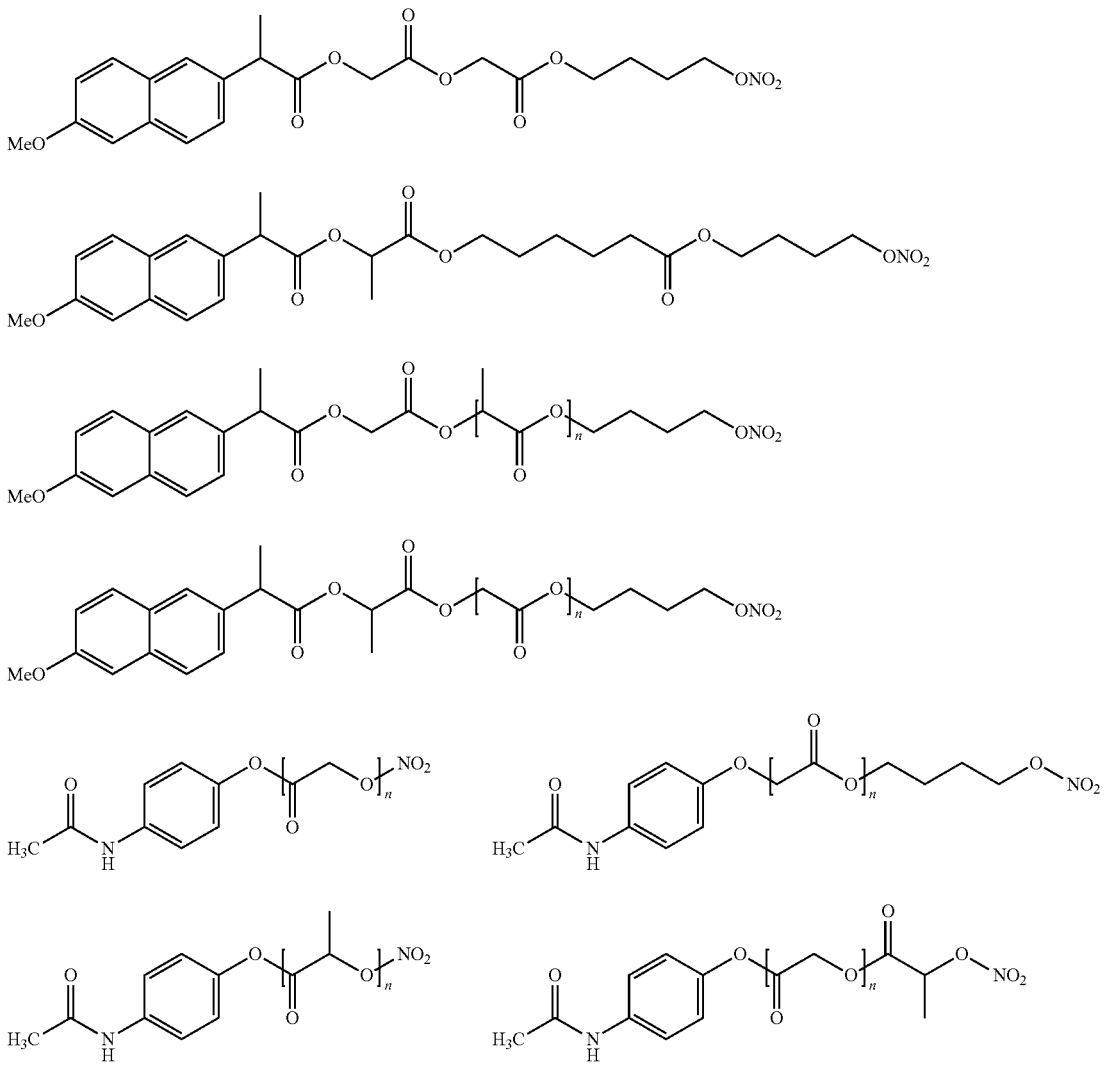

-continued
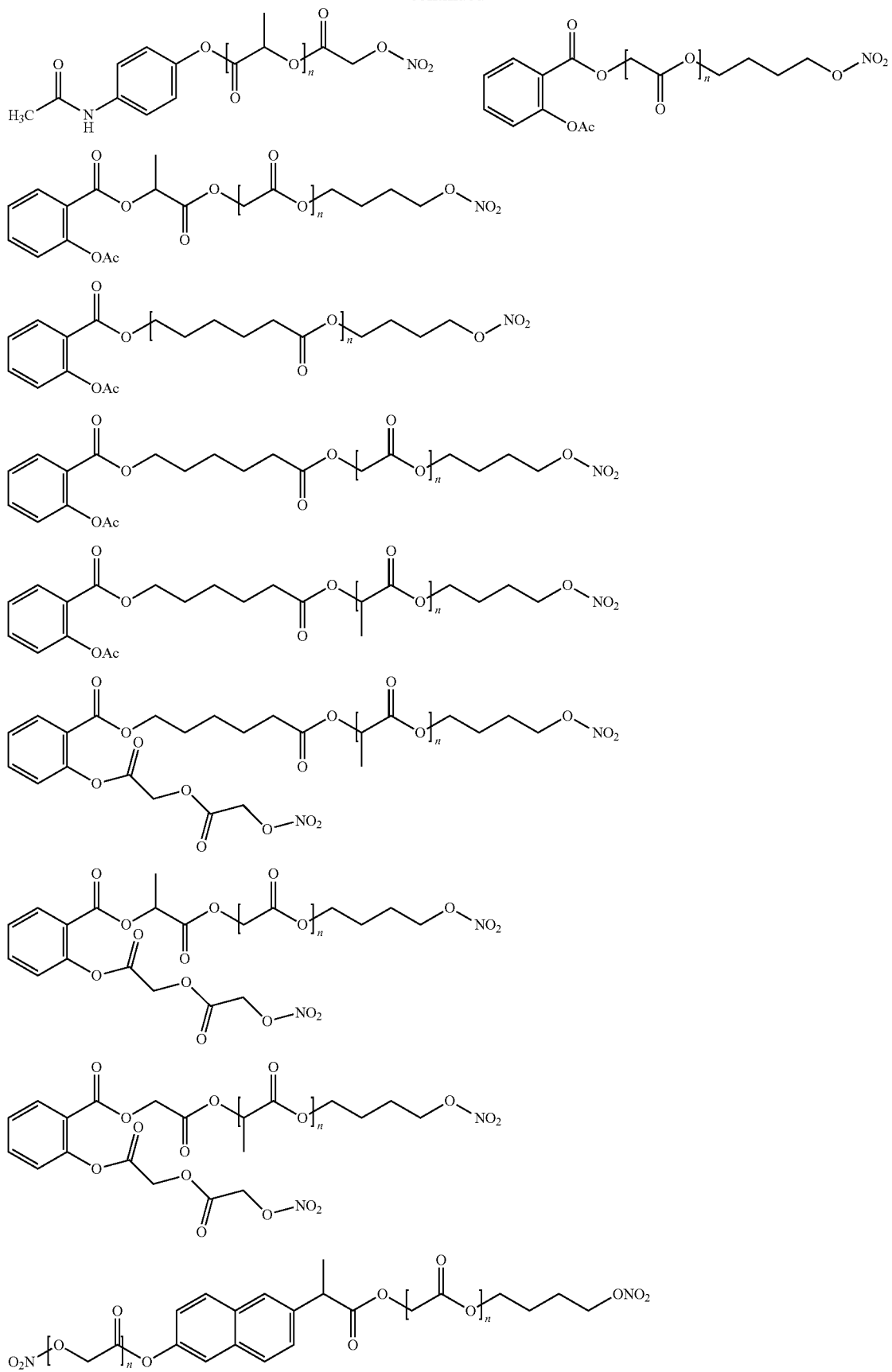

-continued
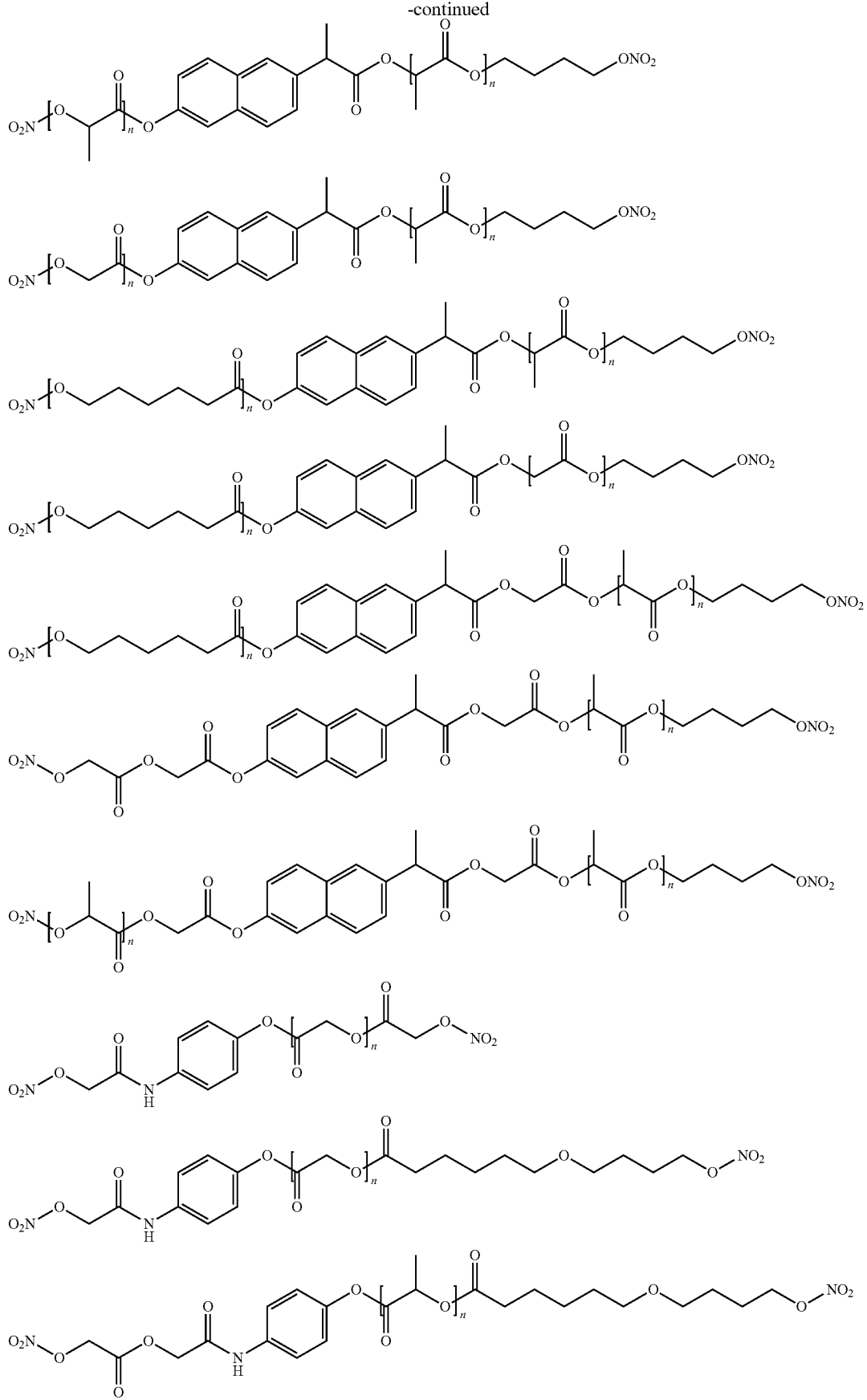

-continued
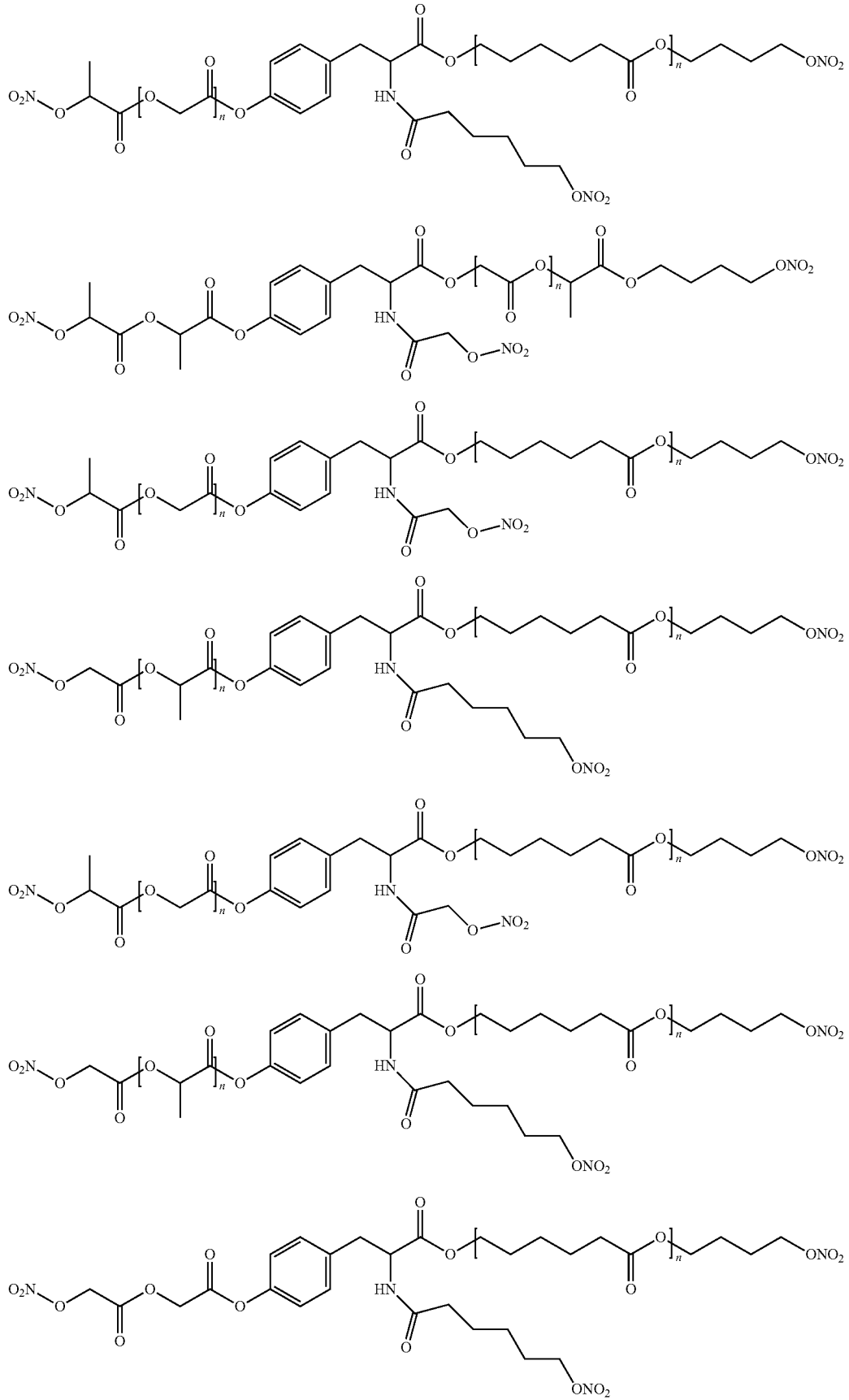

-continued
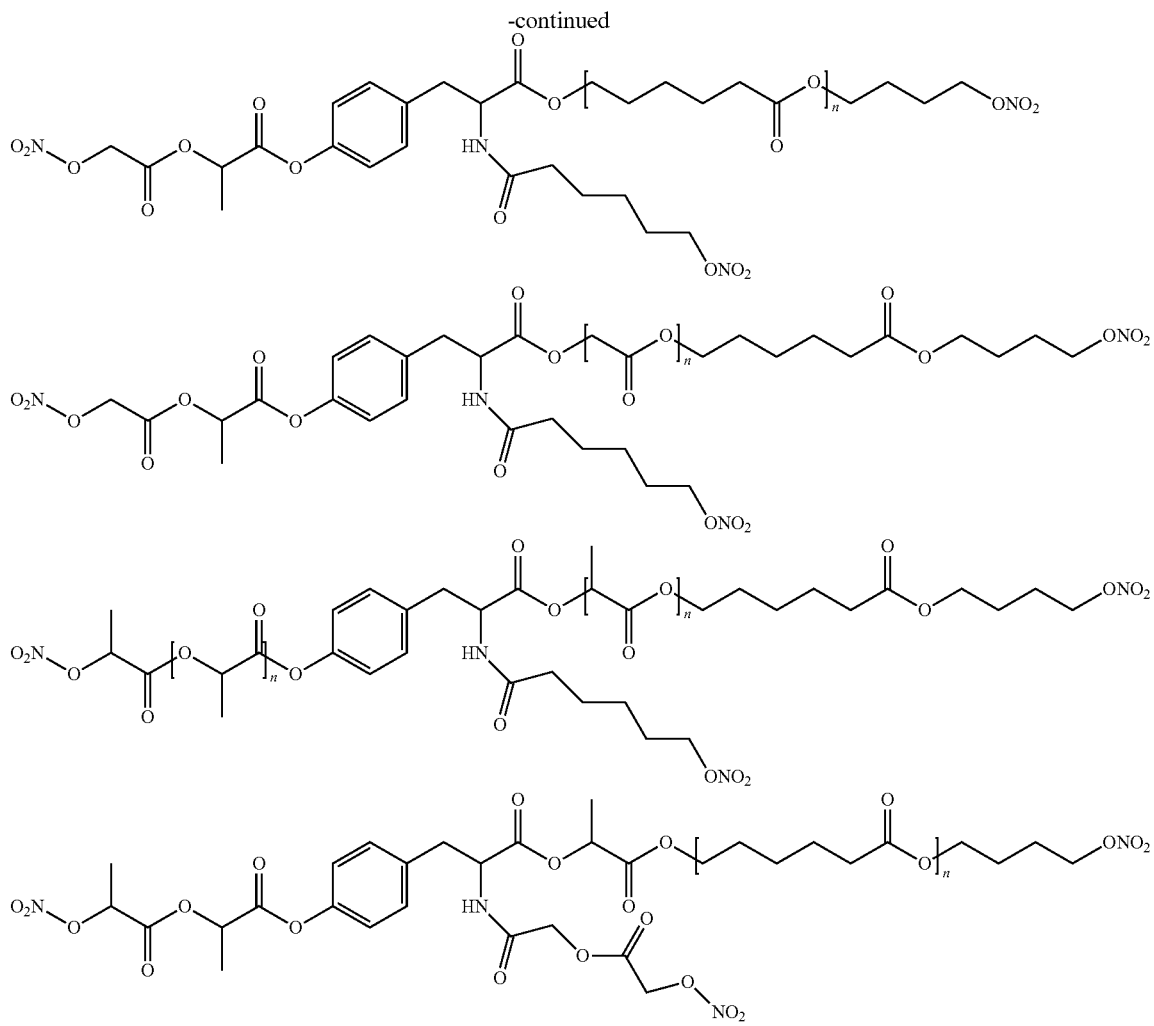
The present invention also provides NO and drug releasing macromers and oligomers wherein D is according to (ii), such as the macromers or oligomers where D is a di-, tri- or quadra-acyl moiety. For example the macromer or oligomer can be selected from the following formulas:
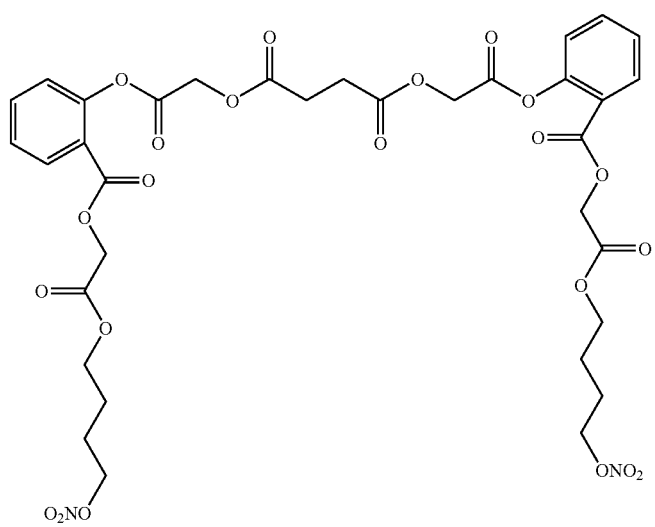

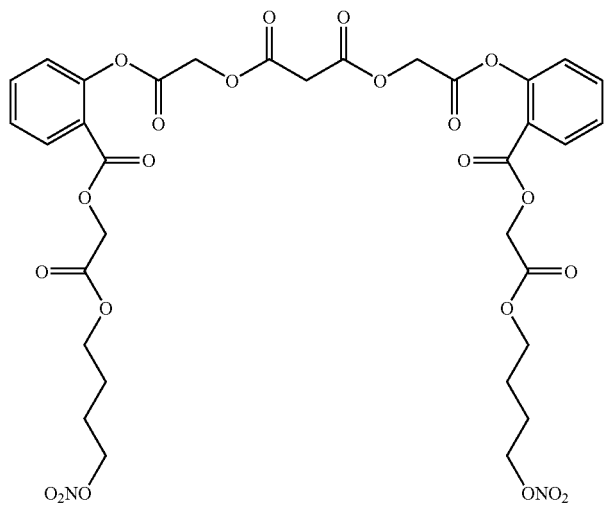
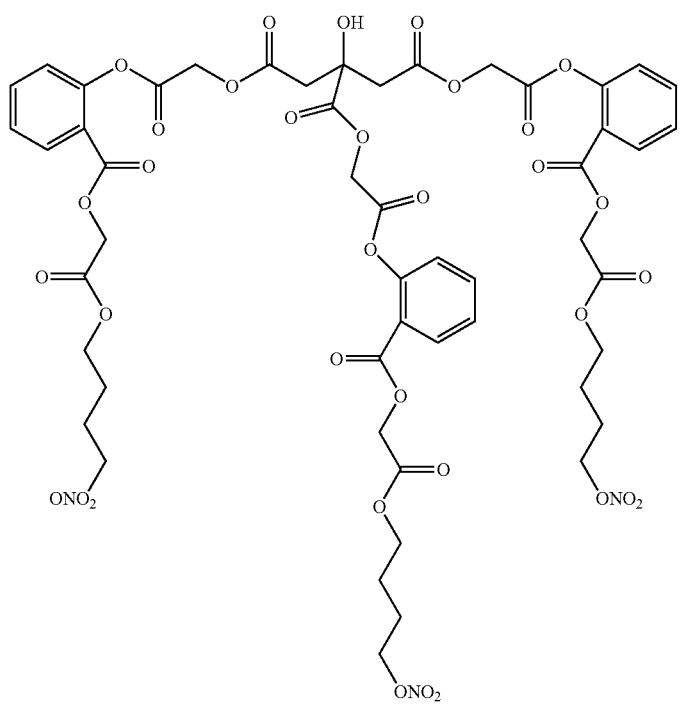
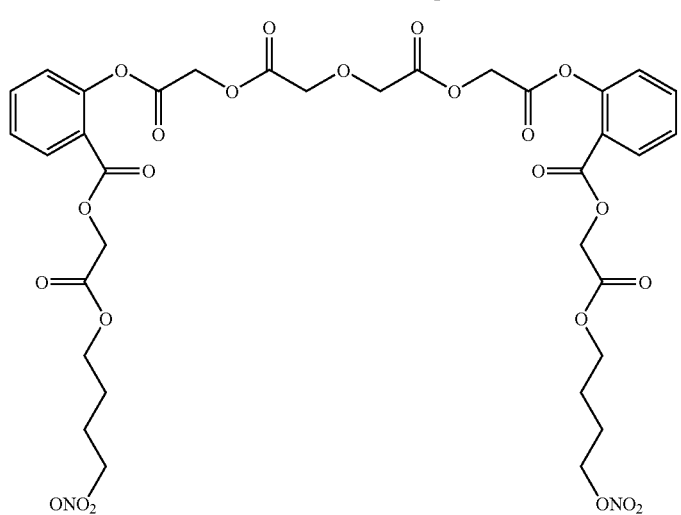

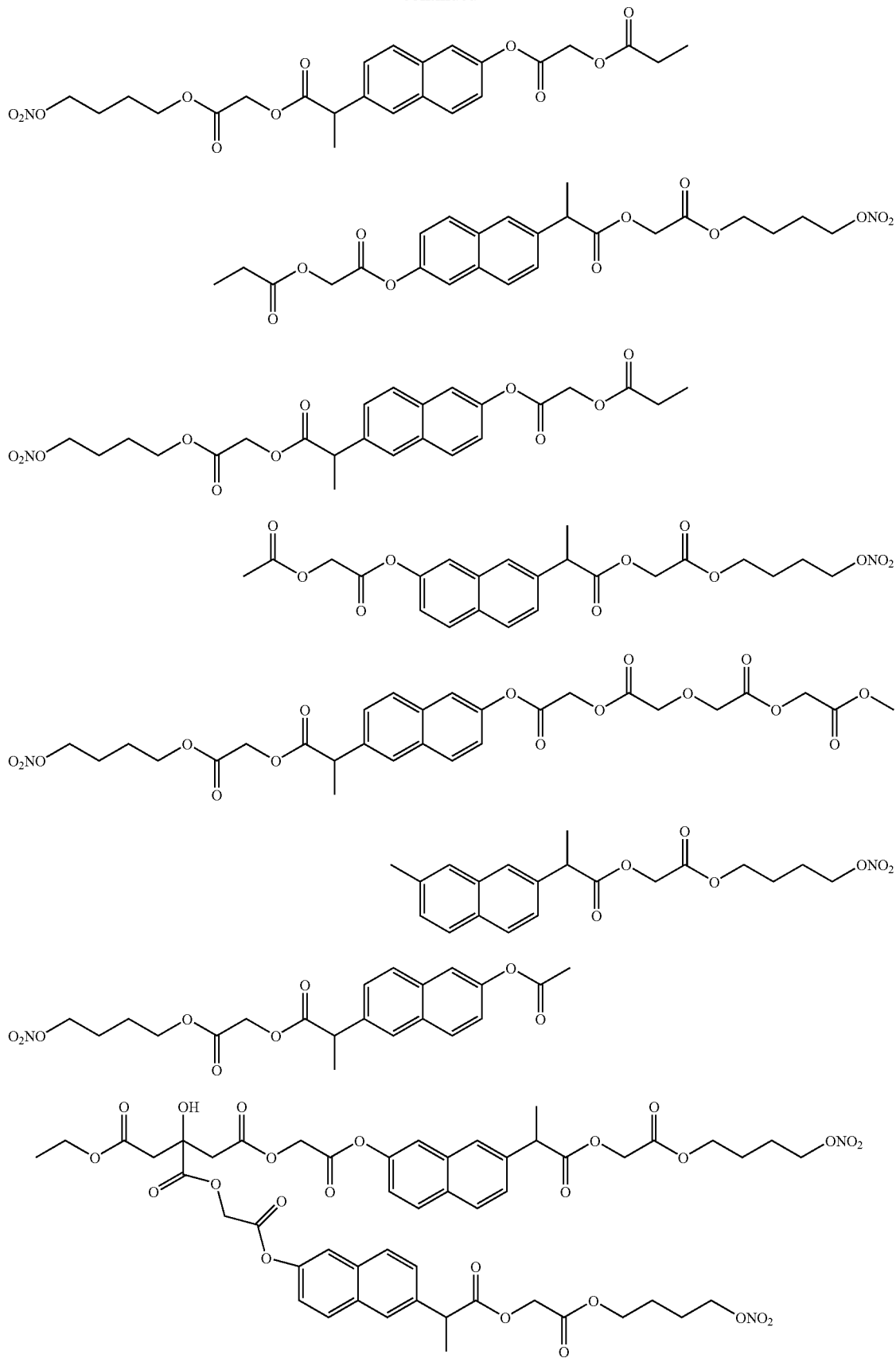

The present invention also provides NO and drug releasing macromers and oligomers wherein two or more drug molecules functionalized with a NO releasing moiety are covalently linked to each other via a hydrolysable macromer or a oligomer.

The present invention also provides NO and drug releasing absorbable or non-absorbable polymers including but not limited to polyesters, polyurethanes, poly(ester-amides) and combinations thereof prepared from macromers or oligomers bearing covalently attached NO and drug releasing pendant groups.

The rate of hydrolysis of the NO and drug releasing macromers and oligomers of the present invention will depend upon a number of factors, including the number of repeat units in the linker as well as by the choice of the safe and biocompatible molecules from which the repeat units are derived. For example, NO and drug releasing macromers and oligomers of the present invention comprising of degradable linker containing repeat units derived from glycolic acid will hydrolyze faster than the one comprising repeat units derived from p-dioxanone. Similarly, NO and drug releasing macromers and oligomers of the present invention comprising of degradable linker containing repeat units derived from lactic acid and caprolactone should take much longer to hydrolyze than the ones wherein the degradable linker comprises of repeat units derived from glycolic acid and dioxanone. Furthermore, it is expected that the rate of hydrolysis will vary with variation in number of repeat units in the degradable linker. Thus, the desired time range may be obtained by altering number of repeat units in the linker as well as by the choice of the safe and biocompatible molecules from which the repeat units are derived.

The NO and drug releasing macromers and oligomers of the present invention, upon contact with body fluids including blood or the like, undergoes gradual degradation (mainly through hydrolysis) with concomitant release of the dispersed drug for a sustained or extended period. This may result in prolonged delivery (e.g., over 1-2,000 hours or 2-800 hours) of effective amounts (e.g., 0.0001 mg/kg/hour to 10 mg/kg/hour) of the drug. This dosage form may be administered as is necessary depending on the subject being treated, the severity of the affliction, and the judgment of the prescribing physician.

As described herein, the NO and drug releasing macromers and oligomers of the present invention are expected to be useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutraceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia retaining patches or meshes; medicated dressings; facial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

In one embodiment, the present invention provides implantable medical devices comprising an effective amount of one or more of the NO and drug releasing macromers and oligomers of the present invention physically admixed with a polymer wherein a polymer can be absorbable or non-absorbable. Absorbable polymers that can be physically admixed with nitric oxide and drug releasing macromers and oligomers of the present invention includes but are not limited to polyesters, poly(lactide-co-glycolide), polycaprolactone, poly(p-dioxanone), polyglycolide, polyoxaesters, poly(esterurethanes), absorbable polyurethanes, poly(esteramides) and combinations thereof. Non-absorbable polymers that can be physically admixed with nitric oxide and drug releasing macromers and oligomers of the present invention includes but are not limited to polyethylene, polypropylene, polyurethanes, polyamides, polyethyleneglycols, polyacrylates, polybutylenes and combinations thereof.

In another embodiment, the present invention provides coating composition for medical devices screw comprising an effective amount of one or more of the NO and drug releasing macromers and oligomers of the present invention physically admixed with a polymer wherein a polymer can be absorbable or non-absorbable.

Thus, the present invention provides at least two ways of enhancing the biocompatibility of the medical device and/or providing for in-situ controlled release of NO and drug at the treatment site.

Exemplary embodiments of implantable medical devices and coatings comprising of NO and drug releasing macromers and oligomers of the present invention include, but are not limited to cardiovascular drug-eluting stents, diagnostic catheters, guide wires, guide catheters, PTCA balloon catheters (for percutaneous transluminal coronary angioplasty) in blood vessels, in-dwelling sheaths (venous and arterial), intraaortic balloon pump catheters, intravascular sensors, extracorporeal blood loop circuits, intravenous grafts/shunts and adhesion prevention barriers including meshes and coatings therefore wherein NO and drug are released in-situ such that the indication sought to be treated (e.g., restenosis) is treated, prevented, inhibited or ameliorated.

For coating applications, the polymer comprising the coating composition can usefully exhibit an inherent viscosity, as measured in a 0.1 gram per deciliter (g/dl) of hexafluoroisopropanol (HFIP), of, for example, between about 0.05-2.0 dl/g or about 0.10-0.80 dl/g. If the inherent viscosity is too low, then the polymer may not have the integrity necessary for the preparation of films or coatings for the surfaces of various surgical and medical articles. Polymers with an inherent viscosity greater than about 2.0 dl/g can be used, though in many cases it may be difficult to do so.

The amount of coating to be applied on the surface of a braided suture can be readily determined empirically, and will depend on the particular copolymer comprising the composition and suture chosen. In certain embodiments, the amount of coating applied to the surface of the suture may range from about 0.5-30 percent of the weight of the coated suture or from about 1.0-20 weight percent, or from 1-5 percent by weight. If the amount of coating on the suture were too great, then there may be an increased risk that the coating may flake off when the suture is passed through tissue When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater too great, or if the thickness was too low, then the desired performance of the stent as it is passed through tissue may not be optimal.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was too great, or if the thickness was too low, then the desired performance of the needle as it is passed through tissue may not be optimal.

In another embodiment, present invention also provides a drug delivery system, comprising: an effective amount of one or more of the NO and, optionally, drug releasing macromers and oligomers of the present invention physically admixed, embedded or dispersed into the absorbable or non-absorbable polymer and the polymer is in the form of a polymeric matrix.

In still another embodiment, the present invention provides an anti-inflammatory or anti-oxidant or antimicrobial or a pharmaceutical composition comprising an effective amount of one or more of the NO and, optionally, drug releasing macromers and oligomers of the present invention wherein said composition is in a form suitable for oral, enteral, parenteral, topical, transdermal, ocular, vitreal, rectal, nasal, pulmonary, or vaginal administration.

The most suitable route in any given case will depend on the nature and severity of the condition being treated and on the nature of the particular active compound that is being used. The NO and drug releasing formulations of a pharmaceutical composition are typically admixed with one or more pharmaceutically or veterinarially acceptable carriers and/or excipients as are well known in the art.

NO and, optionally, drug releasing formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; as an oil-in-water or water-in-oil emulsion; or the like NO and, optionally, drug releasing compositions of the present invention suitable for parenteral administration conveniently comprise sterile aqueous preparations of the NO releasing active compounds, which preparations are preferably isotonic with the blood of the intended recipient.

NO and, optionally, drug releasing formulations suitable for rectal administration are preferably presented as unit dose suppositories.

NO and, optionally, drug releasing formulations suitable for ocular or vitreal administration may be presented as NO and drug releasing bioabsorbable coatings for implantable medical devices, injectables, liquids, gels, suspensions, or the like.

NO and, optionally, drug releasing formulations or compositions suitable for topical administration to the skin preferably take the form of an ointment, cream, lotion, paste, gel, spray, aerosol, oil, or the like. Examples of carriers that conventionally used include Vaseline, lanoline, polyethylene glycols, alcohols, and combination of two or more thereof.

NO and, optionally, drug releasing formulations suitable for transdermal administration may be presented as discrete patches adapted to remain in intimate contact with the epidermis of the recipient for a prolonged period of time.

The NO and, optionally, drug releasing macromers and oligomers of the present invention may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, and the like. Food formulations containing compounds of the invention can be readily prepared according to standard practices.

NO and, optionally, drug releasing macromers and oligomers of the present invention used as medicaments or pharmaceuticals are typically administered in a manner and amount as is conventionally practiced. See, for example, Goodman and Gilman, The Pharmaceutical Basis of Therapeutics, 11$^{th}$ Edition.

NO and, optionally, drug releasing macromers and oligomers of the present invention may have potent antioxidant activity and increased acidity of their aromatic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

The present invention also provides a nitric oxide and, optionally, drug releasing pharmaceutical composition comprising a nitric oxide and, optionally, drug releasing macromers and oligomers of the invention and a second therapeutic agent that is physically admixed, embedded or dispersed within the polymer matrix of an absorbable or non-absorbable polymer. The invention also provides a NO releasing pharmaceutical composition comprising a polymer of the invention having a second therapeutic agent appended to the polymer (e.g. with bonds that will hydrolyze to release the second therapeutic agent under physiological conditions).

Dosages

Useful dosages of the NO and, optionally, drug releasing macromers and oligomers of the present invention can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of NO and, optionally, drug releasing macromers and oligomers required for use in treatment will vary not only with the particular molecule selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

In yet another embodiment, the present invention provides a method for the treatment of diseases including but not limited to cancer and cardiovascular diseases which comprise administering to a subject in need thereof by means of controlled drug delivery a therapeutically effective amount of one or more of the NO and, optionally, drug releasing macromers and oligomers of the present invention.

The quantity and type of NO and, optionally, drug releasing macromers and oligomers incorporated into a composition comprising the medical device, medical device coating, drug delivery system, pharmaceutical, anti-inflammatory, antioxidative and antimicrobial formulations will vary depending on the rate and extent of release profile desired, amount of NO and, optionally, drug releasing macromers and oligomers employed and the therapeutic effect desired. The product may contain blends of NO and, optionally, drug releasing macromers and oligomers of the present invention to provide the desired release profile or consistency to a given formulation.
Biologically Active Substances and Combination Therapies The nitric oxide and, optionally, drug releasing macromers and oligomers of the present invention can also be administered in combination with other therapeutic agents that are effective to treat a given condition to provide a combination therapy. Thus, the invention also provides a method for treating a disease in a mammal comprising administering an effective amount of a combination of a nitric oxide and drug releasing macromers and oligomers of the invention and another therapeutic agent. The invention also provides a nitric oxide and drug releasing pharmaceutical composition comprising a nitric oxide and drug releasing macromers and oligomers of the invention, another therapeutic agent, and a pharmaceutically acceptable carrier.

The NO and, optionally, drug releasing macromers and oligomers of the present invention are also useful for administering a combination of therapeutic agents to an animal. Such a combination therapy can be carried out in the following ways: 1) another therapeutic agent can be physically admixed, dispersed or embedded within the polymer matrix of a absorbable polymer, and can be released upon degradation of the polymer; 2) another therapeutic agent can be appended to an absorbable polymer with bonds that hydrolyze to release the therapeutic agent and NO under physiological conditions.

Another aspect of the invention provides a method by which NO and, optionally, drug releasing macromers and oligomers are prepared. The method involves the attachment of NO releasing moiety to a drug molecule functionalized with a hydrolysable linker moiety. The resultant NO releasing functionalized drug molecules are more hydrolysable and biodegradable than the pre-functionalized drug molecule, and provides controlled release of the biologically active component and NO over a time period from several weeks to four years, depending on the number of factors including the number of repeat units in the linker as well as by the choice of the safe and biocompatible molecules from which the repeat units are derived.

Biologically active hydroxy compounds that can be used to prepare NO and drug releasing macromers and oligomers of the present invention include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochloride, ketobemidone, khellin, labetalol, lactylphenetidin, levodopa. levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, .alpha.-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Other bioactive phenolics that can be used include acacetin, 4-acetamido-2-methyl-1-naphthol, acet-aminophen, albuterol, allenolic acid, aloe emodin, aloin, β-amino-4-hydroxy-3,5-di-iodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromo-nar, chrysin, cinametic acid, clorophene, coniferyl alcohol, p-coumaric acid, coumes-trol, coumetarol, daphnetin, datiscetin, deoxyepinephrine, 3,5-diiodothyronine, 3,5-di-iodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophe-none, gallic acid, gardenins, genistein, gentisyl alcohol, gepefrine, geranylhydroqui-none, [6]-gingerol, gossypol, guaiacol, guaifenesin, harmalol, hematoxylin, hinderin, homoeriodictyol, homogentisic acid, homovanillic acid, hydroxyamphetamine, 2-hyd-roxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxy-phenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl)methylenepropanedinitrile, thymol, thyropropic acid, thyroxine, tiratricol, tyrosine, vanillic acid, and vanillin.

Further biologically active carboxylic acid and/or amine compounds that can be used to prepare a NO and drug releasing macromers and oligomers of the present invention include Acemetacin, Aceclofenac, Acediasulfone, Adipiodone, Alminoprofen, Amisulpride, Amlexanox, Amodiaquine, Amosulalol, Amoxicillin, Amsacrine, Anileridine, Azacyclonol, Baccofen, Balsalazide sodium, Bentiromide, Benzocaine, Bromopride, Bumetanide, Carprofen, Carvedilol, Carzenide, Cefprozil, Cinitapride, Cinmetacin, Clebopride, Clenbuterol, Clometacin, Cromoglicic acid, Diclofenac, Diflunisal, Eprosartan, Ethoxzolamide, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic acid, Mefenamic acid, Nadoxolol, Naproxen, Nedocromil, D-Norpseudoephedrine, paracetamol Repaglinide, Salazosulfapyridine, Salicylic Acid, Salsalate and Sarpogrelate.

In a further aspect of the present invention one can blend two or more of the NO and drug releasing macromers and oligomers of the present invention.

Examples of biologically active dihydroxy compound that can be used to prepare NO and drug releasing macromers and oligomers of the present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active diamino compounds that can be used to prepare macromers/oligomers of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, and D-Norpseudoephedrine.

Examples of biologically active hydroxy/amino compounds that can be used to prepare macromers and oligomers of the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, and paracetamol.

Examples of biologically active dicarboxylic acid compounds that can be used to prepare macromers and oligomers of the present invention include Adipiodone, Cromoglicic acid, Eprosartan, Iocarmic acid, Iodoxamic acid, Ioglycamic acid, Iotroxic acid, Nedocromil.

Examples of biologically active hydroxy/carboxylic acid compounds that can be used to prepare macromers and oligomers of the present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids useful in the present invention include 4-hydroxycinnamic acid, caffeic acid, chlorogenic acid, ferulic acid, sinapic acid, vanillic acid, Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active amino/carboxylic acid compounds that can be used to prepare macromers and oligomers of the present invention include Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Examples of biologically active diamino compounds useful in the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, amino acids (L-lysine), and natural products.

Examples of naturally occurring biologically active phenolics include bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, synapic acid, vanillic acid, vanillin, chalcones, soybean flavonoids and derivatives thereof.

Capsaicin is a biologically active phenolic that is the active component of cayenne pepper. The capsaicin is an amide of vanillylamine and $C_8$ to $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4× daily may help peripheral neuropathic pain, post-herpetic neuralgia, trigeminal neuralgia, psoriasis and fibromyalgia. It is also useful for diabetic neuropathy, cluster headaches, earache, osteo- and rheumatoid arthritis. Capsaicin is a powerful pain reliever.

Naproxen, paracetamol, acetaminophen and acetylsalicylic acid are biologically active phenolics that belong to the class of drugs called non-steroidal anti-inflammatory drugs or NSAIDs. The NSAIDs provide relief by blocking the action of prostaglandins, which are hormone-like substances that contribute to pain, inflammation, fever and muscle cramps. Phenolic moieties, synthetic and naturally occurring, are part of many drugs.

Pendant Polymers, Misc.

Where D is according to (iii), the macromers or oligomers can be termed "pendant polymers." These comprise polymers having pendant groups modified to have NO producing groups, or bioactive agents and NO producing groups. These are often formed from monomers having NO-releasing and/or biologically active agent-releasing moieties. Modification of polymers to provide NO-releasing and/or biologically active agent-releasing moieties can also be conducted, in many cases through the use of appropriate protective groups for the pendant functionality used to attach NO-releasing and/or biologically active agent-releasing moieties.

Monomers having NO-releasing and/or biologically active agent-releasing moieties that can be used to form the pendant polymers of the present invention include but are not limited to those according to formulas B and C (above). In Formulas B and C, the terms L, L', L", P, P', D' and R' independently have the same meaning as set forth above, and r is an integer equal to 1 or 2. E is a moiety consisting of C, H, O, S or N, predominantly of composed of C and H. E can have a molecular weight of 600 or less, or 500 or less, or 400 or less, or 300 or less. A and B are independently —OH, —NH$_2$ or —CO$_2$H. (An acid or base form written anywhere in this specification also encompasses salts thereof.) All appropriate subdefinitions of L, L', L", P, P', D' and R' set forth above apply to these terms as used with the monomer formulas A and B. In other words, all embodiments of Formula A that can logically be applied to Formulas B and C are contemplated as part of the invention.

E can substantially comprise a hydrocarbon, with a trivalent or quaternary carbon directly linked by linkages comprising covalent bonds and, in most linkages, carbon to more reactive nitrogen, carbonyl or oxygen functionalities of A, B and L. In some embodiments, the linkages from the trivalent or quaternary carbon to the nitrogen, carbonyl or oxygen functionalities of A, B and L are alkyl.

Examples of such monomers include, without limitation:

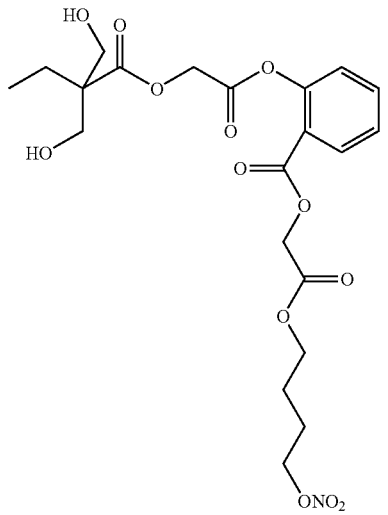

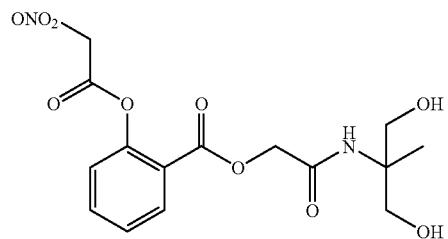

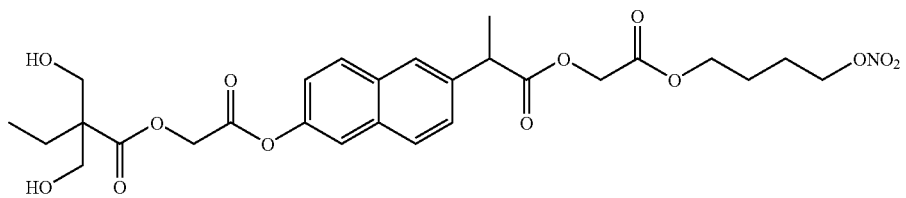

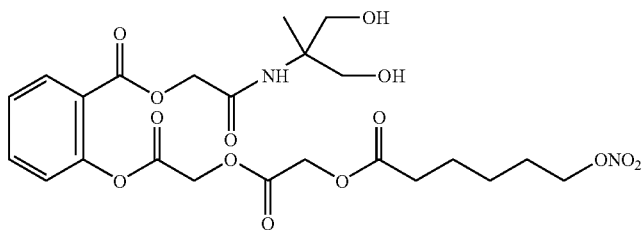

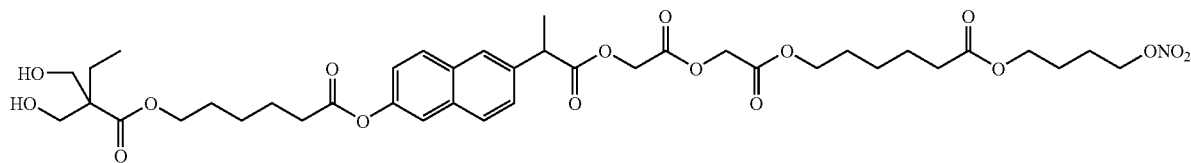

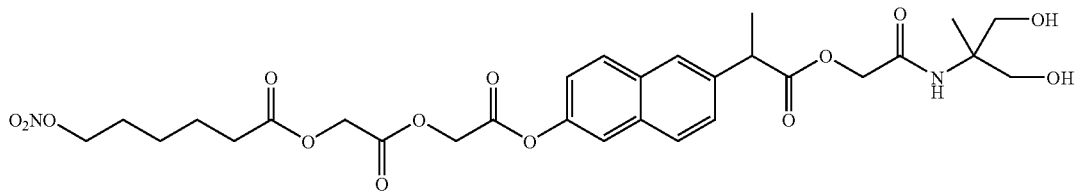

-continued

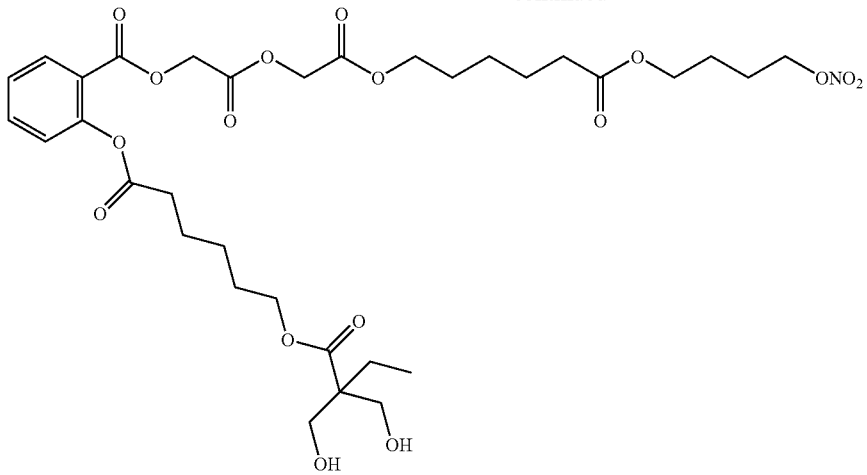

These diol monomers having the NO-releasing and/or biologically active agent-releasing moieties can be reacted with acid terminated polyesters to form pendant polyesters, can be reacted with isocyanate terminated polyurethanes to form pendant polyurethanes, can be reacted with acid terminated polyester urethanes to form pendant polyester urethanes. In addition, these diol monomers having the NO-releasing and/or biologically active agent-releasing moieties can be reacted with acids including diacids, isocyanates including diisocyanates and lactones including substituted lactones to form polyesters and polyurethanes bearing pendant NO-releasing and/or biologically active agent-releasing moieties along the chain.

The D moiety is substantially exemplified by biologically active agents. These agents well exemplify the kinds of functionalities that can be used to make the macromers and oligomers of formula I.

The repeats that are polyester polymerization compatible—i.e., those derived from monomers that can be serially attached to, or co-polymerized with, the monomers giving rise to the Group A repeats. These will be recognized by those of skill in the art, and include, for example, diacids, diamines, diisocyanates and the like.

The macromer or oligomer is preferably applied in an effective amount. If it release NO as an active, NO is preferably released as an effective amount. If, in addition, a biologically active species is released, such is preferably released as an effective amount. To treat the indications of the invention, an effective amount of a pharmaceutical compound will be recognized by clinicians but includes an amount effective to treat, reduce, ameliorate, eliminate or prevent one or more symptoms of the disease sought to be treated or the condition sought to be avoided or treated, or to otherwise produce a clinically recognizable favorable change in the pathology of the disease or condition.

Applicant provides herein below claims to (a) macromer or oligomer, (b) compositions thereof, (c) medical devices thereof and (d) methods of treatment therewith. The invention includes combination of the macromer/oligomer claims that are not logically precluded. The invention includes group (b), (c) or (d) claims as written to depend on any of the combinations of the macromer/oligomer claims discussed above, and any combination of the claims of such groups (not logically precluded) as written to depend on any of the combinations of the macromer/oligomer claims discussed above.

In Formulas A and B, the entire structures can be regarded as the monomer (for building a polyester, polyether, mixed polyester/polyether, polyurethane or polyester polyurethane polymer), or the elements (A)(B)EL can be regarded as the monomer. Both terminologies are used herein, but the context makes the intended meaning clear.

In certain embodiments, the non-hydrocarbon functionalities in the monomer, aside from D where D is a bioactive substance, comprise ether, ester, amide, halo, hydroxy and nitric oxide.

The chemistry illustrated below makes use of appropriate protecting groups to accommodate the various functionalities present. These protection group strategies are well known for the amine, carboxylic, hydroxy and halo functionalities needed to practice the invention.

The definitions and examples provided in this application are not intended to be limiting, unless specifically stated. Furthermore, examples of nitric oxide and drug releasing macromers and oligomers of the present invention are provided for some embodiments of the current invention. It can be extended to other species. This selection is not meant to limit the scope of the invention in any way. Other variations in the procedure may be readily apparent to those skilled in the art.

Example 1

Synthesis of 2-(6-methoxy-naphthalen-2-yl)-propionic acid benzyloxy-carbonyl methyl ester

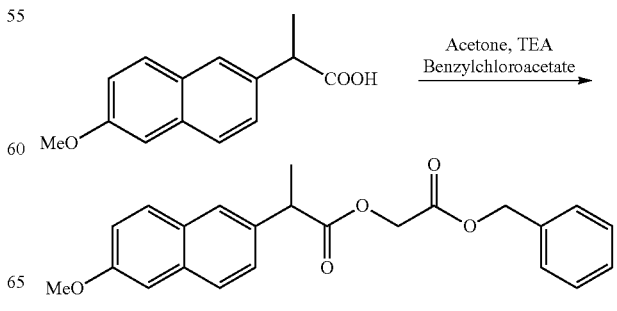

To a mixture of Naproxen (25 grams) and triethylamine (23 ml) in acetone (150 ml) was added benzyl chloroacetate (24 grams) drop wise, and the mixture was stirred at 50° C. temperature for three hours. The reaction mixture was poured onto cold water, and crude 2-(6-Methoxy-naphthalen-2-yl)-propionic acid benzyloxy-carbonyl methyl ester was filtered, dried and purified by recrystallizing from a mixture of ethyl acetate:hexane to give pure 2-(6-Methoxy-naphthalen-2-yl)-propionic acid benzyloxycarbonyl methyl ester (39 grams) as a white powder. m.p: 95.3-97.3° C. The pure product was characterized using $^1$H NMR spectroscopy in CDCl$_3$: δ 1.60 (d, 3H, CH$_3$), 3.80 (m, 4H, CH and OCH$_3$), 4.56 (q, 2H, OCH2), 5.12 (q, 2H, OCH2), 7.06 (m, 2H, Ar), 7.30 (m, 6H, Ar), 7.64 (m, 3H, Ar)

Example 2

Synthesis of 2-(6-methoxy-naphthalen-2-yl)-propionic acid carboxymethyl ester

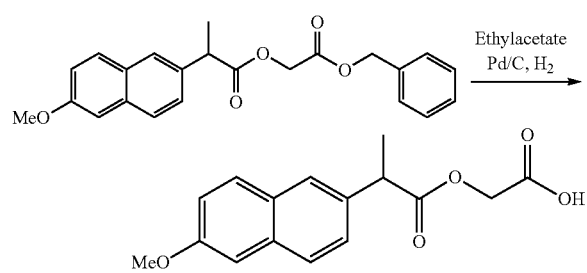

To a solution of 2-(6-methoxy-naphthalen-2-yl)-propionic acid benzyloxy carbonyl methyl ester (45 grams) in ethyl acetate (200 ml), was added 50% wet Palladium on carbon (10%, 9 grams), and the mixture was stirred under an atmosphere of hydrogen (4 Kg) overnight in a pressure vessel. The catalyst was removed by filtration and ethyl acetate was distilled under vacuum. The crude product was precipitated by adding hexane, filtered, dried, and purified by recrystallization in a mixture of ethyl acetate:hexane to get pure 2-(6-Methoxy-naphthalen-2-yl)-propionic acid carboxymethyl ester (30 grams) as a white powder with a melting point of 131-132.5° C. The pure product was characterized using $^1$H NMR spectroscopy in CDCl$_3$: $^1$H NMR (CDCl$_3$) δ 1.60 (d, 3H, CH$_3$), 3.88 (s, 1H, OCH$_3$), 3.94 (m, 1H, CH), 4.54 (q, 2H, OCH2), 7.06 (m, 2H, Ar), 7.39 (d, 1H, Ar), 7.64 (m, 3H, Ar).

Example 3

Synthesis of 2-(6-methoxy-naphthalen-2-yl)-propionic acid 4-bromo-butoxy carbonyl methyl ester

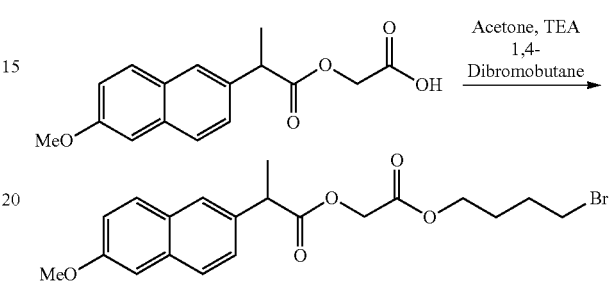

To a mixture of 2-(6-Methoxy-naphthalen-2-yl)-propionic acid carboxymethyl ester (30 grams) and triethylamine (21.9 ml) in acetone (200 ml) was added 1,4-dibromobutane (90 grams) drop wise, and the mixture stirred at room temperature for 24 hours. The reaction mixture was poured onto cold water, and crude 2-(6-Methoxy-naphthalen-2-yl)-propionic acid 4-bromo-butoxy carbonyl methyl ester was extracted into dichloromethane. After drying over sodium sulphate, dichloromethane was distilled off under reduced pressure, and the residue was purified by column chromatography using hexane as an eluant to get 18 grams of 2-(6-Methoxy-naphthalen-2-yl)-propionic acid 4-bromo-butoxy carbonyl methyl ester as light brown syrup. The pure product was characterized using $^1$H NMR spectroscopy in CDCl$_3$: δ 1.52 (d, 3H, CH$_3$), 1.62 (m, 4H, CH$_2$X$_2$), 3.16 (t, 2H, CH$_2$), 3.82 (m, 4H, CH and OCH$_3$), 3.98 (t, 2H, CH$_2$), 4.46 (q, 2H, OCH2), 7.00 (m, 2H, Ar), 7.30 (d, 1H, Ar), 7.58 (m, 3H, Ar).

Example 4

Synthesis of 2-(6-methoxy-naphthalen-2-yl)-propionic acid 3-nitrooxy-propoxy carbonyl methyl ester To a solution of 2-(6-Methoxy-naphthalen-2-yl)-propionic acid 4-bromo-butoxy carbonyl methyl ester (15 grams) in acetonitrile (150 ml) was added Silver nitrate (8.7 grams), and the mixture was left for stirring with reflux overnight. The reaction mixture was filtered and washed with acetonitrile, dried over sodium sulphate, the solvent distilled off under reduced pressure, and the residue was purified by column chromatography using hexane:ethyl acetate as eluant to get 13 grams of 2-(6-Methoxy-naphthalen-2-yl)-propionic acid 3-nitrooxy-propoxy carbonyl methyl ester as a light yellow syrup. The pure product was also characterized using $^1$H NMR spectroscopy in CDCl$_3$: δ 1.62 (m, 7H, CH$_2$X$_2$ and CH$_3$), 3.92 (s, 3H, OCH$_3$), 3.97 (q, 1H, CH), 4.12 (t, 2H, CH$_2$), 4.32 (t, 2H, CH$_2$), 4.61 (s, 2H, OCH2), 7.16 (m, 2H, Ar), 7.43 (d, 1H, Ar), 7.73 (m, 3H, Ar)

Example 5

Synthesis of 2-(6-hydroxy-naphthalen-2-yl)-propionic acid

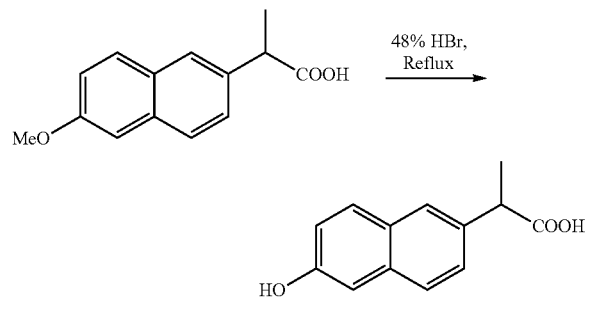

A mixture of Naproxen (500 grams) and 48% HBr solution (1500 ml) was refluxed for 10 Hours, poured onto ice water (3000 ml), and stirred for 30 minutes. Crude 2-(6-hydroxy-naphthalen-2-yl)-propionic acid was filtered, dried and recrystallised from a mixture of ethyl acetate and hexane to give pure 2-(6-hydroxy-naphthalen-2-yl)-propionic acid (380 grams, 81%) as a white powder with a melting point of 186-188° C.

Example 6

Synthesis of 2-(6-Hydroxy-naphthalen-2-yl)-propionic acid methyl ester

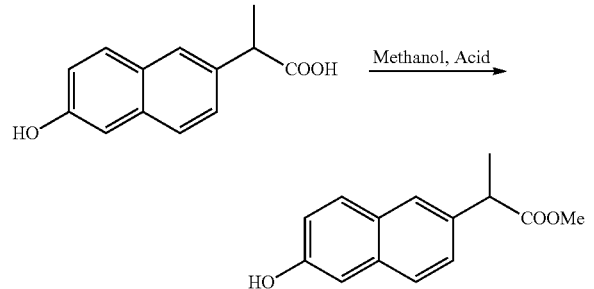

To a solution of methanol (2100 ml) and sulphuric acid (84 ml) was added 2-(6-Hydroxy-naphthalen-2-yl)-propionic acid (420 grams). The reaction mixture was refluxed for 6 Hours. Methanol (1000 ml) was distilled, and the cooled reaction mass was poured onto ice water to yield crude 2-(6-hydroxy-naphthalen-2-yl)-propionic acid methyl ester which was filtered, dried and recrystallized using a mixture of ethyl acetate:hexane to yield pure product (400 grams, 89.5% yield) as a white fluffy powder with a melting point of 89.5-92° C. The pure product was characterized using $^1$H NMR spectroscopy in CDCl$_3$ δ 1.60 (d, 3H, CH$_3$), 3.70 (s, 3H, Ester), 3.88 (q, 1H, CH), 5.36 (bs, 1H, OH), 7.08 (m, 2H, Ar), 7.48 (m, 1H, Ar), 7.65 (m, 3H, Ar).

Example 7

Synthesis of 2-[6-(2-chloro-acetoxy)-naphthalen-2-yl]-propionic acid methyl ester

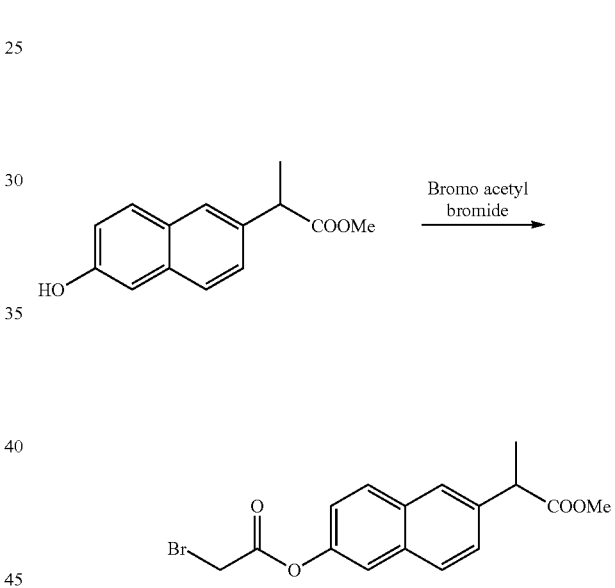

To a solution of 2-(6-hydroxy-naphthalen-2-yl)-propionic acid methyl ester (20 grams) and pyridine (10.3 grams) in dichloromethane (200 ml) maintained at 0-5° C. under N$_2$ atmosphere was added dropwise bromoacetyl chloride (19.6 grams). The reaction was stirred at the same temperature for one hour. The reaction mixture was washed with water (500 ml) and 5% solution of sodium carbonate followed by drying over sodium sulphate and distillation to get crude compound, which was purified by column chromatography using hexane as eluant to get pure 2-[6-(2-bromo-acetoxy)-naphthalen-2-yl]-propionic acid methyl ester (14 grams) as a dark brown syrup. The pure product was characterized using $^1$H NMR spectroscopy in CDCl$_3$ δ 1.55 (d, 3H, CH$_3$), 3.65 (s, 3H, Ester), 3.82 (q, 1H, CH), 4.08 (s, 2H, OCH$_2$) 7.20 (dd, 1H, Ar), 7.4 (dd, 1H, Ar), 7.57 (d, 1H, Ar), 7.72 (d, 1H, Ar), 7.78 (d, 1H, Ar), 7.84 (d, 1H, Ar).

Example 8

Synthesis of 2-[6-(2-nitrooxy-acetoxy)-naphthalen-2-yl]-propionic acid methyl ester

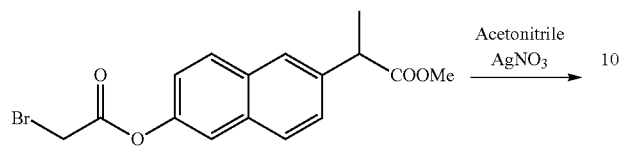

To a solution of 2-[6-(2-bromo-acetoxy)-naphthalen-2-yl]-propionic acid methyl ester (14 grams) in acetonitrile (150 ml) was added silver nitrate (20.2 grams). The solution was stirred at room temperature overnight followed by stirring at 45-50° C. for 4-6 hrs. The reaction mixture was filtered and washed with acetonitrile, dried over sodium sulphate, and the solvent was distilled off under reduced pressure. The residue was purified by column chromatography using a mixture of Hexane:Ethyl acetate as eluant, followed by recrystallisation from a mixture of toluene:hexane to get 5.5 grams 2-[6-(2-Nitrooxy-acetoxy)-naphthalen-2-yl]-propionic acid methyl ester as off white powder. The pure product was characterized using $^1$H NMR spectroscopy in $CDCl_3$ $\delta$ 1.56 (d, 3H, $CH_3$), 3.65 (s, 3H, Ester), 3.90 (q, 1H, CH), 5.258 (s, 2H, $OCH_2$) 7.20 (dd, 1H, Ar), 7.4 (dd, 1H, Ar), 7.57 (d, 1H, Ar), 7.72 (d, 1H, Ar), 7.78 (d, 1H, Ar), 7.84 (d, 1H, Ar). The pure product has a melting point of 72-74° C.

Example 9

Synthesis of 2-(6-hydroxy-naphthalen-2-yl)-propionic acid

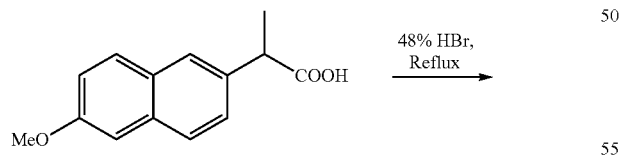

To a mixture of Naproxen (500 grams) and 48% HBr (1500 ml) was refluxed for 10 hours. It was poured onto ice water (3000 ml) and stirred for 30 minutes. Crude 2-(6-Hydroxy-naphthalen-2-yl)-propionic acid was filtered, dried and recrystallized from a mixture of ethyl acetate and hexane to yield pure product (380 grams, 81%) as a white powder with a melting point of 186-188° C.

Example 10

Synthesis of 2-(6-hydroxy-naphthalen-2-yl)-propionic acid benzyloxy carbonyl methyl ester

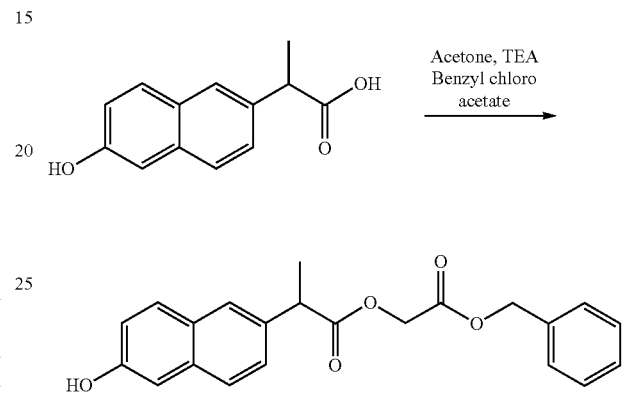

To a mixture of 2-(6-hydroxy-naphthalen-2-yl)-propionic acid (50 grams, 231.48 mmol), triethylamine (33 ml) in acetone (500 ml) was added benzyl chloroacetate (45 grams) drop wise, and the mixture stirred at 50° C. temperature for three hours. The reaction mixture poured onto cold water, crude 2-(6-hydroxy-naphthalen-2-yl)-propionic acid benzyloxy carbonyl methyl ester extracted into ethyl acetate, washed with water, dried over sodium sulphate, the solvent distilled off, and purified by column chromatography with hexane:ethyl acetate as eluant to give pure 2-(6-hydroxy-naphthalen-2-yl)-propionic acid benzyloxy carbonyl methyl ester (41 grams) as a white powder with a melting point of 104-106.5° C. The pure product was characterized using $^1$H NMR spectroscopy in $CDCl_3$ $\delta$ 1.57 (d, 3H, $CH_3$), 3.88 (q, 1H, CH), 4.60 (q, 2H, OCH2), 5.10 (q, 2H, OCH2), 7.04 (m, 2H, Ar), 7.27 (m, 7H, Ar), 7.60 (m, 3H, Ar).

Example 11

Synthesis of 2-(6-hydroxy-naphthalen-2-yl)-propionic acid carboxy methyl ester

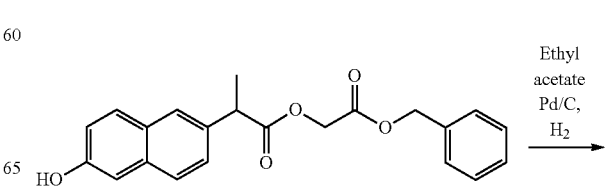

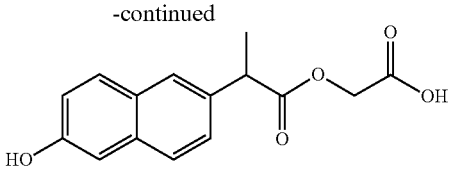

To a solution of 2-(6-Hydroxy-naphthalen-2-yl)-propionic acid benzyloxy carbonyl methyl ester (41 grams) in ethyl acetate (400 ml) in a pressure vessel was added 50% wet palladium on carbon (10%, 9 grams) and the mixture was stirred overnight under an atmosphere of hydrogen (5 Kg) at a temperature of 50° C. The catalyst was removed by filtration and ethyl acetate distilled off (50%) under vacuum, and the product precipitated by adding hexane, filtered and dried to get pure 2-(6-hydroxy-naphthalen-2-yl)-propionic acid carboxy methyl ester (30 grams) as a white powder with a melting point of 186-188.5° C. The pure product was characterized using $^1$H NMR spectroscopy in $CDCl_3$ δ 1.60 (d, 3H, $CH_3$), 3.88 (s, 1H, $OCH_3$), 3.94 (m, 1H, CH), 4.54 (q, 2H, OCH2), 7.06 (m, 2H, Ar), 7.39 (d, 1H, Ar), 7.64 (m, 3H, Ar).

Example 12

Synthesis of 2-(6-hydroxy-naphthalen-2-yl)-propionic acid 4-bromo-butoxy carbonyl methyl ester

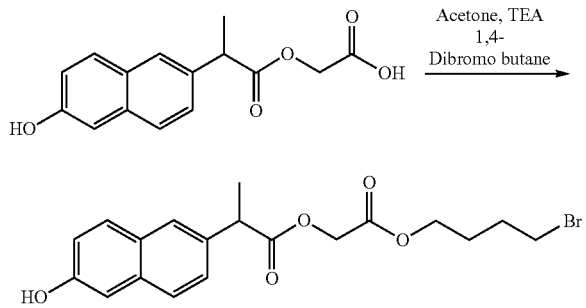

To a mixture of 2-(6-hydroxy-naphthalen-2-yl)-propionic acid carboxy methyl ester (30 grams) and triethylamine (24 ml) in acetone (300 ml) was added dropwise 1,4-dibromo butane (96.5 grams) drop wise followed by stirring at room temperature for 24 hours. The reaction mixture was poured onto cold water, crude 2-(6-hydroxy-naphthalen-2-yl)-propionic acid 4-bromo-butoxy carbonyl methyl ester was extracted into ethyl acetate, and dried over sodium sulphate. Ethyl acetate was distilled off under reduced pressure and the residue was purified by column chromatography using hexane as eluant to yield 24 grams of 2-(6-Hydroxy-naphthalen-2-yl)-propionic acid 4-bromo-butoxy carbonyl methyl ester as a light brown syrup. The pure product was characterized using $^1$H NMR spectroscopy in $CDCl_3$ δ 1.60 (d, 3H, $CH_3$), 1.74 (m, 4H, $CH_2X_2$), 3.22 (t, 2H, $CH_2$), 3.90 (q, 1H, CH), 4.08 (t, 2H, $CH_2$), 4.55 (q, 2H, OCH2), 7.02 (m, 2H, Ar), 7.30 (d, 1H, Ar), 7.58 (m, 3H, Ar)

Example 13

Synthesis of 2-(6-hydroxy-naphthalen-2-yl)-propionic acid 4-bromo-butoxy carbonyl methyl ester

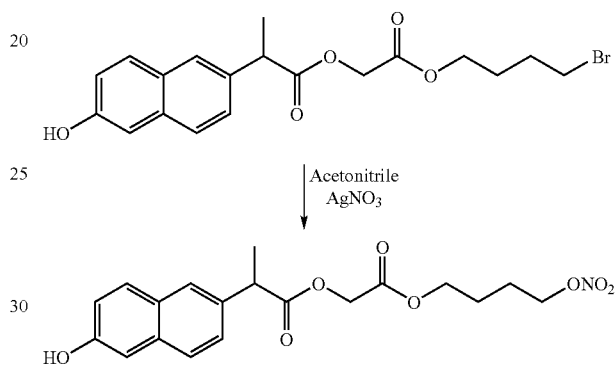

To a solution of 2-(6-hydroxy-naphthalen-2-yl)-propionic acid 4-bromo-butoxy carbonyl methyl ester (20 grams) in acetonitrile (200 ml) was added Silver nitrate (12.4 grams), and the mixture stirred at reflux temperature overnight. The reaction mixture was filtered and washed with acetonitrile, dried over sodium sulphate, the solvent distilled off under reduced pressure, residue re-dissolved in dichloromethane, and the salts filtered off; then the organic layer was washed with water (50 ml), dried over Sodium sulphate, the solvent distilled off under reduced pressure, and the residue was purified by column chromatography using hexane:ethyl acetate as an eluant to get 17 grams of 2-(6-hydroxy-naphthalen-2-yl)-propionic acid 4-nitrooxy-butoxy carbonyl methyl ester white powder.

Example 14

Synthesis of 2-[6-(2-bromo-acetoxy)-naphthalen-2-yl]-propionic acid 4-nitrooxy-butoxy carbonyl methyl ester

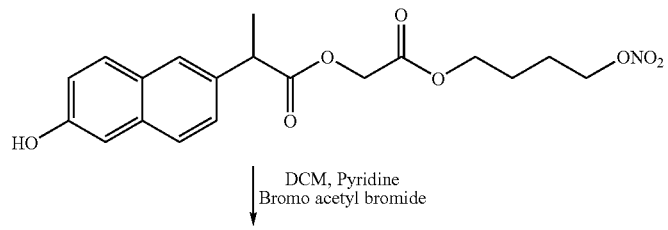

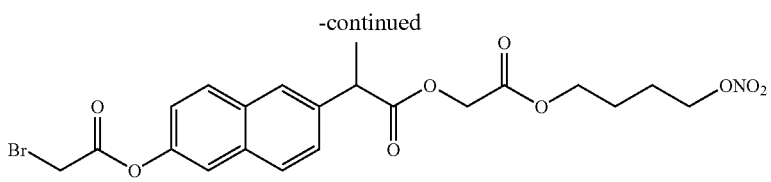

To a solution of 2-(6-hydroxy-naphthalen-2-yl)-propionic acid and 4-nitrooxy-butoxy carbonyl methyl ester (17 grams) and pyridine (5.7 ml) in dichloromethane (200 ml) maintained at 0-5° C. under $N_2$ atmosphere was added dropwise bromo acetyl bromide (5.6 ml). The reaction mixture was stirred at the same temperature for one hour. The reaction mixture was washed with water (25 ml) and a solution of 5% Sodium carbonate (75 ml). The solution was dried over sodium sulphate and the solvent was distilled off to get crude 2-[6-(2-Bromo-acetoxy)-naphthalen-2-yl]-propionic acid 4-nitrooxy-butoxy carbonyl methyl ester.

Example 15

Synthesis of 2-[6-(2-nitrooxy-acetoxy)-naphthalen-2-yl]-propionic acid 4-nitrooxy-butoxy carbonyl methyl ester

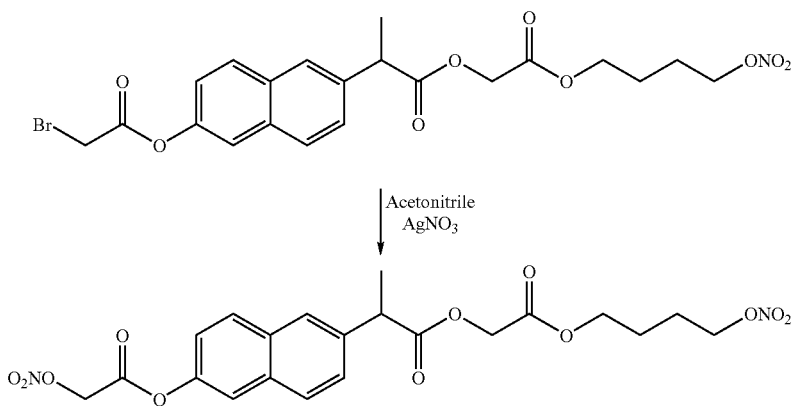

To a solution of 2-[6-(2-Bromo-acetoxy)-naphthalen-2-yl]-propionic acid 4-nitrooxy-butoxy carbonyl methyl ester (15 grams) in acetonitrile (150 ml) was added silver nitrate (10 grams), and the mixture stirred at 40° C. temperature for 24 hours. The reaction mixture was filtered and washed with acetonitrile, dried over sodium sulphate, the solvent distilled off under reduced pressure, and the residue was purified by column chromatography using hexane:ethyl acetate as eluant to get 10 grams of 2-[6-(2-nitrooxy-acetoxy)-naphthalen-2-yl]-propionic acid 4-nitrooxy-butoxy carbonyl methyl ester as a light yellow syrup.

Example 16

Synthesis of 2-acetoxy-benzoic acid benzyloxy carbonyl methyl ester

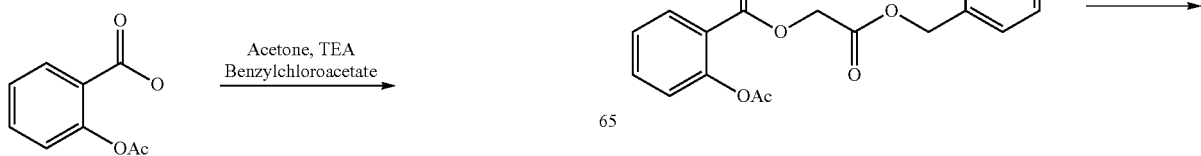

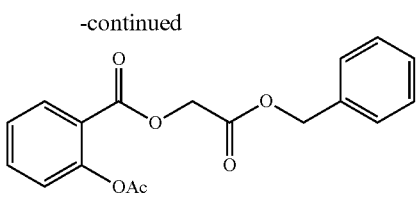

To a mixture of Aspirin (25 grams, 138.77 mmol) and triethylamine (29 ml) in acetone (250 ml) was added dropwise benzyl chloro acetate (30.75 grams), followed by stirring at 50° C. for five hours. The reaction mixture was poured onto cold water, crude 2-Acetoxy-benzoic acid benzyloxy carbonyl methyl ester was filtered, dried and purified by recrystallisation from a (1:4) mixture of chloroform:hexane to give pure 2-Acetoxy-benzoic acid benzyloxy carbonyl methyl ester (25 grams) as a white powder with a melting point of m.p: 91-92.5° C. The pure product was characterized using $^1$H NMR spectroscopy in $CDCl_3$ δ 2.30 (s, 3H, OAc), 4.82 (s, 2H, $CH_2$), 5.20 (s, 2H, CH2), 7.10 (d, 1H, Ar), 7.32 (m, 6H, Ar), 7.56 (t, 1H, Ar), 8.18 (d, 1H, Ar).

Example 17

Synthesis of 2-acetoxy-benzoic acid carboxymethyl ester

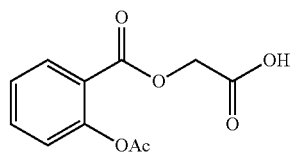

2-Acetoxy-benzoic acid benzyloxy carbonyl methyl ester (50 grams) was dissolved in ethyl acetate (150 ml) in a pressure vessel and 50% wet palladium on carbon (10%, 10 grams) was added. The reaction mixture was stirred under an atmosphere of hydrogen (4 Kg) for 14 hours. The catalyst was removed by filtration and ethyl acetate was distilled off under vacuum. The crude was precipitated by adding hexane followed by filtration, drying and purification by recrystallisation using a mixture of ethyl acetate:hexane to yield pure 2-Acetoxy-benzoic acid carboxymethyl ester (32 grams) as a white powder with a melting point of 130-131.5° C. The pure product was characterized using $^1$H NMR spectroscopy in DMSO-$d_6$ δ 2.28 (s, 3H, OAc), 4.8 (s, 2H, CH$_2$), 7.24 (d, 1H, Ar), 7.55 (t, 1H, Ar), 7.74 (t, 1H, Ar), 8.10 (d, 1H, Ar), 13.20 (bs, 1H, COOH).

Example 18

Synthesis of 2-acetoxy-benzoic acid 4-bromo-butoxy carbonyl methyl ester

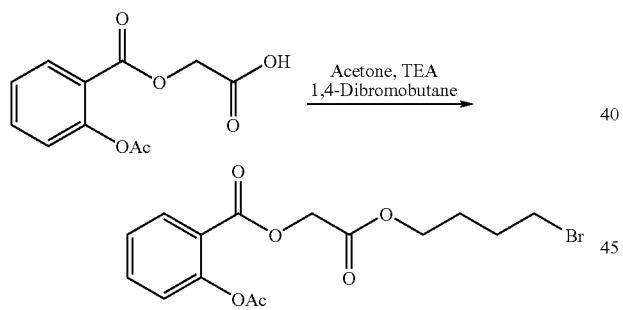

To a mixture of 2-acetoxy-benzoic acid carboxymethyl ester (30 grams), and triethylamine (26.5 ml) in acetone (200 ml) was added dropwise 1,4-dibromo butane (109 grams). The reaction mixture was left for stirring at room temperature for 24 hours. The reaction mixture was poured onto cold water and crude 2-acetoxy-benzoic acid 4-bromobutoxy carbonyl methyl ester was extracted into dichloromethane followed by drying over sodium sulphate. Dichloromethane was distilled off under reduced pressure and the residue was purified by column chromatography using hexane as eluant to get 32 grams of 2-acetoxy-benzoic acid 4-bromo-butoxy carbonyl methyl ester as a light yellow liquid. The pure product was characterized using $^1$H NMR spectroscopy in CDCl$_3$ δ 1.88 (m, 4H, CH$_2$X$_2$), 2.32 (s, 3H, OAc), 3.39 (t, 2H, CH$_2$), 4.20 (t, 2H, CH$_2$), 4.75 (s, 2H, CH$_2$), 7.10 (d, 1H, Ar), 7.23 (t, 1H, Ar), 7.50 (t, 1H, Ar), 8.10 (d, 1H, Ar)

Example 19

Synthesis of 2-acetoxy-benzoic acid 4-nitrooxy-butoxy carbonyl methyl ester

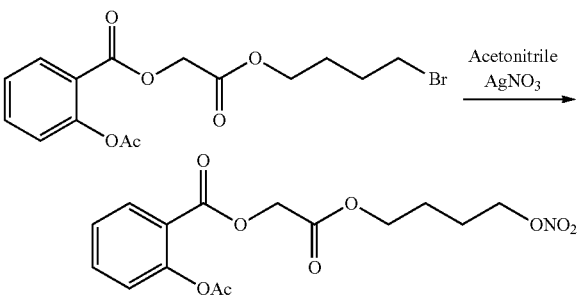

To a solution of 2-Acetoxy-benzoic acid 4-bromo-butoxy carbonyl methyl ester (20 grams) in acetonitrile (150 ml) was added silver nitrate (13.6 grams). The reaction mixture was refluxed for four hours. The reaction mixture was filtered and washed with acetonitrile, dried over sodium sulphate followed by distillation of solvent under reduced pressure. The residue was purified by column chromatography using hexane as eluant to get 15 grams of 2-acetoxy-benzoic acid 4-nitrooxy-butoxy carbonyl methyl ester as a light yellow liquid. The pure product was characterized using $^1$H NMR spectroscopy in CDCl$_3$ δ 1.80 (m, 4H, CH$_2$X$_2$), 2.34 (s, 3H, OAc), 4.22 (t, 2H, CH$_2$), 4.44 (t, 2H, CH$_2$), 4.80 (s, 2H, CH$_2$), 7.14 (d, 1H, Ar), 7.34 (t, 1H, Ar), 7.60 (t, 1H, Ar), 8.08 (d, 1H, Ar.

Example 20

Synthesis of bromo-acetic acid 2-formyl-phenyl ester

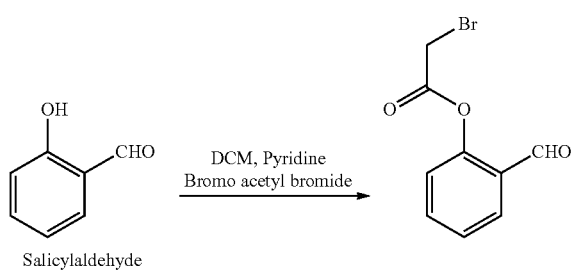

To a solution of Salicylaldehyde (50 grams) and pyridine (48.5 grams) in dichloromethane (500 ml) maintained at 0-5° C. under nitrogen atmosphere was added dropwise bromoacetyl bromide (210.6 grams). The reaction mixture was stirred for one hour at the same temperature. The reaction mixture was washed with 1000 ml of water and 1500 ml of 5% sodium bicarbonate solution, dried over sodium sulphate followed by distillation of solvent under reduced pressure to get 60.0 grams of bromo-acetic acid 2-formyl-phenyl ester.

Example 21

Synthesis of nitrooxy-acetic acid 2-formyl-phenyl ester

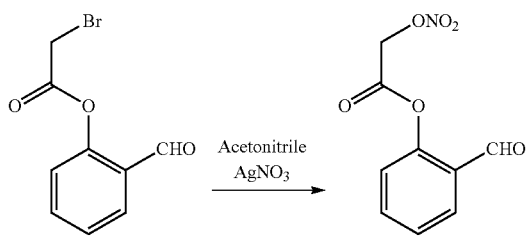

To a solution of bromoacetic acid 2-formyl-phenyl ester (10 grams) in acetonitrile (150 ml) was added silver nitrate (14.0 grams). The reaction mixture was stirred at room temperature for 35-38 hours. The reaction mixture was then filtered and washed with acetonitrile, dried over sodium sulphate, and the solvent was distilled off under reduced pressure to leave the residue which was purified by column chromatography using hexane:ethyl acetate as eluant to yield 3.0 grams of nitrooxy-acetic acid 2-formyl-phenyl ester as brown syrup. The pure product was characterized using $^1$H NMR spectroscopy in CDCl$_3$ δ 5.25 (s, 2H, OCH$_2$), 7.20 (d, 1H, Ar), 7.53 (dd, 1H, Ar), 7.63 (dd, 1H, Ar), 7.90 (d, 1H, Ar).

Example 22

Synthesis of 2-(2-nitrooxy-acetoxy)-benzoic acid

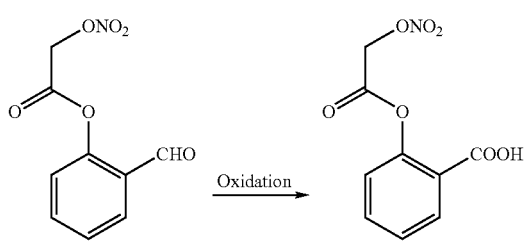

To a solution of nitrooxyacetic acid-2-formyl-phenyl ester (3.0 grams) in acetone (50 ml) was added potassium permanganate (3 grams) at 0° C. and stirred at the same temperature for 5-6 hours. Oxalic acid (15 grams) was added to the reaction mixture and the reaction mixture was washed with acetone followed by filtration, the solution was dried over sodium sulphate and the solvent was distilled off under reduced pressure. The residue was dissolved in dichloromethane and the organic layer was washed with water and dried over sodium sulphate. The solvent was distilled off under reduced pressure, purified by column chromatography using a mixture of hexane:ethyl acetate as an eluant to yield 1.0 grams of product (an off white powder). The product is purified further to yield 2-(2-nitrooxy-acetoxy)-benzoic acid.

Example 23

Synthesis of 2-hydroxy-benzoic acid benzyloxy carbonyl methyl ester

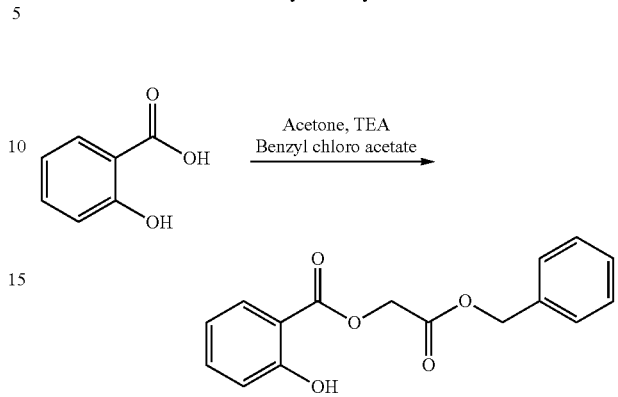

To a mixture of Salicylic acid (100 grams, 724 mmol) and triethylamine (152 ml) in acetone (500 ml) was added dropwise benzyl chloroacetate (147 grams). The solution was stirred at 50° C. temperature for four hours. The reaction mixture was poured onto cold water and the isolated crude 2-hydroxy-benzoic acid benzyloxy carbonyl methyl ester was filtered, dried and purified by recrystallising from a mixture of ethyl acetate:hexane to yield pure 2-hydroxy-benzoic acid benzyloxy carbonyl methyl ester (50 grams) as a white powder with a melting point of 75.5-77° C.

Example 24

Synthesis of 2-hydroxy-benzoic acid carboxymethyl ester

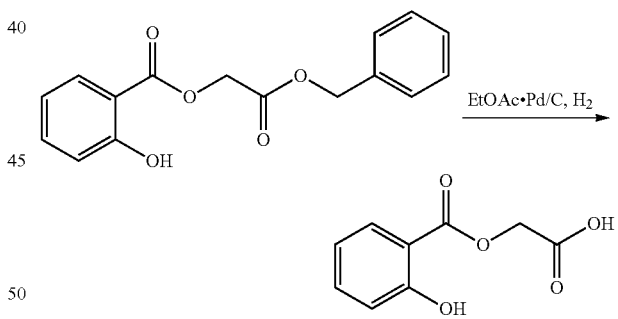

To a solution of 2-hydroxy-benzoic acid benzyloxy carbonyl methyl ester (55 grams) in ethyl acetate (300 ml) in a pressure vessel was added 50% wet Palladium on carbon (10%, 15 grams). The reaction mixture was stirred under an atmosphere of hydrogen (4 Kg) for 16 hours. The catalyst was removed by filtration and ethyl acetate was distilled off under vacuum to yield crude 2-hydroxy-benzoic acid carboxymethyl ester, which was precipitated from hexane. The precipitate was filtered, dried and purified by recrystallisation from a mixture of ethyl acetate:hexane to yield 33 grams of pure 2-hydroxy-benzoic acid carboxymethyl ester as a white powder. The pure product was characterized using $^1$H NMR spectroscopy in DMSO-d$_6$ δ 4.85 (s, 2H, CH$_2$), 7.00 (m, 2H, Ar), 7.55 (t, 1H, Ar), 7.85 (d, 1H, Ar), 10.30 (bs, 1H, OH). The pure product has a melting point of 131-132.5° C.

Example 25

Synthesis 2-hydroxy-benzoic acid 4-bromo-butoxy carbonyl methyl ester

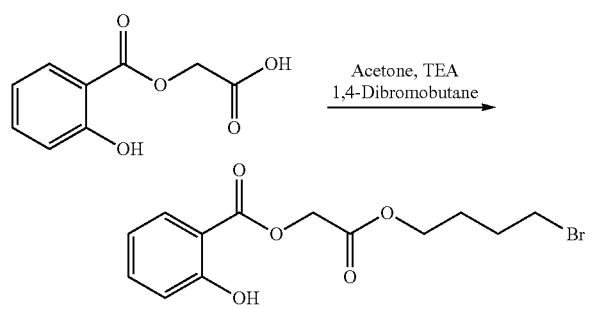

To a mixture of 2-hydroxybenzoic acid carboxy methyl ester (33 grams), and triethylamine (36 ml) in acetone (400 ml) was added dropwise 1,4-dibromo butane (146 grams). The reaction mixture was stirred at 40° C. for 16 hours. The reaction mixture was poured onto cold water to yield crude 2-Hydroxy-benzoic acid 4-bromobutoxy carbonyl methyl ester which was extracted into dichloro methane and dried over sodium sulphate. The solvent was distilled off under reduced pressure and the residue was purified by column chromatography using a mixture of hexane:ethyl acetate as eluant to yield 40 grams of 2-hydroxybenzoic acid-4-bromo-butoxy carbonyl methyl ester as a light yellow liquid. The pure product was characterized using $^1$H NMR spectroscopy in $^1$H NMR (CDCl$_3$) δ 1.95 (m, 4H, CH$_2$X$_2$), 3.40 (t, 2H, CH$_2$), 4.25 (t, 2H, CH$_2$), 4.85 (s, 2H, CH$_2$), 6.90 (m, 2H, Ar), 7.5 (t, 1H, Ar), 7.90 (d, 1H, Ar), 10.35 (s, 1H, OH).

Example 26

Synthesis of 2-hydroxy-benzoic acid 4-nitrooxy-butoxy carbonyl methyl ester

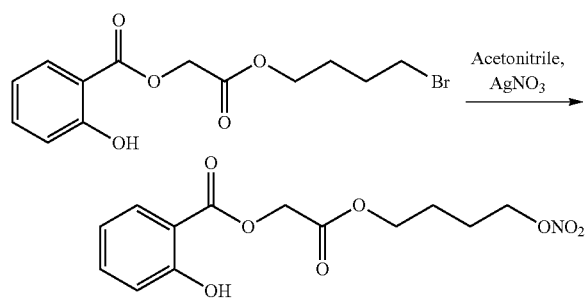

To a solution of 2-hydroxy-benzoic acid 4-bromo-butoxy carbonyl methyl ester (30 grams) in acetonitrile (300 ml) was added silver nitrate (30 grams) and stirred at 50° C. temperature for eight hours. The reaction mixture was filtered and washed with acetonitrile, dried over sodium sulphate, the solvent distilled off under reduced pressure, and the residue was dissolved in dichloromethane, filtered off the salts; organic layer washed with water (50 ml), dried over sodium sulphate, distilled under vacuum, and precipitated with hexane to yield 23 grams of 2-hydroxy-benzoic acid 4-nitrooxy-butoxy carbonyl methyl ester as an off-white powder. The pure product was characterized using $^1$H NMR spectroscopy in $^1$H NMR (CDCl$_3$) δ 1.85 (m, 4H, CH$_2$X$_2$), 4.25 (t, 2H, CH$_2$), 4.55 (t, 2H, CH$_2$), 4.85 (s, 2H, CH$_2$), 6.90 (m, 2H, Ar), 7.5 (t, 1H, Ar), 7.90 (d, 1H, Ar), 10.30 (s, 1H, OH). The pure product has a melting point of 84-86.5° C.

Example 27

Synthesis of 2-(2-bromo-acetoxy)-benzoic acid 4-nitrooxy-butoxy carbonyl methyl ester

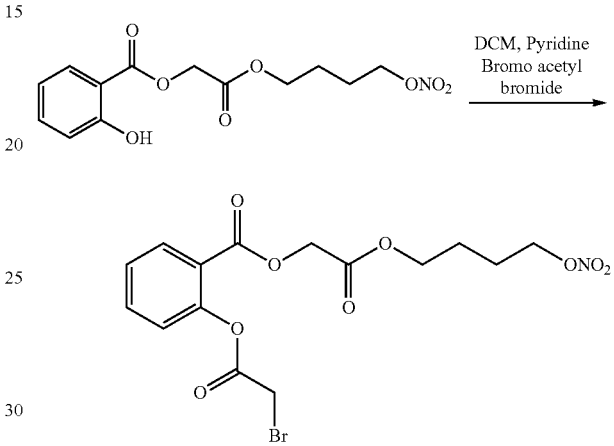

To a solution of 2-hydroxy-benzoic acid 4-nitrooxy-butoxy carbonyl methyl ester (20 grams) and pyridine (8 ml, 98.91 mmol) in dichloromethane (300 ml) maintained at 0-5° C. under N$_2$ atmosphere was added dropwise bromoacetyl bromide (8 ml). The reaction mixture was stirred at the same temperature for two hours. The reaction mixture was washed with water (200 ml) and a 5% solution of sodium carbonate (300 ml). The solution was dried over sodium sulphate and solvent was distilled off to yield crude 2-hydroxy-benzoic acid 4-nitrooxy-butoxy carbonyl methyl ester as light brown syrup The pure product was characterized using $^1$H NMR spectroscopy in $^1$H NMR (CDCl$_3$) δ 1.70 (m, 4H, CH$_2$X$_2$), 4.15 (t, 4H, CH$_2$), 4.35 (s, 2H, CH$_2$), 4.70 (s, 2H, CH$_2$), 7.05 (d, 1H, Ar), 7.30 (t, 1H, Ar), 7.55 (t, 1H, Ar), 8.05 (d, 1H, Ar).

Example 28

Synthesis of 2-(2-nitrooxy-acetoxy)-benzoic acid 4-nitrooxy-butoxy carbonyl methyl ester

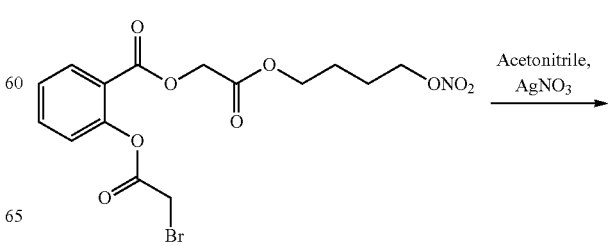

-continued

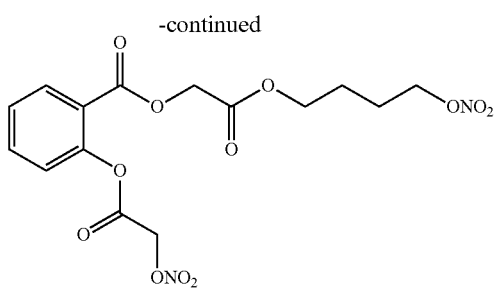

To a solution of 2-(2-bromoacetoxy)-benzoic acid-4-nitrooxy-butoxy carbonyl methyl ester (15 grams) in acetonitrile (150 ml) was added Silver nitrate (12.2 grams). The solution was stirred at 50° C. temperature for twenty four hours. The reaction mixture was filtered, washed with acetonitrile, and dried over sodium sulphate. The solvent was distilled off under reduced pressure. The residue was dissolved in dichloro methane, and the salts were filtered off. The organic layer was washed with water (50 ml), dried over sodium sulphate, distilled under vacuum to yield 2-(2-nitrooxy-acetoxy)-benzoic acid 4-nitrooxy-butoxy carbonyl methyl ester, which was purified by column chromatography using a mixture of hexane:ethyl acetate The product was further precipitated with hexane to yield 7.5 grams of 2-(2-nitrooxy-acetoxy)-benzoic acid 4-nitrooxy-butoxy carbonyl methyl ester as a white powder. The pure product was characterized using $^1$H NMR spectroscopy in $^1$H NMR (CDCl$_3$) δ δ 1.75 (m, 4H, CH$_2$X$_2$), 4.20 (t, 2H, CH$_2$), 4.45 (t, 2H, CH$_2$), 4.80 (s, 2H, CH$_2$), 5.30 (s, 2H, CH$_2$), 7.15 (d, 1H, Ar), 7.45 (t, 1H, Ar), 7.65 (t, 1H, Ar), 8.15 (d, 1H, Ar).

Example 29

Synthesis of 2-(6-hydroxy-naphthalen-2-yl)-propionic acid 2-(2-{2-[6-hydroxy-naphthalen-2-yl)-propionyloxy]-acetoxy}-acetoxy)-ethoxy carbonyl methoxy carbonyl methyl ester To a mixture of 2-(6-Hydroxy-naphthalen-2-yl)-propionic acid carboxymethyl ester (35 grams), triethylamine (12 ml) in dimethylformamide (350 ml) at 0° C. was added dichloro linker (12.5 grams). The reaction mixture was stirred at 60° C. for 21 hours. The reaction mixture was poured onto cold water and the crude product was extracted into ethyl acetate. The ethyl acetate extract was washed with 5% sodium bicarbonate solution and water followed by drying over sodium sulphate. Ethyl acetate was distilled off and the product was purified by column chromatography with hexane:ethyl acetate as eluant to yield pure 2-(6-hydroxy-naphthalen-2-yl)-propionic acid 2-(2-{2-[2-(6-hydroxy-naphthalen-2-yl)-propionyloxy]-acetoxy}-acetoxy)-ethoxy carbonyl methoxy carbonyl methyl ester (13.4 grams) as a white powder with a melting point of 85-88° C. The pure product was characterized via $^1$H NMR in (CDCl$_3$) δ 1.55 (d, 3H, CH$_3$), 3.60 (s, 4H, CH$_2$X$_2$), 3.90 (q, 1H, CH), 4.55 (q, 2H, OCH$_2$), 5.20 (s, 1H, OH), 7.04 (d, 2H, Ar), 7.35 (d, 1H, Ar), 7.55 (d, 1H, Ar), 7.62 (m, 2H, Ar).

Example 30

Synthesis of 2-(6-bromo-hexanoyloxy)-benzoic acid benzyloxy carbonyl methyl ester

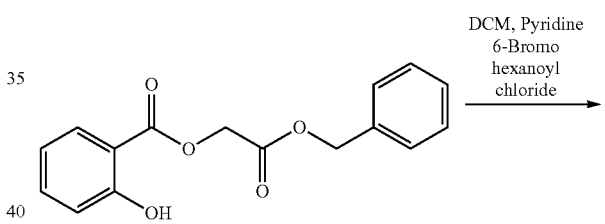

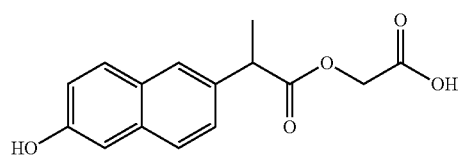

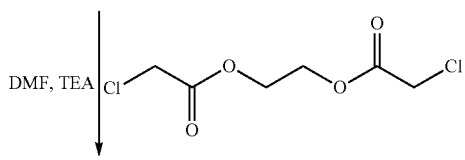

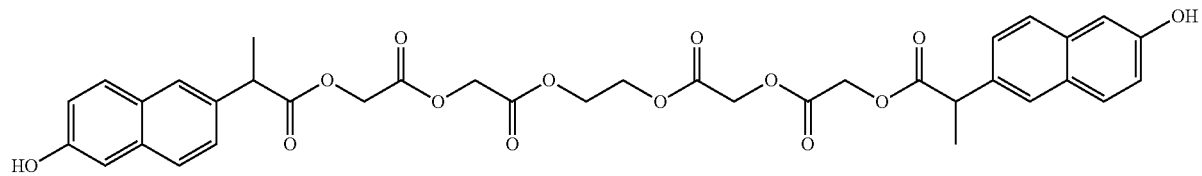

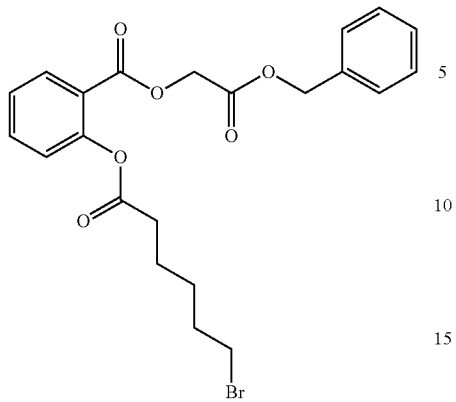

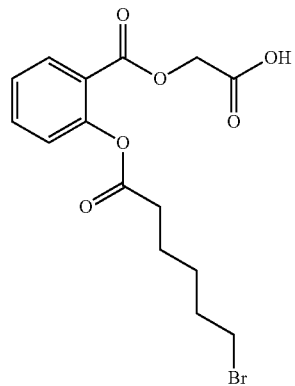

To a solution of 2-Hydroxy-benzoic acid benzyloxy carbonyl methyl ester (10 grams) and pyridine (4.2 ml) in dichloromethane (100 ml) at 0° C. under N₂ atmosphere was added dropwise 6-bromo hexanoyl chloride (9 grams). The reaction mixture was stirred at the same temperature for two hours. The reaction mixture was washed with water, 5% Sodium carbonate, 5% Copper Sulphate and dried over Sodium sulphate. The solvent was distilled off to yield crude compound which was purified by column chromatography using a mixture of hexane and ethyl acetate. The product was further precipitated with hexane to yield 12 grams of 2-(6-Bromo-hexanoyloxy)-benzoic acid benzyloxy carbonyl methyl ester as white powder with a melting point of 59-60° C. The product was characterized via $^1$H NMR (CDCl₃) δ 1.50 (m, 2H, CH₂), 1.70 (m, 2H, CH₂), 1.85 (m, 2H, CH₂), 2.55 (t, 2H, CH₂), 3.30 (t, 2H, CH₂), 4.70 (s, 2H, CH₂), 5.15 (s, 2H, CH₂), 7.05 (d, 1H, Ar), 7.30 (m, 6H, Ar), 7.50 (t, 1H, Ar), 8.05 (d, 1H, Ar).

Example 31

Synthesis 2-(6-bromo-hexanoyloxy)-benzoic acid carboxy methyl ester

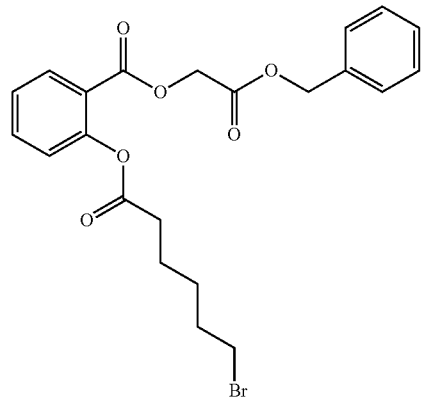

To a solution of 2-(6-bromo-hexanoyloxy)-benzoic acid benzyloxy carbonyl methyl ester (10 grams) in Ethyl acetate (200 ml) in a pressure vessel, 50% wet palladium on carbon (10%, 3 grams) was added and the mixture stirred under an atmosphere of hydrogen (4 Kg) for 4 hours. The catalyst was removed by filtration and Ethyl acetate was distilled under vacuum. The product was precipitated by adding diisopropyl ether, filtered and dried to yield pure 2-(6-Bromo-hexanoyloxy)-benzoic acid carboxy methyl ester (4 grams) as a white powder with a melting point of 102-103° C. The final product was analyzed by $^1$H NMR (CDCl₃+DMSO-d₆) δ 1.50 (m, 2H, CH₂), 1.70 (m, 2H, CH₂), 1.90 (m, 2H, CH₂), 2.55 (t, 2H, CH₂), 3.40 (t, 2H, CH₂), 4.65 (s, 2H, CH₂), 7.05 (d, 1H, Ar), 7.35 (t, 1H, Ar), 7.55 (t, 1H, Ar), 8.05 (d, 1H, Ar).

Example 32

Synthesis of 2-(6-nitrooxy-hexanoyloxy)-benzoic acid carboxy methyl ester

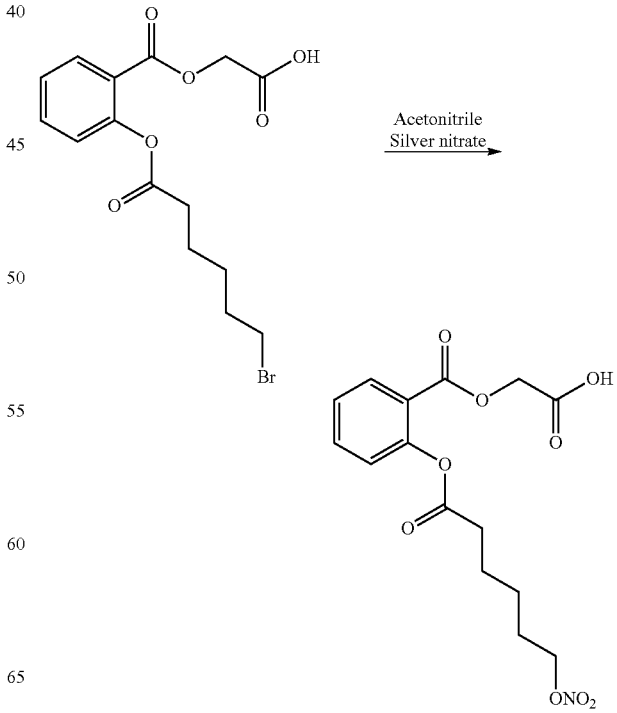

To a solution of 2-(6-bromo-hexanoyloxy)-benzoic acid carboxy methyl ester (20 grams) in acetonitrile (200 ml) at 0° C. was added silver nitrate (18 grams) and stirred at room temperature for 16 hours, later at reflux temperature for 6 hours. The reaction mixture was filtered and washed with acetonitrile and dried over Sodium sulphate. The solvent was distilled off under reduced pressure and the residue was dissolved in dichloro methane, washed with water and dried over Sodium sulphate. The dichloromethane was distilled under vacuum to get crude product which was purified by column chromatography using dichloromethane as eluant to yield 8 grams of 2-(6-nitrooxy-hexanoyloxy)-benzoic acid carboxy methyl ester as white powder with a melting point of 87.5-89.5° C. The final product was characterized by $^1$H NMR (DMSO-$d_6$) δ 1.45 (m, 2H, $CH_2$), 1.70 (m, 4H, $CH_2X2$), 2.60 (t, 2H, $CH_2$), 4.55 (t, 2H, $CH_2$), 4.75 (s, 2H, $CH_2$), 7.25 (d, 1H, Ar), 7.45 (t, 1H, Ar), 7.70 (t, 1H, Ar), 8.00 (d, 1H, Ar).

Example 33

Synthesis of 2-(6-nitrooxy-hexanoyloxy)-benzoic acid (2,2,5-trimethyl-[1,3]dioxan-5-yl carbamoyl)-methyl ester

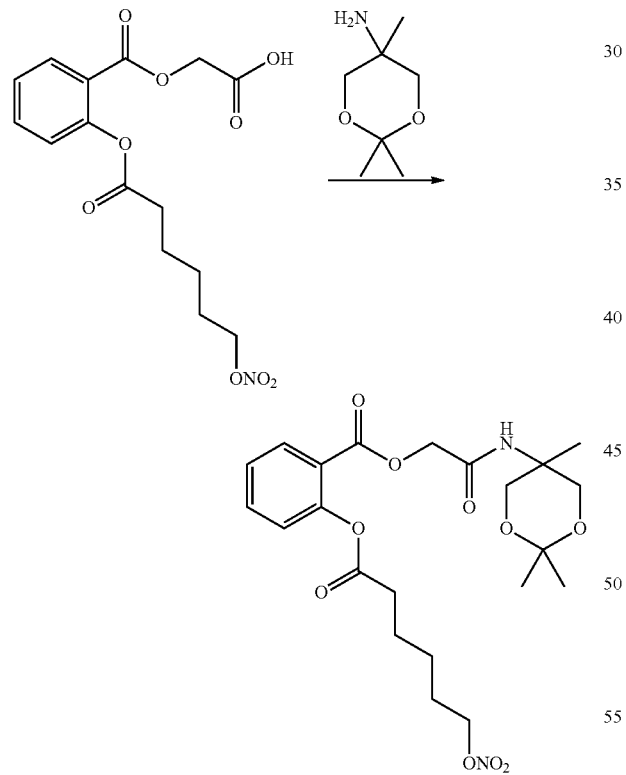

To a mixture of 2-(6-Nitrooxy-hexanoyloxy)-benzoic acid carboxy methyl ester (10 grams), 2,2,5-Trimethyl-[1,3]dioxan-5-yl amine (6 grams) and hydroxy benzotriazole (1.2 grams) in acetonitrile (150 ml) at 0° C. was added EDC.HCl (8 grams) in small lots and stirred at room temperature for 18 hours. The reaction mixture poured onto cold water, extracted into ethyl acetate, dried over anhydrous Sodium sulphate, distilled and purified by column chromatography using from a mixture of hexane:Ethyl acetate to give pure 2-(6-nitrooxy-hexanoyloxy)-benzoic acid (2,2,5-trimethyl-[1,3]dioxan-5-yl carbamoyl)-methyl ester (4 grams) as light yellow syrup. $^1$H NMR (CDCl$_3$) δ 1.32 (s, 3H, $CH_3$), 1.34 (s, 3H, $CH_3$), 1.40 (s, 3H, $CH_3$), 1.45 (m, 2H, $CH_2$), 1.78 (m, 4H, $CH_2X2$), 2.64 (t, 2H, $CH_2$), 3.62 (d, 2H, $CH_2$), 3.92 (d, 2H, $CH_2$), 4.46 (t, 2H, $CH_2$), 4.70 (s, 2H, $CH_2$), 5.54 (s, 1H, NH), 7.12 (d, 1H, Ar), 7.34 (t, 1H, Ar), 7.64 (t, 1H, Ar), 8.05 (d, 1H, Ar).

Example 34

Synthesis of 2-(6-nitrooxy-hexanoyloxy)-benzoic acid (2-hydroxy-1-hydroxy methyl-1-methyl-ethyl-carbamoyl)-methyl ester

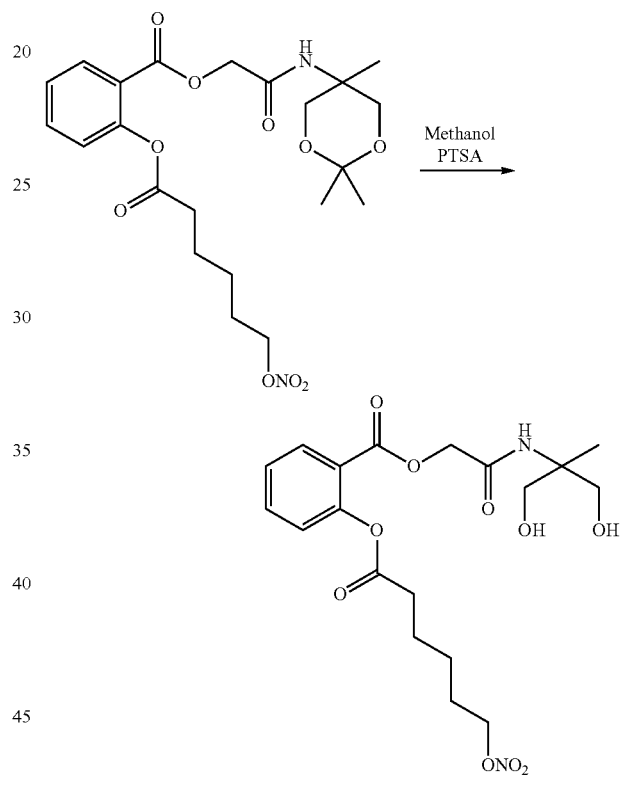

To a solution of 2-(6-nitrooxy-hexanoyloxy)-benzoic acid (2,2,5-trimethyl-[1,3]dioxan-5-yl carbamoyl)-methyl ester (5.5 grams) in a mixture of Methanol (55 ml) and water (2.5 ml), was added p-toluenesulfonic acid (0.2 grams) and stirred at room temperature for 2 hours. The reaction mixture poured onto cold water, extracted with Ethyl acetate, washed the organic layer with water, dried over Sodium sulphate and distilled under vacuum to get crude compound which was purified by column chromatography using Hexane:Ethyl acetate as eluant to get 1 grams of 2-(6-Nitrooxy-hexanoyloxy)-benzoic acid (2-hydroxy-1-hydroxy methyl-1-methyl-ethylcarbamoyl)-methyl ester as light yellow syrup. The product was characterized by $^1$H NMR (DMSO-$d_6$) δ 1.16 (s, 3H, $CH_3$), 1.45 (m, 2H, $CH_2$), 1.70 (m, 4H, $CH_2X2$), 2.64 (t, 2H, $CH_2$), 3.50 (m, 4H, $CH_2X2$), 4.55 (t, 2H, $CH_2$), 4.70 (s, 2H, $CH_2$), 4.80 (t, 2H, $OHX2$), 7.25 (d, 1H, Ar), 7.40 (m, 2H, Ar & NH), 7.70 (t, 1H, Ar), 8.00 (d, 1H, Ar).

Example 35

Synthesis of 6-bromo-hexanoic acid 6-(1-{2-[2-(2-{2-[6-(6-bromo-hexanoyloxy)-naphthalen-2-yl]-propionyloxy}-acetoxy)-acetoxy]ethoxycarbonyl methoxycarbonylmethoxycarbonyl}-ethyl)-naphthalen-2-yl ester

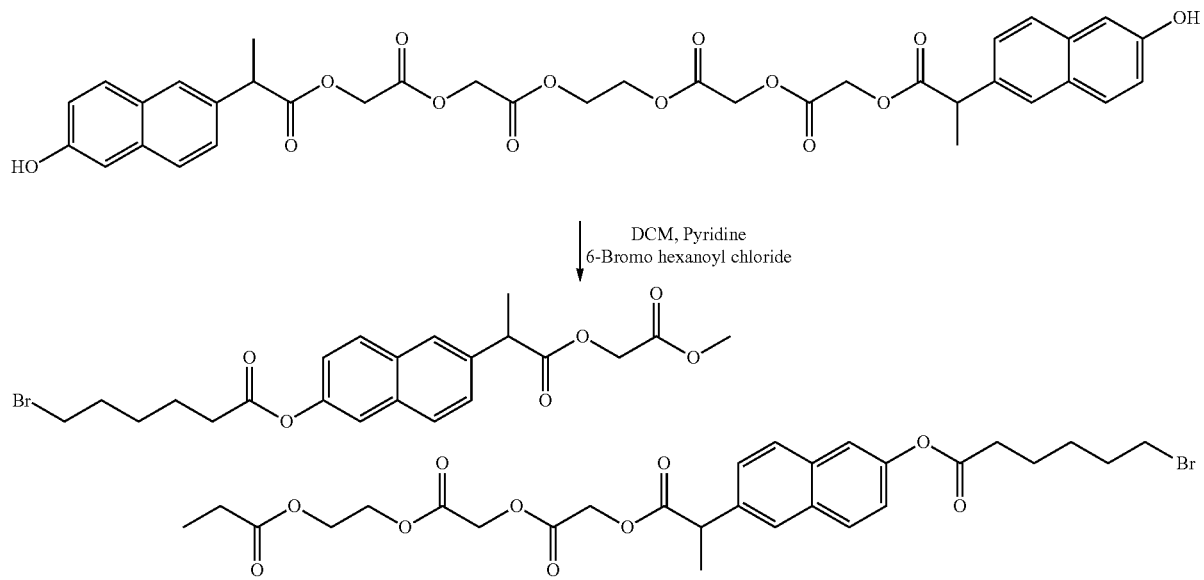

To a solution of 2-(6-hydroxy-naphthalen-2-yl)-propionic acid methyl ester (12 grams) and Pyridine (4.12 grams) in dichloromethane (120 ml) at 0° C. under N$_2$ atmosphere was added dropwise 6-bromo hexanoyl chloride (14.8 grams). The reaction mixture stirred at the same temperature for one hour. The reaction mixture was washed with water (200 ml), 5% Sodium bicarbonate solution (100 ml) and 5% Copper sulphate solution (100 ml) followed by drying over sodium sulphate. The solvent was distilled off to yield crude product which was purified by recrystallisation in a mixture of diisopropylether:hexane to yield 6-bromo-hexanoic acid 6-(1-{2-[2-(2-{2-[6-(6-bromo-hexanoyloxy)-naphthalen-2-yl]-propionyloxy}-acetoxy)-acetoxy]-ethoxycarbonyl methoxycarbonyl methoxy carbonyl}-ethyl)-naphthalen-2-yl ester (11.2 grams) as white powder with a melting point of 49-50° C. The pure product was characterized via $^1$H NMR in (CDCl$_3$) δ 1.60 (m, 5H, CH$_3$ & CH$_2$), 1.80 (m, 2H, CH$_2$), 1.90 (m, 2H, CH$_2$), 2.65 (t, 2H, CH$_2$), 3.45 (t, 2H, CH$_2$), 3.70 (m, 4H, CH$_2$X2), 4.00 (q, 1H, CH), 4.60 (q, 2H, CH$_2$), 7.20 (d, 1H, Ar), 7.45 (d, 2H, Ar), 7.72 (m, 3H, Ar).

Example 36

Synthesis of 6-nitrooxy-hexanoic acid 6-(1-{2-[2-(2-{2-[6-(6-nitrooxy-hexanoyloxy)-naphthalen-2-yl]-propionyloxy}-acetoxy)-acetoxy]-ethoxycarbonyl methoxycarbonyl methoxy carbonyl}-ethyl)-naphthalen-2-yl ester

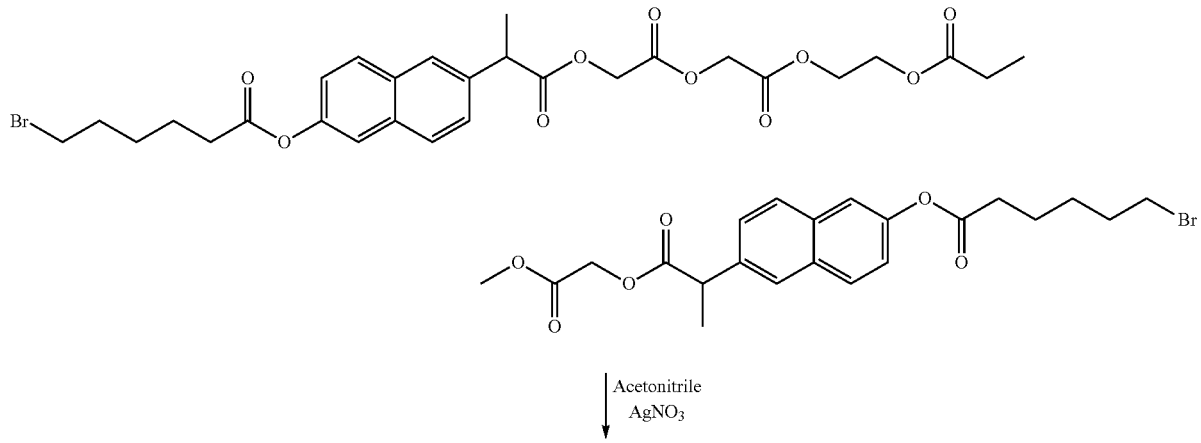

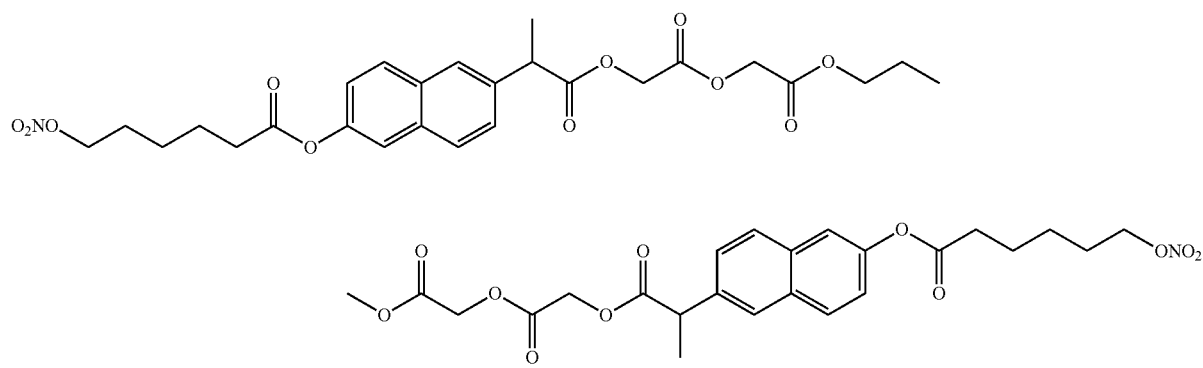

To a solution of 6-bromo-hexanoic acid 6-(1-{2-[2-(2-{2-[6-(6-bromo-hexanoyloxy)-naphthalen-2-yl]-propionyloxy}-acetoxy)-acetoxy]-ethoxy carbonyl methoxy carbonyl methoxy carbonyl}-ethyl)-naphthalen-2-yl ester (9 grams) in acetonitrile (180 ml) at 0° C. was added silver nitrate (4.3 grams). The reaction mixture was stirred overnight at room temperature followed by stirring at 60° C. for 5 hours. The reaction mixture was filtered and washed with acetonitrile and dried over sodium sulphate. Acetonitrile was distilled off to yield crude product which was dissolved in chloroform. The salts were filtered off and the solution was dried over Sodium sulphate after washing with water. The chloroform was distilled off under reduced pressure and the residue was purified by recrystallisation from a mixture of toluene:hexane to yield 6.1 grams of 6-nitrooxy-hexanoic acid 6-(1-{2-[2-(2-{2-[6-(6-nitrooxy-hexanoyloxy)-naphthalen-2-yl]-propionyloxy}-acetoxy)-acetoxy]-ethoxycarbonyl methoxy carbonyl methoxy carbonyl}-ethyl)-naphthalen-2-yl ester as white powder with a melting point of 45.3-47° C. The pure product was characterized via $^1$H NMR in (CDCl$_3$) δ 1.55 (m, 2H, CH$_2$), 1.65 (d, 3H, CH$_3$), 1.80 (m, 4H, CH$_2$X2), 2.65 (t, 2H, CH$_2$), 3.65 (s, 4H, CH$_2$X2), 4.00 (q, 1H, CH), 4.95 (t, 2H, CH$_2$), 4.60 (q, 2H, CH$_2$), 7.20 (d, 1H, Ar), 7.50 (d, 2H, Ar), 7.80 (m, 3H, Ar).

Example 37
Synthesis of 6-bromo-hexanoic acid 3-[4-(6-bromo-hexanoyloxy)-phenyl]-4-oxo-4H-chromen-7-yl ester To a solution of daidzein (4',7-dihydroxyisoflavone, 25 grams) in dimethylformamide (250 ml) at room temperature under N$_2$ atmosphere was added 6-dromo hexanoyl chloride (68 grams). The reaction mixture was cooled to 0° C., and Pyridine (29 ml) was added dropwise to the reaction mixture. The solution was left for stirring at room temperature for 42 hours. The reaction mixture was poured onto cold water followed by extraction with ethyl acetate. The ethyl acetate layer was washed with 5% sodium carbonate solution followed by drying over Sodium sulphate. The ethyl acetate was distilled off to yield the crude compound and the crude product was precipitated in hexane and washed with isopropyl alcohol followed by filtration to yield 42 grams of 6-Bromo-hexanoic acid 3-[4-(6-bromo-hexanoyloxy)-phenyl]-4-oxo-4H-chromen-7-yl ester as off-white powder with a melting point of 102-104° C. The pure product was characterized via $^1$H NMR in (CDCl$_3$) δ 1.60 (m, 4H, CH$_2$X$_2$), 1.85 (m, 8H, CH$_2$X$_4$), 2.65 (m, 4H, CH$_2$CO X$_2$), 3.58 (t, 4H, CH$_2$BrX$_2$), 7.16 (m, 3H, Ar), 7.26 (d, 1H, Ar), 7.60 (d, 2H, Ar), 8.06 (s, 1H, Ar), 8.35 (d, 1H, Ar).

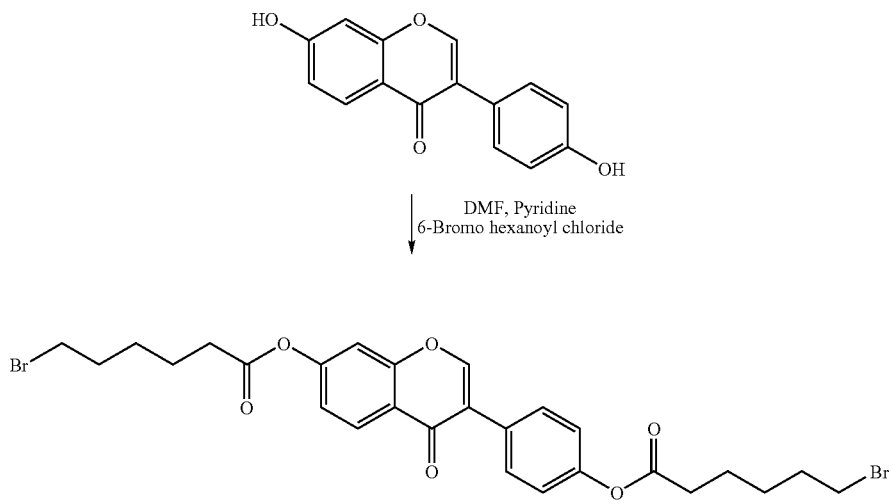

Example 38

Synthesis of 6-nitrooxy-hexanoic acid 3-[4-(6-nitrooxy-hexanoyloxy)-phenyl]-4-oxo-4H-chromen-7-yl ester

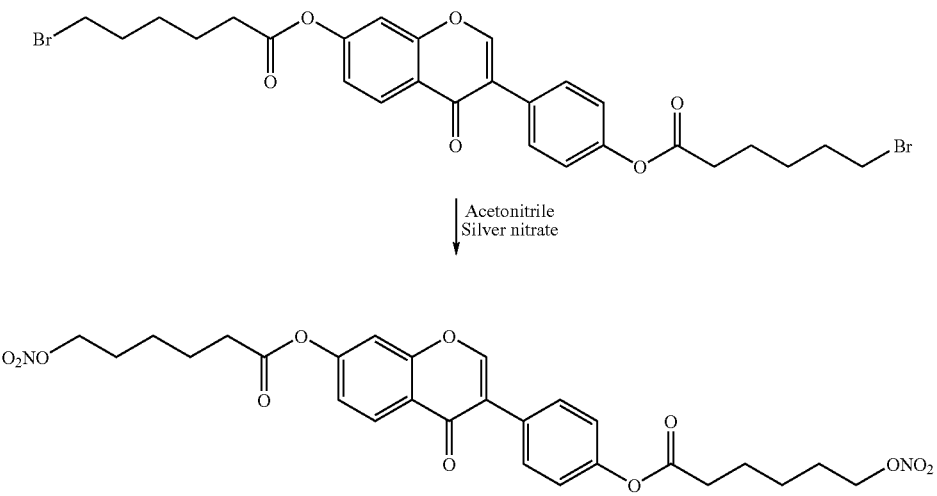

To a solution of 6-bromo-hexanoic acid 3-[4-(6-bromo-hexanoyloxy)-phenyl]-4-oxo-4H-chromen-7-yl ester (5 grams) in acetonitrile (50 ml) at 0° C. was added Silver nitrate (7.2 grams). The reaction mixture was stirred at room temperature for 4 hours followed by further stirring under reflux conditions for 28 hours. The reaction mixture was filtered and washed with acetonitrile followed by drying over sodium sulphate. Acetonitrile was distilled off under reduced pressure and the residue was precipitated in cold water. The precipitate was filtered and recrystallized from a mixture of toluene and hexane to yield 4 grams of 6-nitrooxy-hexanoic acid 3-[4-(6-nitrooxy-hexanoyloxy)-phenyl]-4-oxo-4H-chromen-7-yl ester as off-white powder with a melting point of 100-102° C. The pure product was characterized via $^1$H NMR in a mixture of (CDCl$_3$ and DMSO-d$_6$) δ 1.60 (m, 4H, CH$_2$X$_2$), 1.76 (m, 8H, CH$_2$X$_4$), 2.64 (m, 4H, CH$_2$CO X$_2$), 4.52 (t, 4H, CH$_2$ONO$_2$X$_2$), 7.12 (d, 2H, Ar), 7.22 (d, 1H, Ar), 7.32 (s, 2H, Ar), 7.68 (d, 2H, Ar), 8.2-18 (d, 1H, Ar), 8.45 (s, 1H, Ar).

Example 39

Synthesis of 2-(6-bromo-hexanoyloxy)-benzoic acid 4-nitrooxy-butoxy carbonyl methyl ester

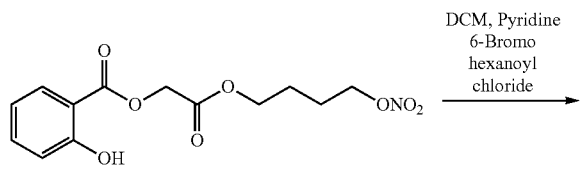

-continued

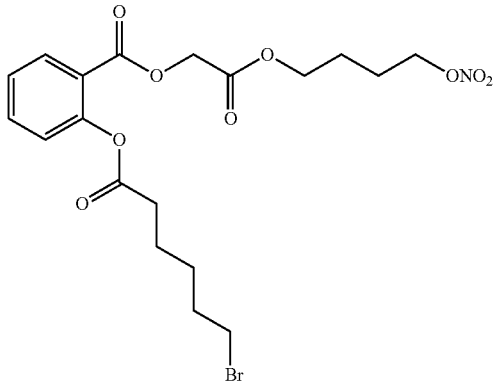

To a solution of 2-hydroxy-benzoicacid-4-nitrooxy-butoxy carbonyl methyl ester (15 grams) and pyridine (6 ml) in dichloromethane (150 ml) at 0° C. under N$_2$ atmosphere was added 6-bromohexanoyl chloride (13.5 grams) dropwise. The reaction mixture was stirred at room temperature for 24 hours. The reaction mixture was washed with water, 5% sodium carbonate solution and 5% copper sulphate solution. The solution was dried over sodium sulphate and solvent was distilled off. The residue was purified by column chromatography using a mixture of hexane:ethyl acetate as an eluant to yield 16 grams of 2-(6-bromo-hexanoyloxy)-benzoic acid 4-nitrooxy-butoxy carbonyl methyl ester as light yellow syrup. The pure product was characterized using $^1$H NMR (CDCl$_3$) δ 1.50 (m, 2H, CH$_2$), 1.70 (m, 6H, CH$_2$X$_3$), 1.85 (m, 2H, CH$_2$), 2.55 (t, 2H, CH$_2$), 3.35 (t, 2H, CH$_2$), 4.15 (s, 2H, CH$_2$), 4.35 (bs, 2H, CH$_2$), 4.70 (s, 2H, CH$_2$), 7.00 (d, 1H, Ar), 7.25 (t, 1H, Ar), 7.55 (t, 1H, Ar), 8.05 (d, 1H, Ar).

Example 40

Synthesis of 2-(6-nitrooxy-hexanoyloxy)-benzoic acid 4-nitrooxy-butoxy carbonyl methyl ester

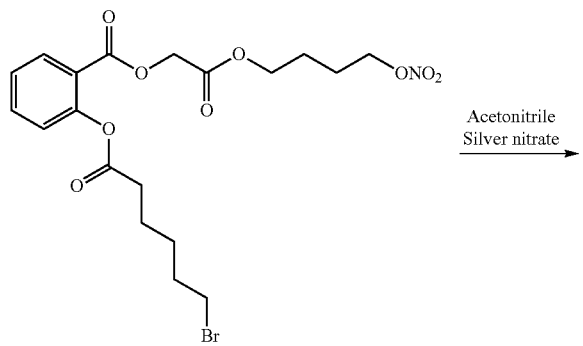

To a solution of 2-(6-bromo-hexanoyloxy)-benzoic acid 4-nitrooxy-butoxy carbonyl methyl ester (4 grams) in acetonitrile (40 ml) was added silver nitrate (2.7 grams). The reaction mixture was stirred at room temperature for twenty hours. The reaction mixture was filtered and washed with acetonitrile, and dried over sodium sulphate. The solvent was distilled off under reduced pressure and the residue was dissolved in dichloromethane. The salts were filtered off and the organic layer was washed with water followed by drying over sodium sulphate. The dichloromethane was distilled off under vacuum and the residue was purified by column chromatography using a mixture of hexane:ethyl acetate to yield 3 grams of 2-(2-nitrooxy-hexanoyloxy)-benzoic acid 4-nitrooxy-butoxy carbonyl methyl ester as light yellow syrup. The pure product was characterized using $^1$H NMR (CDCl$_3$) δ 1.50 (m, 2H, CH$_2$), 1.75 (m, 8H, CH$_2$X$_4$), 2.55 (t, 2H, CH$_2$), 4.15 (t, 2H, CH$_2$), 4.35 (m, 4H, CH$_2$X$_2$), 4.70 (s, 2H, CH$_2$), 7.00 (d, 1H, Ar), 7.25 (t, 1H, Ar), 7.55 (t, 1H, Ar), 8.05 (d, 1H, Ar).

Example 41

Synthesis of Aspirin Dimer Diol

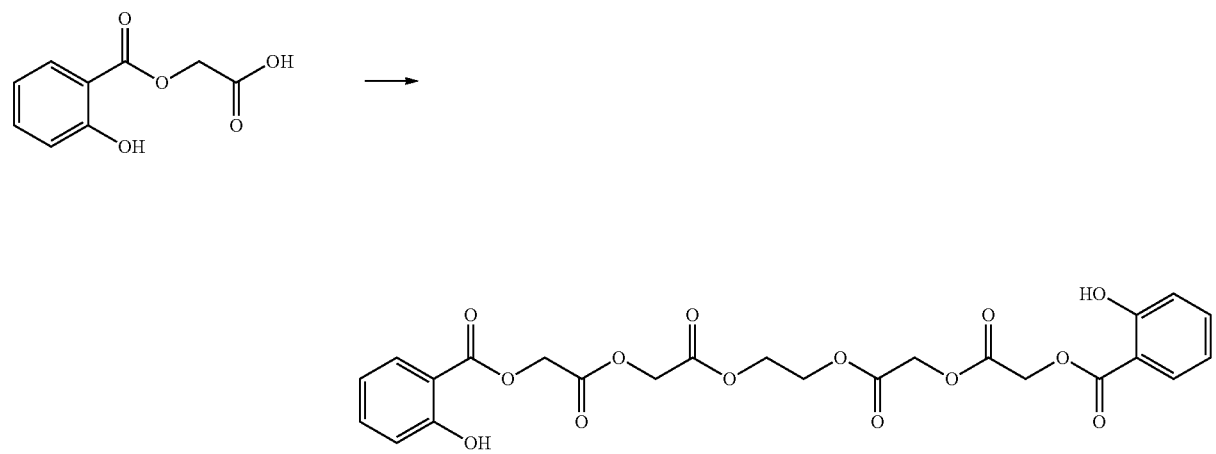

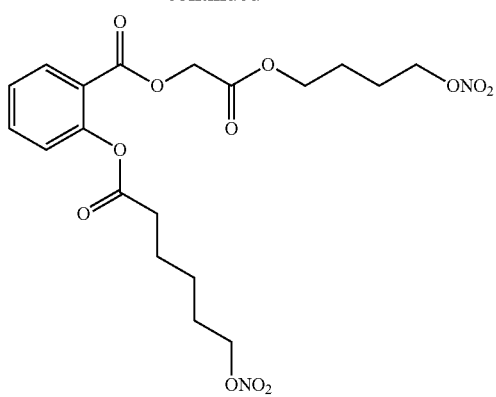

To a mixture of 2-hydroxy-benzoic acid carboxymethyl ester (22.8 grams) and triethylamine (22.6 ml) in acetone (200 ml) was added dichloro linker (10 grams). The reaction mixture was stirred at room temperature for 1 hour and then refluxed for 18 hours. The reaction mixture was poured onto cold water and crude product was extracted into ethyl acetate. It was washed with 5% sodium bicarbonate solution and water, followed by drying over sodium sulphate. The solvent was distilled off and precipitated with diisopropyl alcohol to give 8 grams of pure Aspirin dimer diol as a white powder with a melting point of 99-102° C. The product was characterized by $^1$H NMR (DMSO-d$_6$) δ 4.40 (s, 2H, CH$_2$), 4.90 (s, 2H, CH$_2$), 5.15 (s, 2H, CH$_2$), 7.05 (m, 2H, Ar), 7.62 (t, 1H, Ar), 7.90 (d, 1H, Ar), 10.30 (s, 1H, ArOH).

Example 42
Synthesis of Dibromo Aspirin Dimer

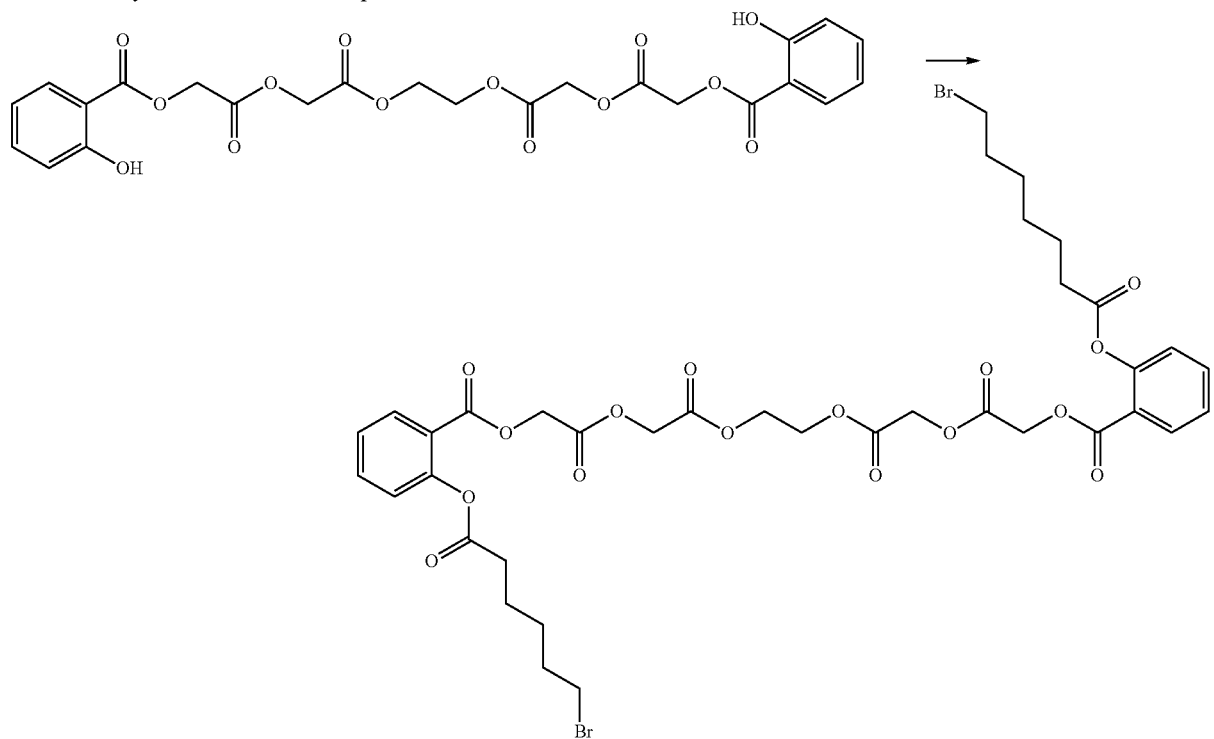

To a solution of Aspirin dimer diol (8 grams) and pyridine (4.2 ml) in dichloromethane (150 ml) at 0° C. under $N_2$ atmosphere was added dropwise 6-bromohexanoyl chloride (10 grams). The reaction mixture was stirred at the same temperature for four hours. The reaction mixture was washed with water (200 ml), 5% sodium bicarbonate solution and 5% copper sulphate solution. It was dried over sodium sulphate and the solvent was distilled off to yield crude product, which was purified by column chromatography using mixture of hexane:ethyl acetate to get dibromo Aspirin dimer (11 grams) as light yellow syrup. The pure product was characterized by $^1$H NMR (CDCl$_3$) δ 1.55 (m, 2H, CH$_2$), 1.75 (m, 2H, CH$_2$), 1.90 (m, 2H, CH$_2$), 2.65 (t, 2H, CH$_2$), 3.40 (t, 2H, CH$_2$), 4.40 (s, 2H, CH$_2$), 4.72 (s, 2H, CH$_2$), 4.90 (s, 2H, CH$_2$), 7.10 (d, 1H, Ar), 7.35 (t, 1H, Ar), 7.70 (t, 1H, Ar), 8.10 (d, 1H, Ar).

Example 43
Synthesis of Dinitro Aspirin Dimer

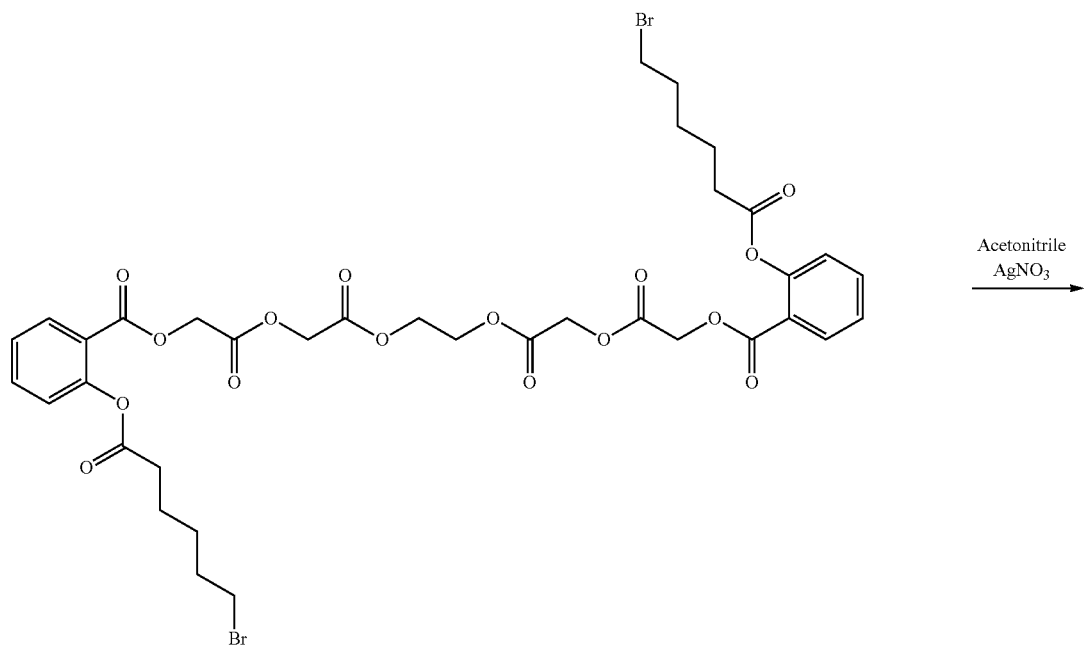

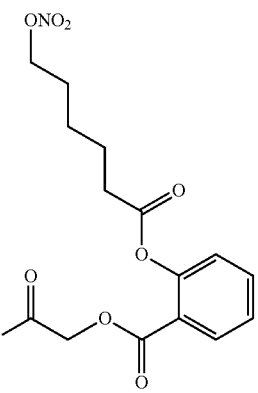
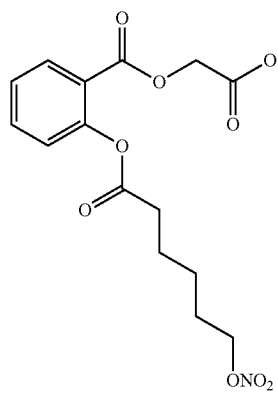

To a solution of dibromo Aspirin dimer (9 grams) in acetonitrile (150 ml) at 0° C. was added silver nitrate (5.1 grams) and stirred at room temperature for three hours followed by heating at 50° C. for 5 hours. The reaction mixture was filtered and washed with acetonitrile and dried over sodium sulphate. The solvent was distilled off and the crude was taken into chloroform. The salts were filtered off and washed with water and dried over sodium sulphate. The solvent was distilled off under reduced pressure and the residue was purified by column chromatography using a mixture of hexane:ethyl acetate to yield 6 grams of dinitro Aspirin dimer as light yellow syrup. The pure product was characterized by $^1$H NMR (CDCl$_3$) δ 1.55 (m, 2H, CH$_2$), 1.70 (m, 4H, CH$_2$X$_2$), 2.10 (t, 2H, CH$_2$), 4.35 (s, 2H, CH$_2$), 4.45 (t, 2H, CH$_2$), 4.70 (s, 2H, CH$_2$), 4.90 (s, 2H, CH$_2$), 7.05 (d, 1H, Ar), 7.35 (t, 1H, Ar), 7.55 (t, 1H, Ar), 8.15 (d, 1H, Ar).

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention.

The invention claimed is:

1. A nitric oxide oligomer of formula A:

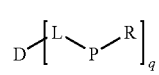

(A)

wherein:
L is —O— or —COO—;
D is:
  (i) together or separately from L, a biologically active substance, in which case q is 1 to 4 inclusive;
P is a polyester that is one of —[—X—]$_p$—, where monomer X is polymerization compatible with —CH$_2$COO—, or —[—Y—]$_p$—, where monomer Y is polymerization compatible with —COCH$_2$O—, wherein
p is independently an integer from 2 to 100 inclusive;
1 or more independently selected repeats X are:
  —CH$_2$COO— (glycolic acid moiety);
  —CH(CH$_3$)COO— (lactic acid moiety);
  —CH$_2$CH$_2$OCH$_2$COO— (dioxanone moiety);
  —CH$_2$CH$_2$CH$_2$CH$_2$CH$_2$COO— (caprolactone moiety);
  —(CH$_2$)$_y$COO— where y is one of the numbers 2, 3 or 4, or a number from 6 to 24 inclusive; or
  —(CH$_2$CH$_2$O)$_z$CH$_2$COO— where z is an integer between 2-24, inclusive;
the order and composition of repeats X is selected to provide a desired degradation of moiety -L-P—R;
1 or more independently selected repeats Y are:
  —COCH$_2$O— (glycolic ester moiety);
  —COCH(CH$_3$)O— (lactic ester moiety);
  —COCH$_2$OCH$_2$CH$_2$O— (dioxanone ester moiety);
  —COCH$_2$CH$_2$CH$_2$CH$_2$CH$_2$O— (caprolactone ester moiety);
  —CO(CH$_2$)$_m$O— where m is one of the numbers 2, 3 or 4, or a number from 6 to 24 inclusive; or, —COCH$_2$O(CH$_2$CH$_2$O)$_n$— where n is integer between 2-24 inclusive;

the order and composition of repeats Y is selected to provide a desired degradation of moiety -L-P—R; and R is according to one of the applicable following options (a) or (b):

(a) where P is —[—X—]$_p$, R can be an alkyl group, aryl, alkyl-aryl, an alicyclic group or alkyl-alicyclic, substituted with one or more —O—NO$_2$; and (b) where P is —[—Y—]$_p$, R can be —NO$_2$;

wherein if L is —COO—, then the corresponding P is —[—X—]$_p$—; and wherein the biologically active substances are selected from the group consisting of phenols, thiophenols, naphthols, flavonoids, isoflavonoids, coumarins, chromones, chalcones, cinnamic acids, benzoic acids, acetophenones, benzophenones, alkaloids, catechins, catechols, aminoalcohols, aminosalicyclic acids, hydrocinnamic acids, phenolic acids, resorcinols, indoles and hydroquinones.

2. The oligomer of claim 1, wherein the oligomer is according to one of Formulas I to III:

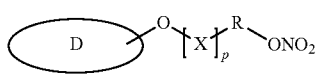    I

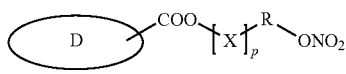    II

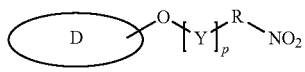    III

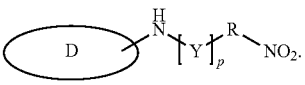    IV

3. The oligomer of claim 1, wherein the majority of repeats X or Y of formula A comprise repeats of Group B:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is one of the numbers 2, 3 or 4; or
—(CH$_2$CH$_2$O)$_z$CH$_2$COO—;
—COCH$_2$O— (glycolic ester moiety);
—COCH(CH$_3$)O— (lactic ester moiety);
—COCH$_2$OCH$_2$CH$_2$O— (dioxanone ester moiety);
—COCH$_2$CH$_2$CH$_2$CH$_2$CH$_2$O— (caprolactone ester moiety); —CO(CH$_2$)$_m$O— where m is one of the numbers 2, 3 or 4; or —COCH$_2$—O—(CH$_2$CH$_2$O)$_n$—.

4. The oligomer of claim 1, wherein the majority of repeats X or Y of formula A comprise repeats of Group C:
—CH$_2$COO—;
—CH(CH$_3$)COO—;
—CH$_2$CH$_2$OCH$_2$COO—;
—CH$_2$CH$_2$CH$_2$CH$_2$CH$_2$COO—;
—COCH$_2$O—;
—COCH(CH$_3$)O—;
—COCH$_2$OCH$_2$CH$_2$O—; or
—COCH$_2$CH$_2$CH$_2$CH$_2$CH$_2$O—.

5. The oligomer of claim 1, wherein 2 or more of repeats X or Y of formula A comprise repeats of Group C, where p is 10 or less, wherein Group C repeats are —CH$_2$COO—; —CH(CH$_3$)COO—; —CH$_2$CH$_2$OCH$_2$COO—; CH$_2$CH$_2$CH$_2$CH$_2$CH$_2$COO—; —COCH$_2$O—; —COCH(CH$_3$)O—; —COCH$_2$OCH$_2$CH$_2$O—; or —COCH$_2$CH$_2$CH$_2$CH$_2$CH$_2$O—.

6. The oligomer of claim 1, wherein the oligomer is one of the following (where n=2, 3 or 4):

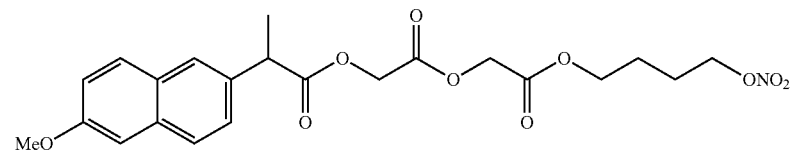

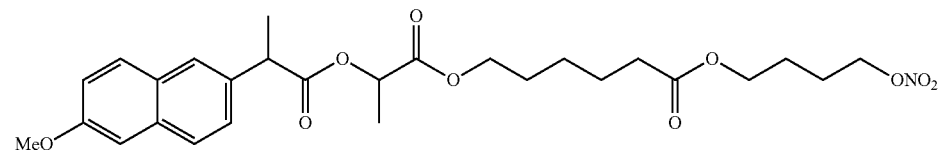

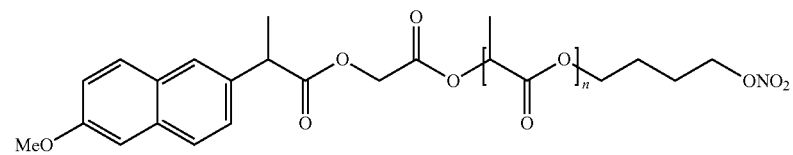

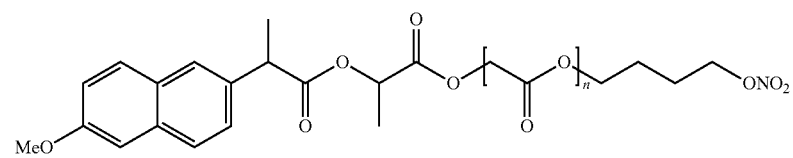

-continued
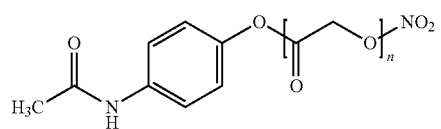
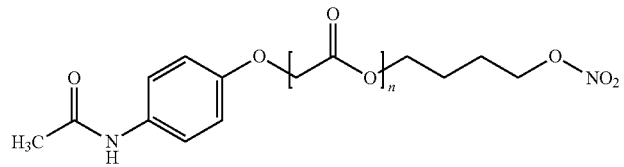
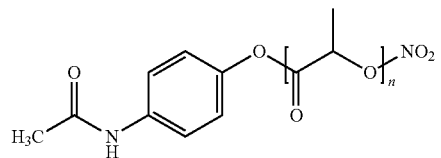
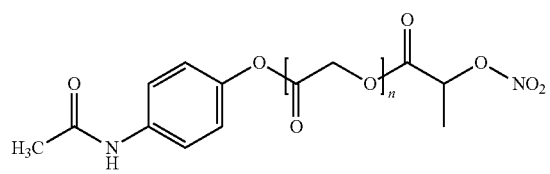
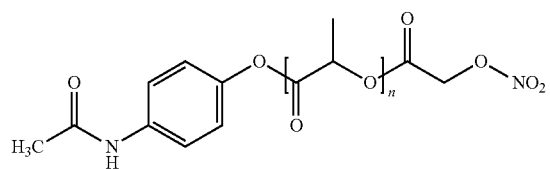
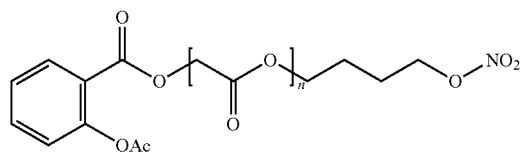
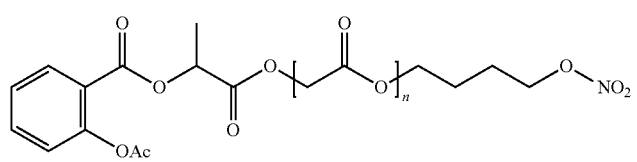
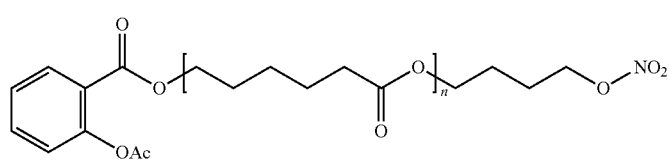
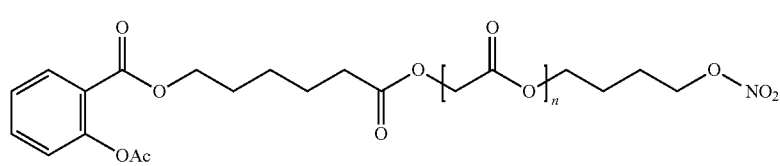
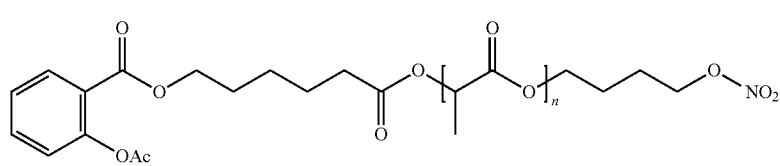

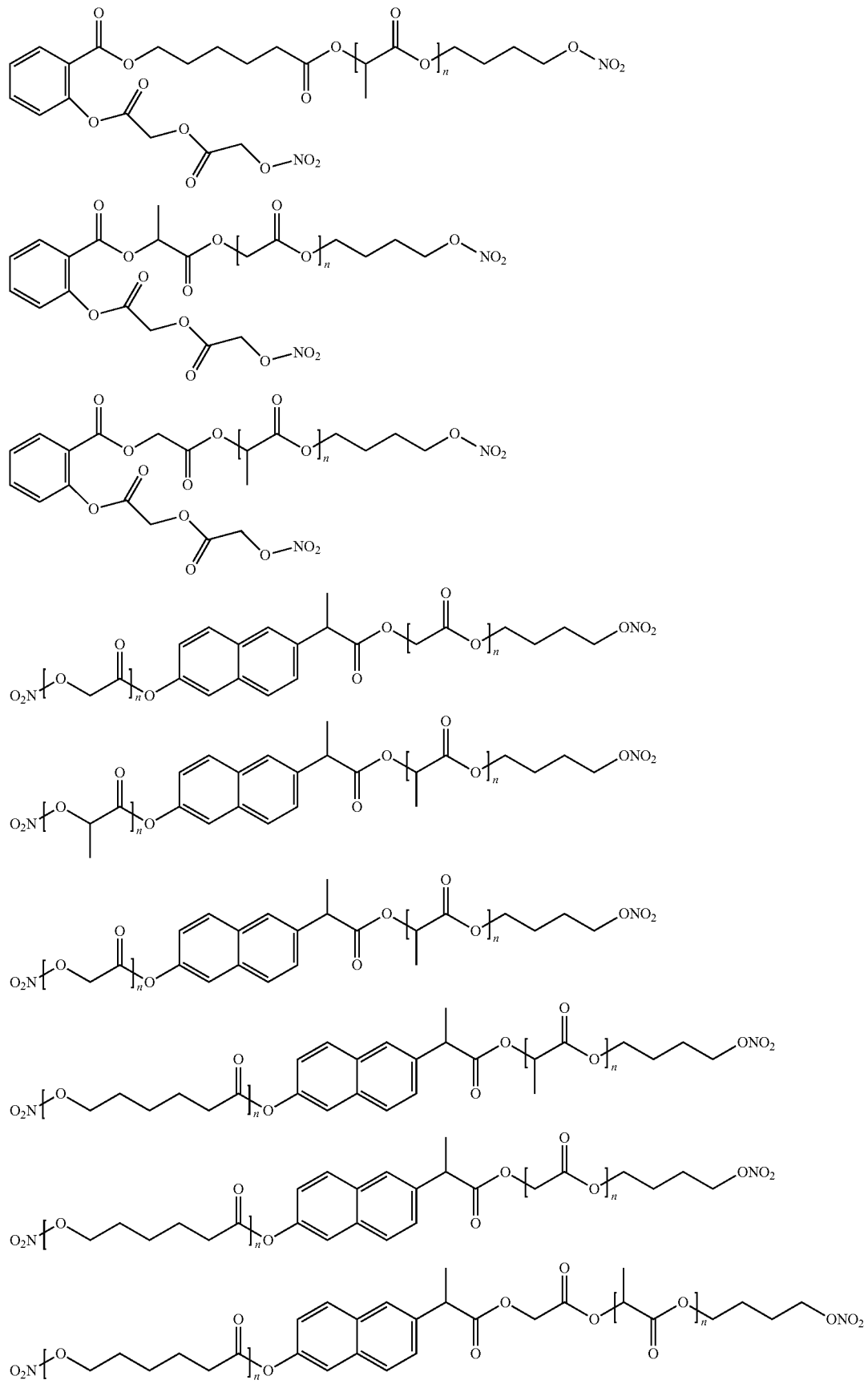

-continued
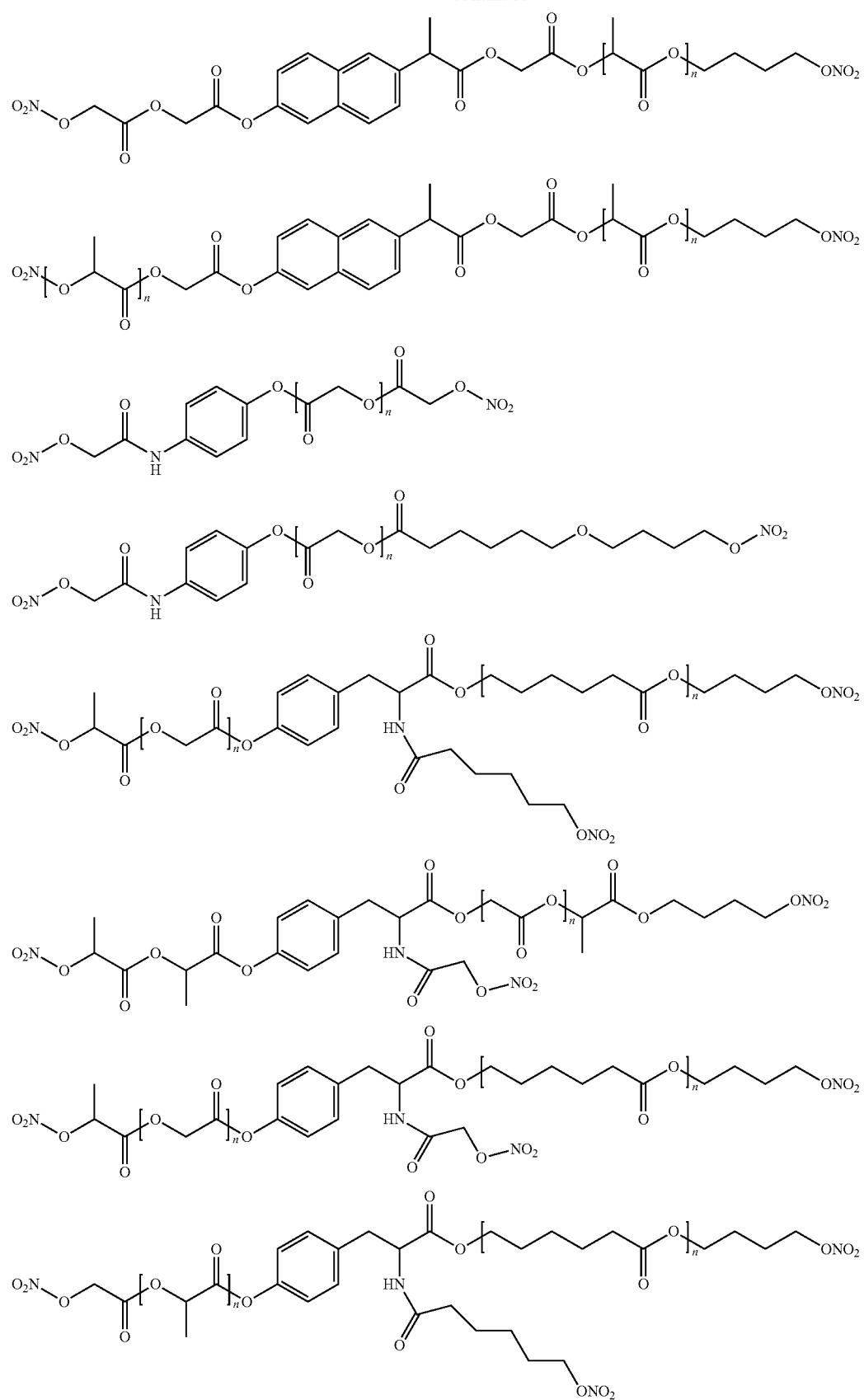

-continued
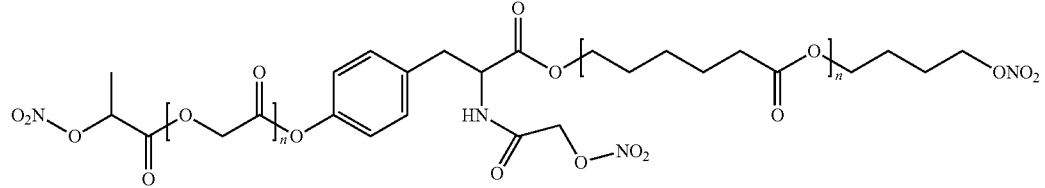
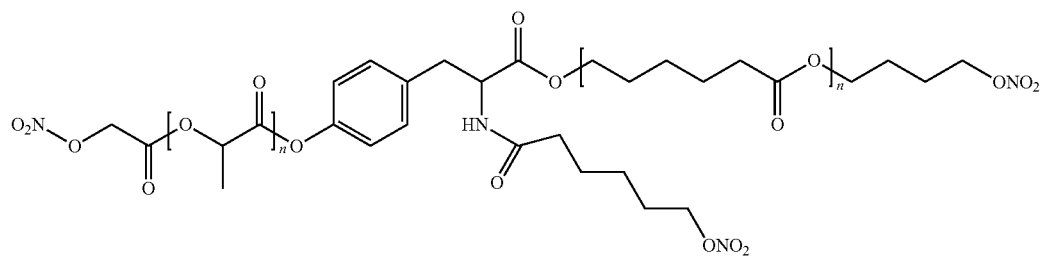
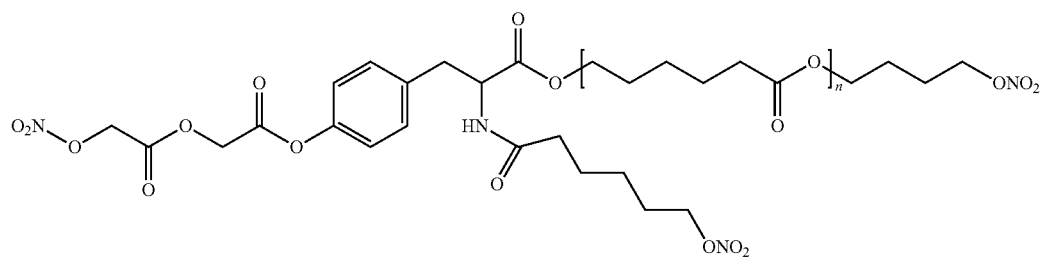
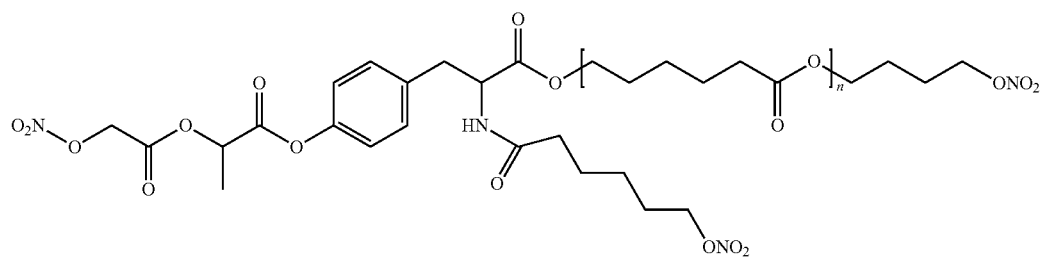
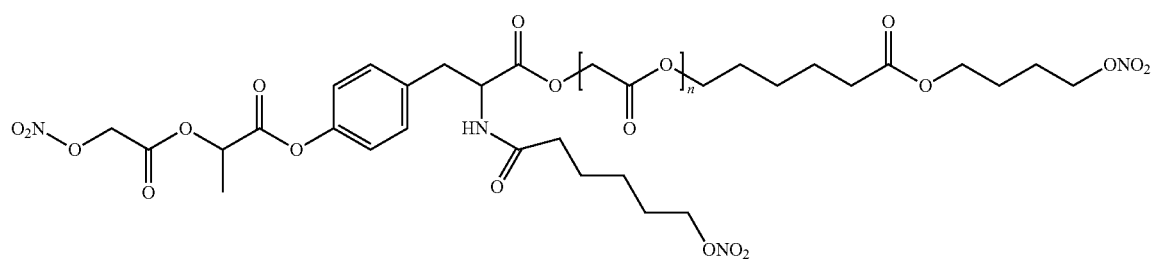
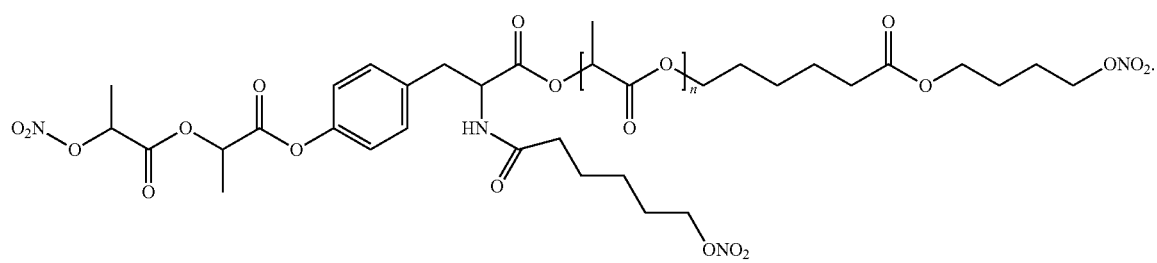

7. The oligomer of claim 1, wherein the oligomer is one of the following:
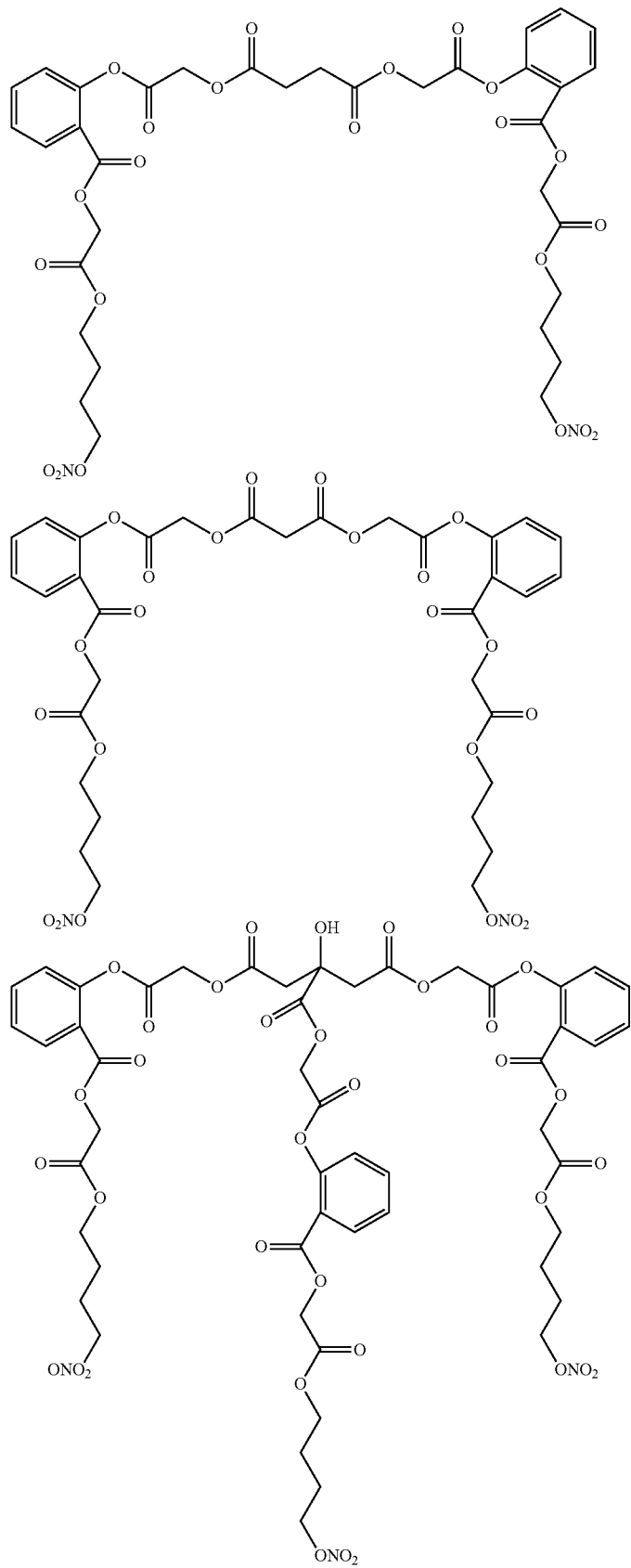

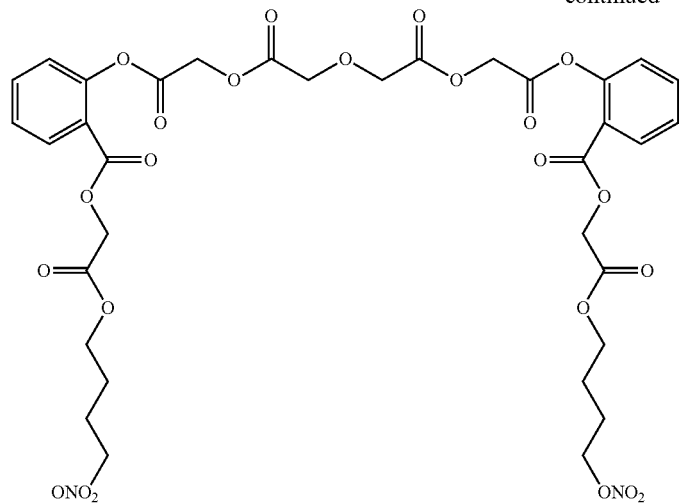
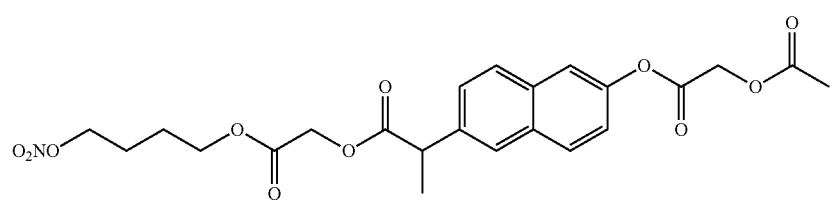
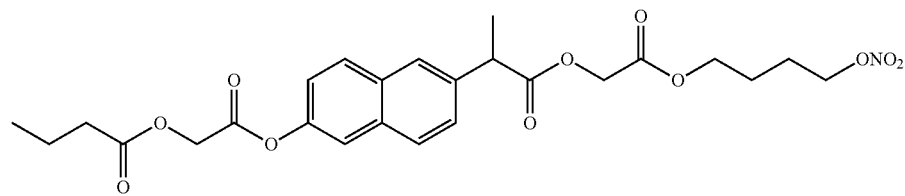
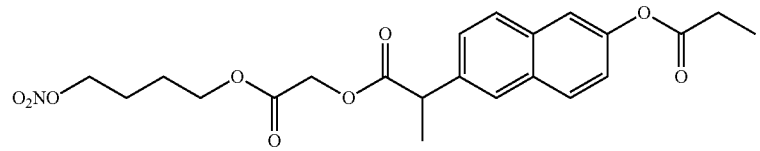
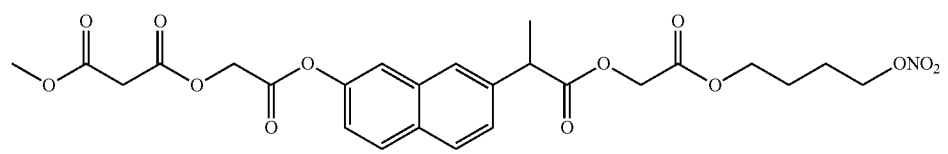
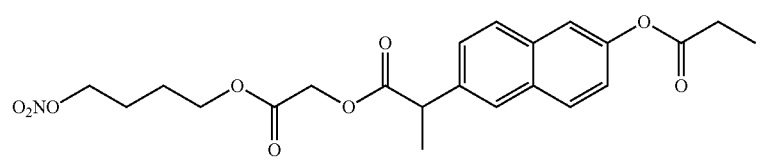
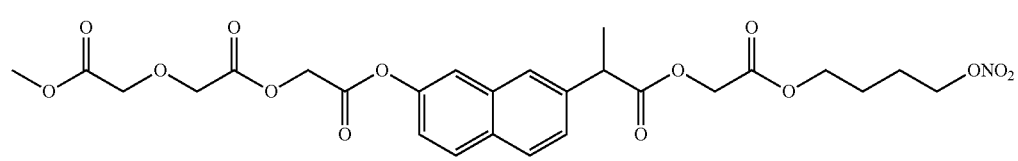
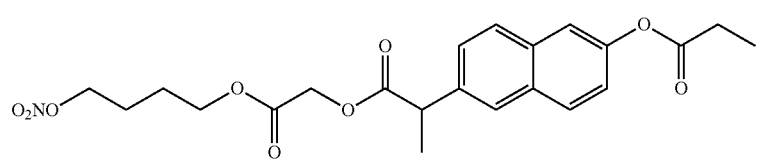

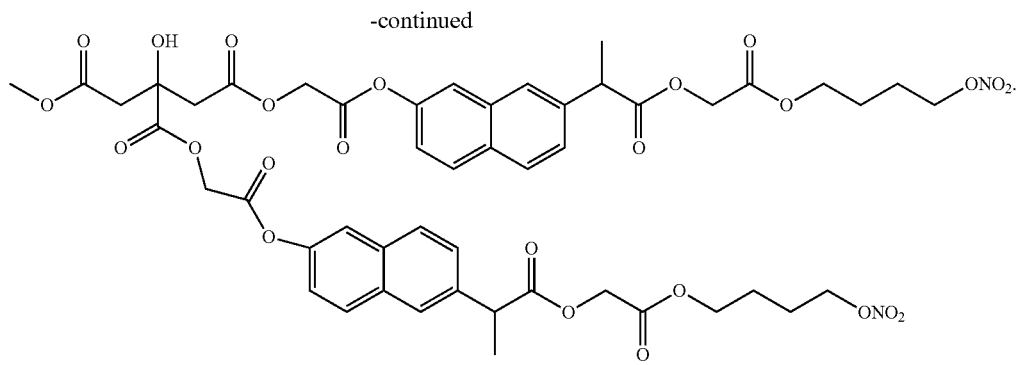

8. A composition comprising two or more distinct oligomers of claim 1.

9. The composition of claim 8, where one or more of the oligomers comprises a biologically active substance.

10. The oligomer of claim 1, wherein D or D-L comprises a antineoplastic, cardiovascular, anti-inflammatory, pain-reducing, antioxidant agent.

11. A method of treating cancer, a cardiovascular indication, inflammation, pain, or an indication treatable with an antioxidant agent comprising administering the oligomer of claim 10, which includes the corresponding biologically active agent.

12. A composition comprising an oligomer of claim 1 and a pharmaceutically acceptable excipient.

13. An implantable medical device comprising an oligomer of claim 1 and an admixed polymer.

14. The implantable medical device of claim 13, wherein the device is a stent, suture, surgical staple, mesh or bone screw.

15. A coating composition for an implantable device, comprising an oligomer of claim 1 and an admixed polymer.

16. The oligomer of claim 1, wherein the oligomer is according to one of formulas V to VIII, XI, XIV, or XVIII, where D=Drug, which is a biologically active substance according to (i):

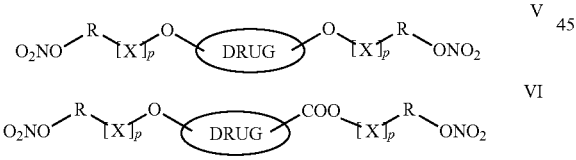

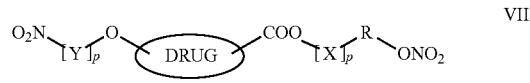

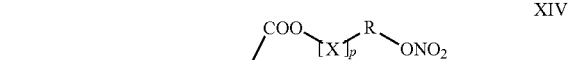

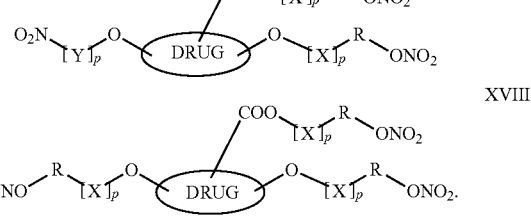

17. The oligomer of claim 1, wherein one or more of repeats X or Y of formula A comprise:

—$CH_2CH_2OCH_2COO$— (dioxanone moiety);
—$CH_2CH_2CH_2CH_2CH_2COO$— (caprolactone moiety);
—$(CH_2)_yCOO$—;
—$(CH_2CH_2O)_zCH_2COO$—;
—$COCH_2OCH_2CH_2O$— (dioxanone ester moiety);
—$COCH_2CH_2CH_2CH_2CH_2O$— (caprolactone ester moiety);
—$CO(CH_2)_mO$—; or
—$COCH_2O(CH_2CH_2O)_n$—.

* * * * *

UNITED STATES PATENT AND TRADEMARK OFFICE
CERTIFICATE OF CORRECTION

PATENT NO. : 8,062,653 B2
APPLICATION NO. : 12/508854
DATED : November 22, 2011
INVENTOR(S) : Rao S. Bezwada Page 1 of 1

It is certified that error appears in the above-identified patent and that said Letters Patent is hereby corrected as shown below:

Col. 74, lines 1-6:
In Claim 2, delete the entire line representing formula IV.

Signed and Sealed this
Twenty-fourth Day of January, 2012

David J. Kappos
*Director of the United States Patent and Trademark Office*